United States Patent
Hewawasam et al.

(10) Patent No.: US 6,613,786 B2
(45) Date of Patent: Sep. 2, 2003

(54) THIOPHENYL TRIAZOL-3-ONE DERIVATIVES AS SMOOTH MUSCLE RELAXANTS

(75) Inventors: Piyasena Hewawasam, Middletown, CT (US); John E. Starrett, Middletown, CT (US); Dalton King, Hamden, CT (US); Li-Quang Sun, Glastonbury, CT (US); Nicholas J. Lodge, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/266,373

(22) Filed: Oct. 8, 2002

(65) Prior Publication Data

US 2003/0144333 A1 Jul. 31, 2003

Related U.S. Application Data

(60) Provisional application No. 60/336,865, filed on Nov. 2, 2001.

(51) Int. Cl.[7] .................. A61K 31/4196; C07D 249/12
(52) U.S. Cl. ..................... 514/384; 548/263.2
(58) Field of Search ........................ 514/384; 548/263.2

(56) References Cited

U.S. PATENT DOCUMENTS

| 5,869,509 A | 2/1999 | Romine et al. |
| 2002/0045651 A1 | 4/2002 | Brenner et al. |

FOREIGN PATENT DOCUMENTS

| WO | WO 99/54315 | 10/1999 |

OTHER PUBLICATIONS

George, B., and Papadopoulos, E.P., "Heteocycles from N–Ethoxycarbonyl–thioamides and Dinucleophilic Reagents. 1. Dihydro–1,2,4–triazolones and 1,2,4–Oxadiazolones", *J. Org. Chem.*, 41(20), p. 3233–3237 (1976).

Nguyen, T.–H., et al., "Oxidation of Aldehyde Semicarbazones with Lead Dioxide: Application to the Syntheses of 2–Amino–1,3,4–oxadiazoles and 2.4–Dihydro–1,2,4–triazol–3–ones", *J. Heterocyclic Chem.*, 22, p. 1383–1388 (1985).

*Primary Examiner*—Alan L. Rotman
*Assistant Examiner*—Sonya Wright
(74) *Attorney, Agent, or Firm*—Aldo A. Algieri

(57) ABSTRACT

The present invention provides novel [1,2,4]triazole-3-one derivatives having the general formula (I)

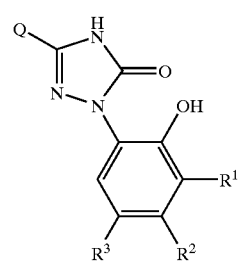

wherein:

Q is

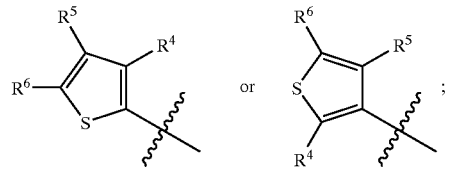

and $R^1$, $R^2$, $R^3$, $R^4$, $R^5$ and $R^6$ are as defined herein or a nontoxic pharmaceutically acceptable salt or solvate thereof which are smooth muscle relaxants and useful in treating disorders responsive to relaxation of smooth muscle such as asthma, irritable bowel syndrome, male erectile dysfunction and urinary incontinence.

21 Claims, No Drawings

THIOPHENYL TRIAZOL-3-ONE DERIVATIVES AS SMOOTH MUSCLE RELAXANTS

CROSS-REFERENCE TO RELATED APPLICATIONS

This is a non-provisional application which claims the benefit of U.S. Provisional Application No. 60/336,865 filed Nov. 2, 2001.

FIELD OF THE INVENTION

The present invention is directed to novel 2phenyl-5thiophenyl-2,4-dihydro-[1,2,4]-triazol-3-one derivatives which are smooth muscle relaxants and therefore are useful in treating disorders responsive to relaxation of smooth muscle such as asthma, irritable bowel syndrome, male erectile dysfunction and particularly urinary incontinence. The present invention is also directed to a method of treatment with the novel compounds and to pharmaceutical compositions containing them.

BACKGROUND OF THE INVENTION

Urinary incontinence is a common condition that is the frequent cause of confinement to nursing homes among the elderly. It afflicts significant numbers among both men and women and all ages. In addition studies show some degree of daily incontinence reported among as many as 17% of young apparently healthy women. Safe and reliable methods for treating incontinence are clearly needed. Urinary incontinence is a manifestation of the failure to control the muscles of the bladder or urinary sphincter. Incontinence results when the pressure within the bladder is too great as a result of excessive force exerted by the bladder muscles, or when the sphincter muscles are too weak. Urinary incontinence can be a manifestation of other diseases such as Parkinsonism, multiple sclerosis, lesions of the central nervous system, or bladder infections. Interstitial cysts can result in instability of the bladder detusor muscles and a particularly unpleasant form of urge incontinence. Urinary incontinence is believed to currently affect over 12 million people in the United States alone, and to occur in between 15 and 30% of the population over 60. The current standard of care is quite unsatisfactory. All of the current drugs now utilized to treat urinary incontinence suffer from polypharmacology and unwanted side effects.

Relaxation of the smooth muscle tissue of the bladder results in a decrease in the pressure within the bladder. Relaxation of the smooth muscle tissue of the bladder would therefore be desirable to treat urinary incontinence which results when the pressure within the bladder is too great as a result of excessive force exerted by the bladder muscles. Relaxation of other smooth muscle tissues may also result in alleviation of diseases or disorders in which excessive smooth muscle contraction has been implicated such as asthma, irritable bowel syndrome, male erectile dysfunction.

The present invention provides novel 2phenyl-5thiophenyl-2,4-dihydro-[1,2,4]-triazol-3-one derivatives which have been found to be smooth muscle relaxants. The present invention also provides compositions containing the novel 2phenyl-5thiophenyl-2,4-dihydro-[1,2,4]-triazol-3-one derivatives and a method of treating diseases or disorders responsive to the relaxation of smooth muscle tissue such as asthma, irritable bowel syndrome, male erectile dysfunction and particularly urinary incontinence.

U.S. Pat. No. 5,869,509, issued Feb. 9, 1999, provides novel diphenyl heterocyclic derivatives having the general formula

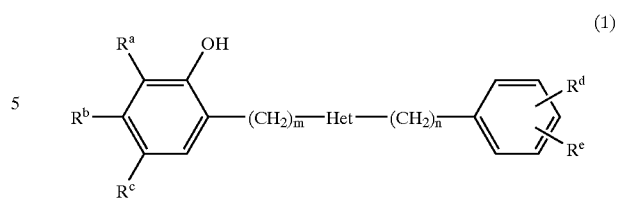

(1)

wherein "Het" is a moiety selected from the group consisting of (A) through (H):

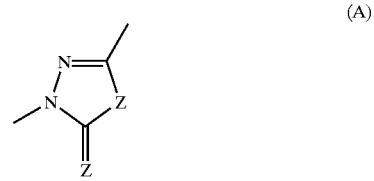

(A)

(B)

(C)

(D)

(E)

(F)

(G)

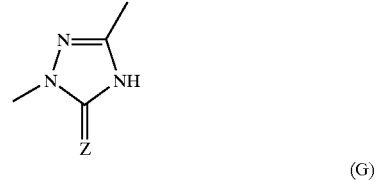

(H)

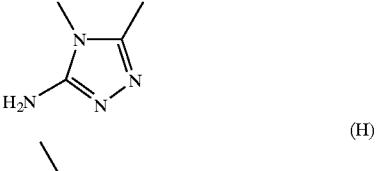

wherein Z is independently for each occurrence selected from O or S; $R^a$, $R^b$ and $R^c$ each are independently selected from hydrogen, halogen, OH, $CF_3$, $NO_2$, or

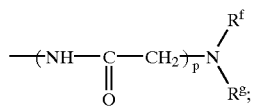

provided $R^c$ is not hydrogen; and when $R^a$ and $R^b$ are hydrogen, $R^c$ may be a heterocyclic moiety selected from the group consisting of imidazol-1-yl, morpholinomethyl, N-methylimidazol-2-yl, and pyridin-2-yl; $R^d$ and $R^e$ each are independently selected from hydrogen, halogen, $CF_3$, $NO_2$ or imidazol-1-yl; m, n and p are independently selected from 0 or 1; and $R^f$ and $R^g$ each are independently hydrogen; $C_{1-4}$ alkyl; or $R^f$ and $R^g$, taken together with the nitrogen atom to which they are attached, is a heterocyclic moiety selected from the group consisting of N-methylpiperazine, morpholine, thiomorpholine, N-benzylpiperazine and imidazolinone.

A method for preparing [1,2,4]-2,4-dihydrotriazolones was disclosed in *J. Org. Chem.* 1976, 41, 3233–3237, including a single thiophen-2-yl derivative, 2phenyl-5thiophen-2-yl-2,4-dihydro-[1,2,4]triazol-3-one, shown below. *Nippon Kagaku Zasshi* 1968, 89, 69–74 also discloses 2phenyl-5thiophen-2-yl-2,4-dihydro-[1,2,4]triazol-3-one, prepared by the ring closure reaction of the corresponding 1-aryl-4-acyl semicarbazide.

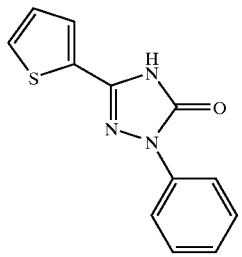

A method to oxidize oxadiazoles to provide [1,2,4]-2,4-dihydrotriazolones was reported in *J. Heterocyclic Chem.* 1985, 22, 1383–1388. The four 5-(5-nitrothiophen-2-yl)-2,4-diphenyl-2,4-dihydro-[1,2,4]triazol-3-one derivatives shown below were disclosed in this publication.

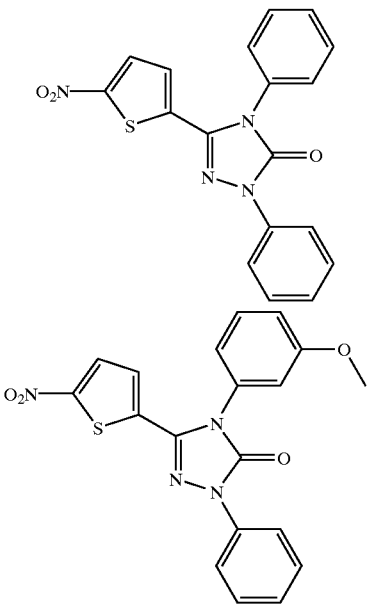

International Application WO9954315, published Oct. 28,1999, discloses triazolones of the general formula shown below, which act as neuroprotectants. In the general structure $R_2$ may be a carbon linked 5 or 6-membered saturated or unsaturated heterocycle, such that 1, 2, 3, or 4 atoms can be chosen from oxygen, nitrogen or sulfur and the substituents can be $C_{1-6}$alkyl or benzyl. $R_1$ may be phenyl or substituted phenyl.

SUMMARY OF THE INVENTION

Novel compounds of formula I are useful to treat disorders responsive to relaxation of smooth muscle:

wherein:
Q is

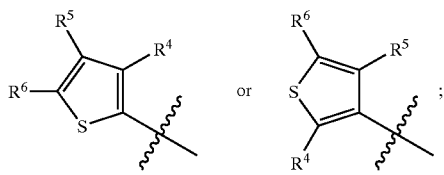

R¹ and R² are each independently selected from the group consisting of hydrogen, halogen, $C_{1-6}$alkyl and $C_{2-6}$alkenyl;
R³ is halogen or trifluoromethyl; and
R⁴, R⁵ and R⁶ are each independently selected from the group consisting of hydrogen, halogen and $C_{1-6}$alkyl;

or a nontoxic pharmaceutically acceptable salt or solvate thereof. The present invention also provides pharmaceutical compositions thereof and methods which employ them.

DETAILED DESCRIPTION OF THE INVENTION

The term "$C_{1-6}$ alkyl" as used herein and in the claims (unless the context indicates otherwise) means straight or branched chain alkyl groups such as methyl, ethyl, propyl, isopropyl, butyl, isobutyl, t-butyl, pentyl, 3-methylbutyl, hexyl and the like. The term "$C_{2-6}$ alkenyl" as used herein and in the claims (unless the context indicates otherwise) means straight or branched chain alkenyl groups such as ethenyl (i.e. vinyl), propenyl, allyl, butenyl, 3-methylbutenyl, pentenyl, hexenyl and the like. Unless otherwise specified, the term "halogen" as used herein and in the claims is intended to include bromine, chlorine, iodine and fluorine while the term "halide" is intended to include bromide, chloride and iodide anion.

The term "nontoxic pharmaceutically acceptable salt" as used herein and in the claims is intended to include nontoxic acid and base addition salts. Suitable acids include sulfuric, phosphoric, hydrochloric, hydrobromic, hydroiodic, citric, acetic, benzoic, cinnamic, fumaric, mandelic, phosphoric, nitric, mucic, isethionic, palmitic, heptanoic, and the like. Suitable inorganic bases, such as alkali and alkaline earth metal bases, include metallic cations such as sodium, potassium, magnesium, calcium and the like.

Generally, pharmaceutically acceptable salts of the invention are those in which the counter-ion does not contribute significantly to the toxicity or pharmacological activity of the salt. In some instances, they have physical properties which make them more desirable for pharmaceutical formulations, such as solubility, lack of hygroscopicity, compressibility with respect to tablet formation and compatibility with other ingredients with which the substance may be used for pharmaceutical purposes. The salts are routinely made by admixture of a Formula I compound with the selected acid or base, preferably by contact in solution employing an excess of commonly used inert solvents such as water, ether, benzene, methanol, ethanol, ethyl acetate and acetonitrile. They may also be made by metathesis or treatment with an ion exchange resin under conditions in which the appropriate ion of a salt of the substance of the Formula I is replaced by another ion under conditions which allow for separation of the desired species such as by precipitation from solution or extraction into a solvent, or elution from or retention on an ion exchange resin.

Certain compounds of the present invention can exist as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the composition that is sufficient to show a meaningful patient benefit, i.e., healing of acute conditions characterized by relaxation of smooth muscle or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with constriction of smooth muscle tissue by administration of a compound of Formula I.

The compounds of Formula I and intermediates useful for their synthesis may be prepared by various procedures such as those illustrated herein in the examples, in the Reaction Schemes, and by variations thereof which would be evident to those skilled in the art.

PREPARATION OF INTERMEDIATES

Intermediates useful for the preparation of compounds of Formula I may be prepared by the procedures outlined in Reaction Schemes I–V.

REACTION SCHEME I

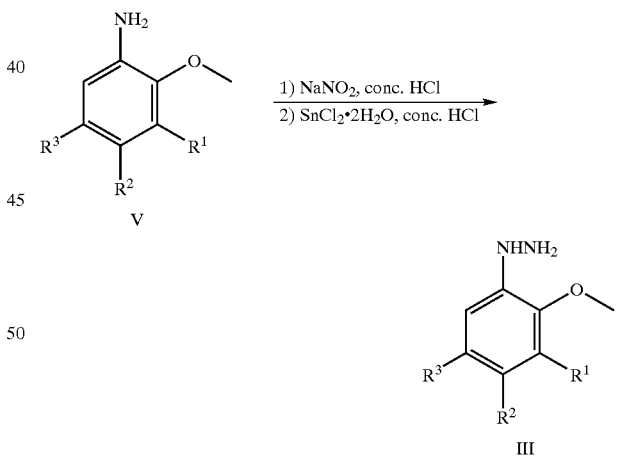

Reaction Scheme I depicts the preparation of a (2-methoxyphenyl)hydrazine derivative III from the corresponding 2-methoxyaniline derivative V. The (2-methoxyphenyl)hydrazine derivative III may be prepared by treatment of a solution of the corresponding 2-methoxyaniline derivative V (1.0 equivalent) in concentrated hydrochloric acid (concentration approximately 0.27 M) with aqueous sodium nitrite (1.3 equivalents, concentration approximately 3.5 M) at approximately −10° C. The resulting mixture is stirred at 0° C. for approximately one hour then cooled to −35° C. and treated with a solution of Tin(II) chloride dihydrate in concentrated hydrochloric acid (2.6 equivalents, concentration 4.0 M). The reaction mixture is stirred at 0° C. for one hour then the resulting solid is collected by filtration and washed with concentrated hydrochloric acid and water. The resulting solid is then stirred in a mixture of an appropriate solvent such as ethyl acetate or dichloromethane and aqueous sodium hydroxide (typically 2M or 3 M). The organic layer is separated, dried over anhydrous sodium sulfate and concentrated in vacuo to provide the (2-methoxyphenyl)hydrazine derivative III.

REACTION SCHEME II

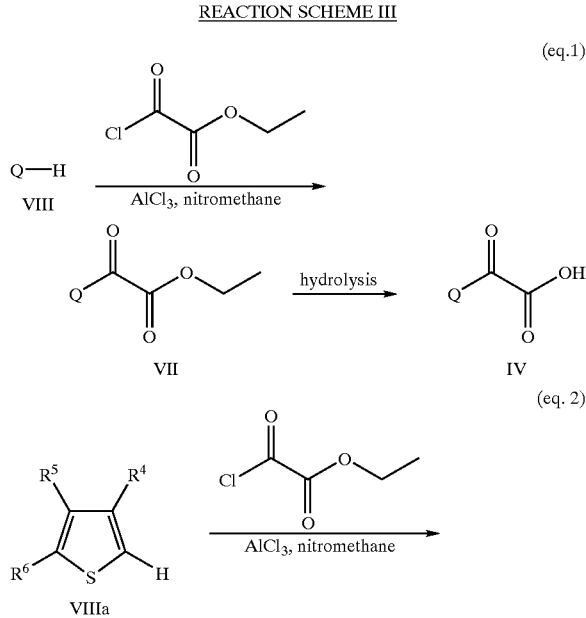

Reaction Scheme II depicts the preparation of a (2-methoxyphenyl)hydrazine derivative III from the corresponding (2-methoxyphenyl)diazo salt derivative VI (X represents a halide such as chloride). A solution of the (2-methoxyphenyl)diazo salt derivative VI in concentrated hydrochloric acid is treated with a solution of Tin(II) chloride dihydrate in concentrated hydrochloric acid as described previously for Reaction Scheme I. After workup, as described for Reaction Scheme I, the (2-methoxyphenyl) hydrazine derivative III may be obtained.

REACTION SCHEME III

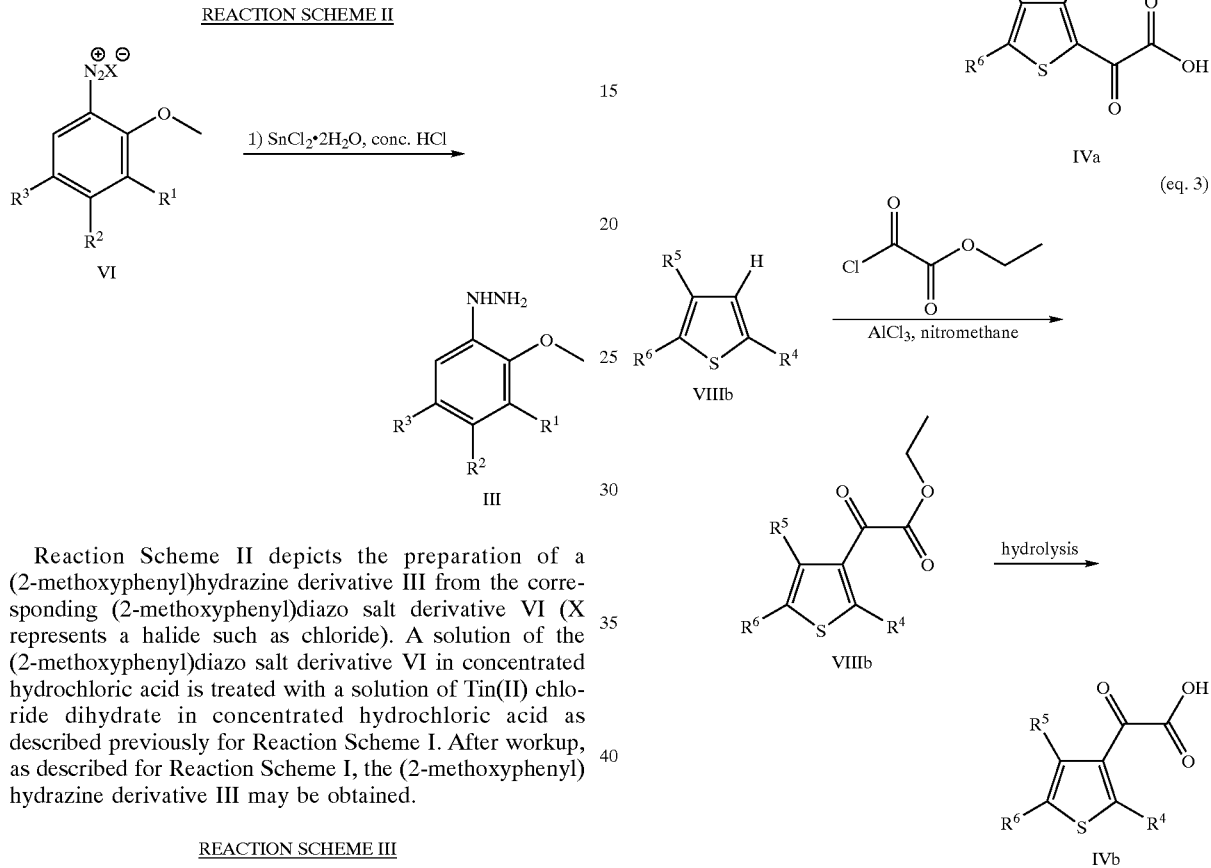

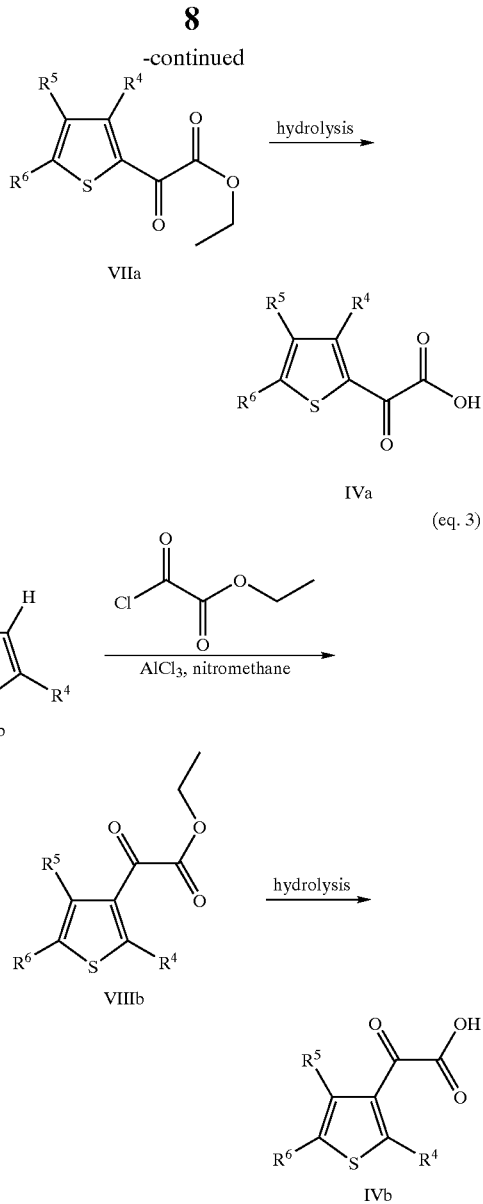

Reaction Scheme III shows the preparation of thiophenyl oxo-acetic acid derivatives IV, IVa and IVb from the corresponding appropriate thiophene derivatives VIII, VIIIa and VIIIb (equations 1–3, respectively). A mixture of an appropriate thiophene derivative such as VIII, VIIIa or VIIIb (1.0 equivalent) and ethyl oxalyl chloride (1.5 equivalents) may be treated with a solution of aluminum trichloride in nitromethane (1.5 equivalents, concentration approximately 3.6 M) at a temperature of approximately 0–10° C. The reaction mixture is stirred at approximately 0° C. for one hour, room temperature for three hours and then poured into ice water. The resulting mixture is then extracted with an appropriate solvent such as diethyl ether. The organic layer is washed with saturated aqueous sodium bicarbonate, dried over anhydrous sodium sulfate and concentrated in vacuo. The residue is typically purified by either distillation or flash chromatography on silica gel to provide the thiophenyl oxo-acetic acid ethyl ester VII, VIIa or VIIb, respectively.

The thiophenyl oxo-acetic acid ethyl ester VII, VIIa or VIIb may be subjected to hydrolysis to provide the corresponding thiophenyl oxo-acetic acid IV, IVa or IVb. The hydrolysis may be carried out under either acidic or basic conditions. Basic hydrolysis can typically be carried out by treating a solution of a thiophenyl oxo-acetic acid ethyl ester such as VII, VIIa or VIIb (1.0 equivalent) in an aqueous mixture of an appropriate solvent such as methanol, tetrahydrofuran or 1,4-dioxane with a suitable base such as aqueous sodium hydroxide or potassium hydroxide (typically 1.5 equivalents) for a period of four to twenty hours at a temperature range of 0° C. to room temperature. The reaction mixture can be worked up by acidification with an appropriate acid such as hydrochloric acid or acetic acid followed by extraction with an appropriate solvent such as ethyl acetate or dichloromethane. The resulting organic layer may then be concentrated in vacuo to provide the thiophenyl oxo-acetic acid IV, IVa or IVb, respectively. If desired, the thiophenyl oxo-acetic acid IV, IVa or IVb could then be further purified by recrystallization or preparative HPLC. Alternatively, the hydrolysis of the thiophenyl oxo-acetic acid ethyl ester VII, VIIa or VIIb to the corresponding thiophenyl oxo-acetic acid IV, IVa or IVb may be carried out under acidic conditions. The acidic hydrolysis is typically carried out by refluxing a thiophenyl oxo-acetic acid ethyl ester such as VII, VIIa or VIIb in a mixture of acetone and water in the presence of hydrochloric acid for one to four hours. The reaction mixture is then extracted with an appropriate solvent such as dichloromethane and the organic layer concentrated in vacuo to provide the thiophenyl oxo-acetic acid IV, IVa and IVb, respectively.

Reaction Scheme IV depicts an alternative route to the preparation of thiophenyl oxo-acetic acid derivatives IV, IVa and IVb (equations 1–3, respectively). One equivalent of an appropriate acetyl thiophene derivative such as IX, IXa or IXb can be treated with selenium dioxide (1.5 equivalents) in pyridine at approximately 70° C. for three hours. The reaction mixture is allowed to cool to room temperature and then poured into 1N HCl. The resulting mixture is extracted with an appropriate solvent such as diethyl ether. The organic layer can then be dried over anhydrous sodium sulfate and concentrated in vacuo to provide the thiophenyl oxo-acetic acid derivatives IV, IVa and IVb, respectively. The products thus obtained can be further purified by standard techniques such as recrystallization or preparative HPLC.

REACTION SCHEME IV

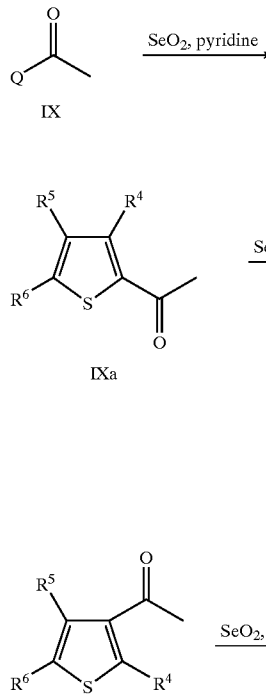

REACTION SCHEME V

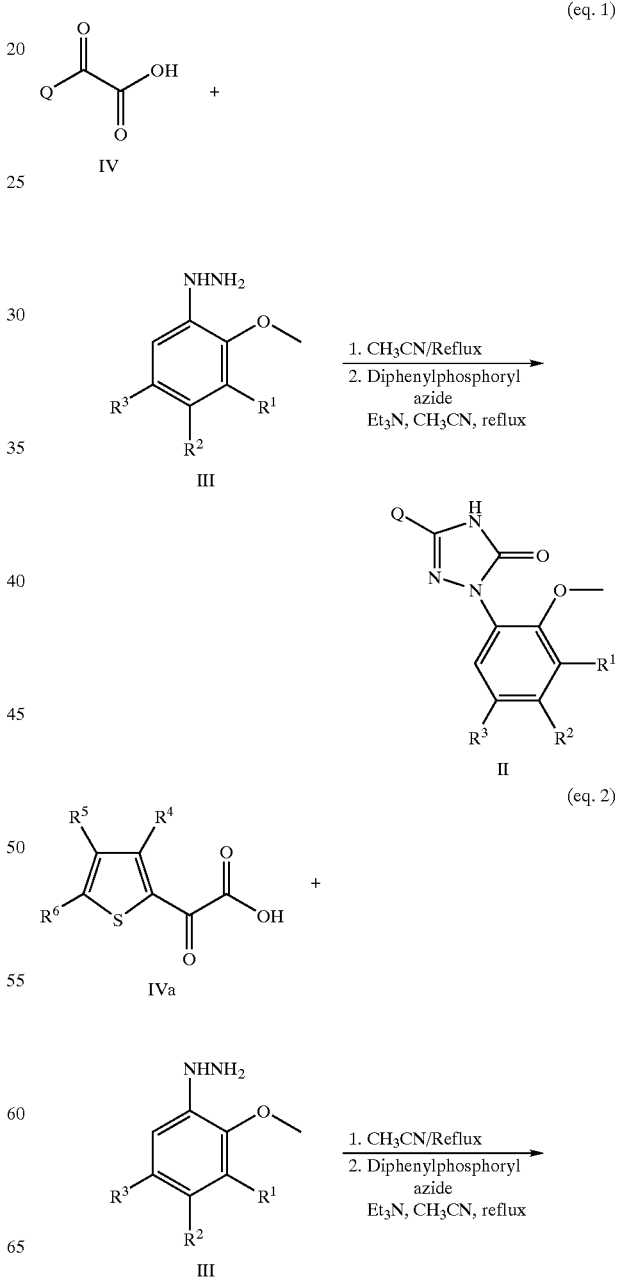

-continued

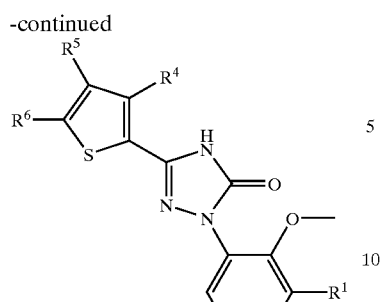

IIa (eq. 3)

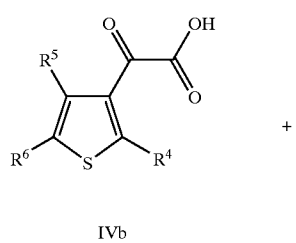

IVb

+

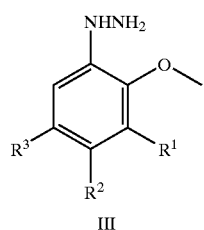

III

1. CH₃CN/Reflux
2. Diphenylphosphoryl azide
Et₃N, CH₃CN, reflux

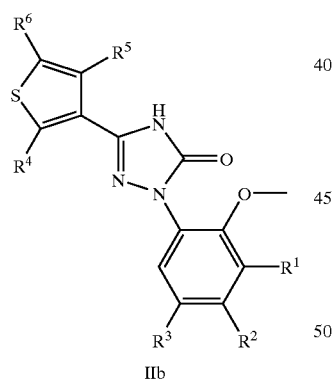

IIb

The 2-(2-methoxyphenyl)-5thiophenyl-2,4-dihydro-[1,2,4]-triazol-3-one derivatives of Formulae II, IIa and IIb can be prepared as depicted in Reaction Scheme V (equations 1–3, respectively). An appropriate thiophenyl-oxo-acetic acid such as IV, IVa or IVb (1.0 equivalent) and a (2-methoxyphenyl)hydrazine derivative III (1.0 equivalent) is refluxed in acetonitrile (15–25 mL/mmol starting material) for 30–60 min. The reaction is cooled to room temperature then triethylamine (1.1 equivalent) and diphenylphosphorylazide (1.1 equivalent) is added, and the reaction heated at reflux for a period of approximately 3 to 18 hours. After cooling to room temperature, solids are collected by filtration and washed with acetonitrile and diethyl ether to provide the corresponding 2-(2-methoxyphenyl)-5thiophenyl-2,4-dihydro-[1,2,4]-triazol-3-one II, IIa or IIb. If necessary, the product is further purified by standard techniques such as flash chromatography on silica gel 60 typically eluted with hexane/ethyl acetate.

Preparation of Compounds of Formula I

The compounds of Formula I were prepared according to the methods depicted below in Schemes VI.

REACTION SCHEME VI (eq. 1)

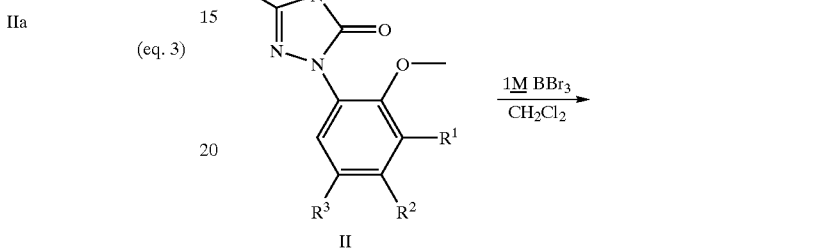

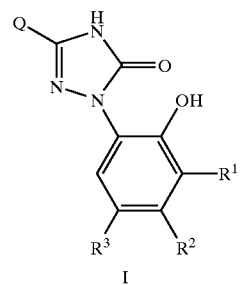

I (eq. 2)

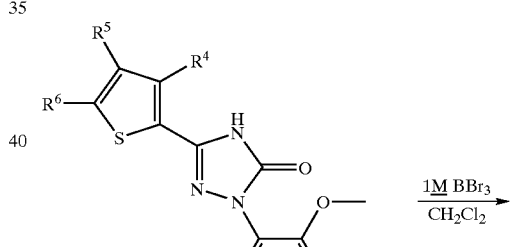

IIa

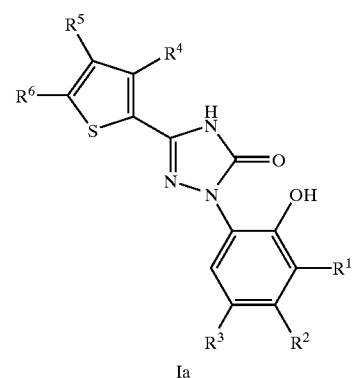

Ia

-continued

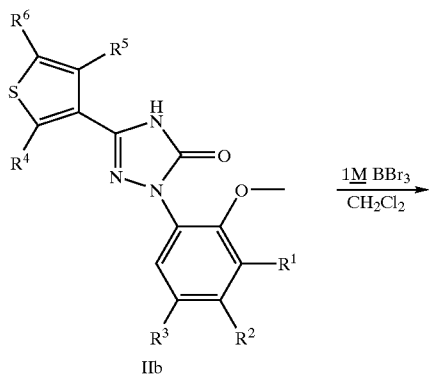

(eq. 3)

IIb

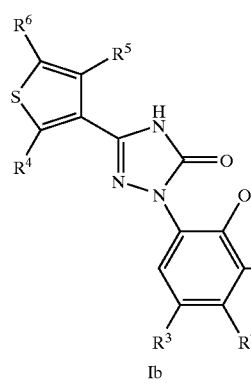

Ib

Reaction Scheme VI depicts the preparation of compounds of Formulae I, Ia and Ib from the corresponding intermediates of formulae II, IIa and IIb, respectively. The triazolone methyl ether of formulae II, IIa or IIb (1.0 equivalent) is suspended in anhydrous dichloromethane (20–25 ml/mmol of formulae II, IIa or IIb) under argon and cooled to −78° C. A 1M solution of boron tribromide (BBr₃, 2–3 equivalents) in anhydrous dichloromethane is added via a dropping funnel over a 45 minute period. After the addition is complete, the reaction is warmed to room temperature and stirred for approximately 5 hours. The reaction may be quenched by the addition of water (typically 5–10 ml). Volatile solvent is removed under vacuum and the crude product filtered and washed with water, then heated in a mixture of acetone and ethanol for approximately 15 minutes. After cooling to room temperature, the purified product is filtered and washed with acetone and ethanol. The solid is dried under high vacuum to provide the corresponding products of formulae I, Ia or Ib, respectively. If necessary, the product can be further purified by recrystallization from an appropriate solvent such as tetrahydrofuran.

Compounds of Formula I, Ia or Ib may contain an allyl group ($CH_2CH=CH_2$) at the positions designated $R^1$ or $R^2$. The allyl group at the $R^1$ or $R^2$ position of a compound of Formula I, Ia or Ib may be isomerized by treatment with rhodium trichloride dihydrate in refluxing ethanol to provide the corresponding prop-1-en-1-yl ($CH=CHCH_3$) derivative. The allyl group at the $R^1$ or $R^2$ position of a compound of Formula I, Ia or Ib may also be reduced by hydrogenation using 10%Pt(S)/C catalyst in ethanol at 50 psi for 3 hours.

In a preferred embodiment of the invention are compounds of Formula Ic

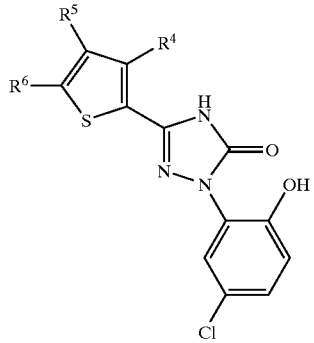

Ic wherein $R^4$, $R^5$ and $R^6$ are each independently selected from the group consisting of hydrogen, halogen and $C_{1-6}$alkyl; or a nontoxic pharmaceutically acceptable salt or solvate thereof.

In another preferred embodiment of the invention are compounds of Formula Id

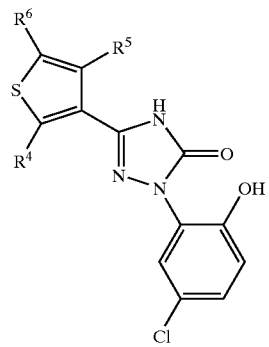

Id wherein $R^4$, $R^5$ and $R^6$ are each independently selected from the group consisting of hydrogen, halogen and $C_{1-6}$alkyl; or a nontoxic pharmaceutically acceptable salt or solvate thereof. A more preferred embodiment is a compound of Formula Id wherein $R^4$ and $R^6$ are halogen and $R^5$ is hydrogen.

In yet another preferred embodiment of the present invention are compounds of Formula Ie

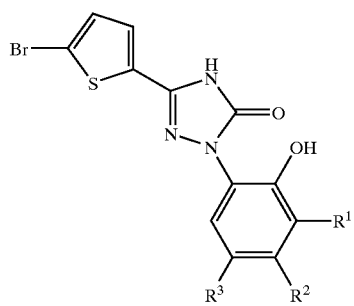

Ie wherein $R^1$ and $R^2$ are each independently selected from the group consisting of hydrogen, halogen, $C_{1-6}$alkyl and $C_{2-6}$alkenyl; $R^3$ is halogen or trifluoromethyl; or a nontoxic pharmaceutically acceptable salt or solvate thereof.

In still yet another preferred embodiment of the present invention are compounds of Formula If

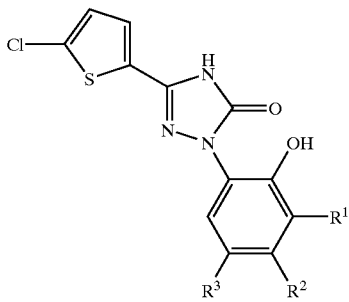

If wherein $R^1$ and $R^2$ are each independently selected from the group consisting of hydrogen, halogen, $C_{1-6}$alkyl and $C_{2-6}$alkenyl; $R^3$ is halogen or trifluoromethyl; or a nontoxic pharmaceutically acceptable salt or solvate thereof.

In another aspect, this invention provides a method for the treatment of disorders responsive to relaxation of smooth muscle in a mammal in need thereof, which comprises administering to said mammal a therapeutically effective amount of a compound of Formula I, or a nontoxic pharmaceutically acceptable salt thereof. Preferably, the compounds of Formula I are useful in the treatment of urinary incontinence, asthma, irritable bowel syndrome or male erectile dysfunction and more preferably in the treatment of urinary incontinence.

In still another aspect, this invention provides pharmaceutical compositions comprising at least one compound of Formula I in combination with a pharmaceutically acceptable adjuvant, carrier or diluent.

Biological Activity

Smooth muscle tissue is present in mammals in the lung, bowel, male genitalia and bladder. Abnormal smooth muscle contractions in these tissues can therefore cause certain types of asthma, irritable bowel syndrome, male sexual dysfunction and urinary incontinence. For example, urge urinary incontinence (UUI) is the most prevalent type of urinary incontinence and is characterized by abnormal spontaneous bladder smooth muscle contractions, which arise during bladder filling. Urge urinary incontinence (UUI) may therefore be treated with compounds which partially inhibit contractions of the bladder smooth (detrusor) muscle. Likewise, partial inhibition of contractions in smooth muscle tissue present in the mammalian lung, bowel and male genitalia may provide effective treatment for disorders such as asthma, irritable bowel syndrome and male erectile dysfunction, respectively.

The ability of the compounds of the present invention to relax smooth muscle tissue was assessed by their ability to inhibit carbachol induced contractions in mammalian smooth muscle tissue. More specifically, the compounds of the present invention were screened in an in vitro rat bladder strip model to estimate their inhibitory effects on 10 µM carbachol induced contraction of the rat bladder strip according to the following experimental protocol.

Experimental Protocol

1. Bladder Strip Tissue Preparation

Male rats were sacrificed by decapitation, the bladder removed and cleaned of connective tissue. Strips of bladder were then cut from the bladder body and placed in organ baths, suspended between a fixed hook and a force transducer, containing oxygenated physiological buffer maintained at 37° C.

2. Experimental Design

The bladder strips were primed by stimulating them with 10 µM carbachol to evoke a contraction. The strips were then washed multiple times with fresh physiological buffer and allowed to fully relax. Following a period of recovery, the strips were again challenged with 10 µM carbachol to produce a contraction; this contractile response served as control response. The strips were again washed multiple times and allowed to fully relax (45 minutes). Test compound (3 µM) or vehicle was then added to each organ bath. Following a one hour incubation period, the strips were again stimulated with 10 µM carbachol and the contractile response measured.

3. Data Analysis

The percent inhibition of the carbachol response by the test compounds was calculated by comparing control and post-compound carbachol responses normalized for vehicle effects. The percentage inhibition for each compound at 3 µM concentration is provided below in Table 1.

TABLE 1

| Example No. | Percent Inhibition* |
|---|---|
| 1 | +++ |
| 2 | +++ |
| 3 | +++ |
| 4 | +++ |
| 5 | +++ |
| 6 | +++ |
| 7 | +++ |
| 8 | ++ |
| 9 | + |
| 10 | ++ |
| 11 | ++ |
| 12 | ++ |
| 13 | +++ |
| 14 | +++ |
| 15 | + |
| 16 | ++ |
| 17 | ++ |
| 18 | ++ |
| 19 | +++ |
| 20 | ++ |
| 21 | ++ |
| 22 | ++ |
| 23 | ++ |
| 24 | ++ |
| 25 | ++ |
| 26 | +++ |
| 27 | +++ |
| 28 | ++ |
| 29 | ++ |
| 30 | ++ |
| 31 | ++ |
| 32 | +++ |

*at 3 µM expressed as percent inhibition over controls
+ = 5–20%
++ = 20–35%
+++ = 35–50%

The results of the above biological test demonstrate that the compounds of the present invention are effective inhibitors of the 10 µM carbachol induced rat bladder contractions as these contractions were inhibited within the range of 5 to 50 percent. Thus, the compounds of the present invention are useful as smooth muscle relaxants in mammals, particularly in humans, for the treatment of disorders responsive to smooth muscle relaxation such as asthma, irritable bowel syndrome, male erectile dysfunction and particularly urinary incontinence.

In yet another embodiment, this invention relates to a method for treating disorders responsive to relaxation of smooth muscle tissue in a mammal in need thereof, which comprises administering to said mammal a therapeutically effective amount of a compound of Formula I or a non-toxic pharmaceutically acceptable salt, solvate or hydrate thereof.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 µg/kg to 100 mg/kg body weight. For parenteral administration, the dose may be in the range of 1 µg/kg to 100 mg/kg body weight for intravenous administration. The active ingredient will preferably be administered either continuously or in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances, including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Gallenkamp capillary melting point apparatus temperatures are uncorrected. Proton magnetic resonance ($^1$H NMR) was recorded on a Bruker AC 300. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Low resolution mass spectra (MS) and the apparent molecular (MH$^+$) or (M–H)$^{31}$ was determined on a Finnigen TSQ 7000. High resolution mass spectra was determined on a Kratos MS50 in FAB mode using cesium iodide/glycerol as internal reference. The element analysis are reported as percent by weight.

The following preparations illustrate procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

PREPARATION OF INTERMEDIATES

Preparations 1a–1q

Preparations 1a–1q, IVa, were prepared according to the general methods as described previously for Reaction Schemes III or IV and according to the specific methods as described below.

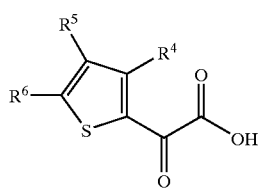

IVa

Preparation 1a

(5-Bromothiophen-2-yl)-oxo-acetic acid (IVa, $R^4$=$R^5$=H, $R^6$=Br)

Step 1: Preparation of (5-bromothiophen-2-yl)-oxo-acetic acid ethyl ester

A solution of $AlCl_3$ (61 g, 455 mmol) in 125 ml nitromethane was added dropwise to a stirring mixture of ethyl oxalyl chloride (50.8 ml, 455 mmol) and 2-bromothiophene (49.5 g, 304 mmol) at 0–5° C. The reaction was stirred for 1 hour at 0° C. following the addition step, then 3 hours at room temperature. The reaction was then poured into 1 L ice water and extracted with diethyl ether (3×250 ml). The combined diethyl ether layers were extracted with 250 ml saturated $NaHCO_3$ solution. The organic layer was then dried over $Na_2SO_4$, and concentrated under vacuum. The residue was Kugelrohr distilled to yield (5-bromothiophen-2-yl)-oxo-acetic acid ethyl ester as a yellow solid (45.7 g, 57%). MS ($MH^+$): 262.98. $^1$H NMR (300 MHz, $CDCl_3$) δ7.90 (1H, d, J=4.1 Hz), 7.17 (1H, d, J=4.2 Hz), 4.42 (2H, q, J=7.2 Hz), 1.43 (3H, t, J=7.1 Hz). m.p. 63–66° C.

Step 2: Preparation of (5-bromothiophen-2-yl)-oxo-acetic acid (5-Bromothiophen-2-yl)-oxo-acetic acid ethyl ester (45.6 g, 173 mmol) was dissolved in a mixture of 100 ml THF, 100 ml methanol, and 300 ml water, then treated with 10 N NaOH (26 ml, 260 mmol) at room temperature for 20 hours. Volatile solvents were removed by rotary evaporation. The residue was dissolved in 2 L water and extracted with diethyl ether (250 ml). The aqueous layer was acidified to pH 1 with 6 N HCl, and extracted three times with diethyl ether (3×300 ml). The combined diethyl ether extracts were dried over $Na_2SO_4$ and concentrated under vacuum to yield Preparation 1a (38.7 g, 95%). The product was then recrystallized from diethyl ether. m.p. 119–120° C.; MS (M−H)$^-$: 235.1; $^1$H NMR (300 MHz, $CDCl_3$) δ9.00 (1H, br s), 8.15 (1H, d, J=4.2 Hz), 7.16 (1H, d, J=4.2 Hz). $^{13}$C NMR (75 MHz, $CDCl_3$) δ173.80, 159.58, 140.14, 137.17, 132.58, 130.48. IR (KBr) 3326, 3124, 1756, 1634, 1415, 1363, 1308, 1253 cm$^{-1}$.

Anal. Calcd. for $C_6H_3O_3SBr$: C, 30.66; H, 1.29; Br, 33.99. Found: C, 30.92; H, 1.46; Br, 33.94.

Preparation 1b

(5-Chlorothiophen-2-yl)-oxo-acetic acid (IVa, $R^4$=$R^5$=H, $R^6$=Cl)

Step 1: Preparation of (5-chlorothiophen-2-yl)-oxo-acetic acid ethyl ester

A solution of $AlCl_3$ (10 g, 75 mmole) in 20 ml nitromethane was added dropwise to a stirring mixture of ethyl oxalyl chloride (8.4 ml, 75 mmol) and 2-chlorothiophene (4.6 ml, 50 mmol) at 5–10° C. The reaction was stirred for 1 hour at 0° C. following the addition step, then 1 hour at room temperature. The reaction was then poured into 400 ml ice water and extracted with diethyl ether (3×100 ml). The combined diethyl ether layers were extracted with 100 ml saturated $Na_2CO_3$ solution. The organic layer was dried over $Na_2SO_4$, and concentrated under vacuum. The residue was Kugelrohr distilled to yield (5-chlorothiophen-2-yl)-oxo-acetic acid ethyl ester as a yellow solid (9.32 g, 85%). $^1$H NMR (300 MHz, $CDCl_3$) δ7.96 (1H, d, J=4.2 Hz), 7.02 (1H, d, J=4.2 Hz), 4.41 (2H, q, J=7.1 Hz), 1.42 (3H, t, J=7.1 Hz).

Step 2: Preparation of (5-chlorothiophen-2-yl)-oxo-acetic acid (5-Chlorothiophen-2-yl)-oxo-acetic acid ethyl ester (8.62 g, 39.4 mmol) was dissolved in a mixture of 100 ml water and 100 ml methanol, then treated with 10 N NaOH (5.9 ml, 59 mmol) at room temperature for 20 hours. The reaction was then poured into 200 ml 3N HCl, and extracted with ethyl acetate (2×100 ml). The combined ethyl acetate extracts were dried over $Na_2SO_4$ and concentrated under vacuum to provide Preparation 1b (6.89 g, 92%). The product was then recrystallized from hexane/ether. MS (M−H)$^-$: 189.10; $^1$H NMR (300 MHz, $CDCl_3$) δ9.07 (1H, br s), 8.32 (1H, d, J=4.2 Hz), 7.10 (1H, d, J=4.2 Hz). IR (KBr) 3270, 3099, 1765, 1744, 1675, 1514, 1411, 1325 cm$^{-1}$.

Anal. Calcd. for $C_6H_3O_3SCl$: C, 37.81; H, 1.59. Found: C, 37.98; H, 1.73.

Preparation 1c

(5-Iodothiophen-2-yl)-oxo-acetic acid (IVa, $R^4$=$R^5$=H, $R^6$=I)

Step 1: Preparation of (5-iodothiophen-2-yl)-oxo-acetic acid ethyl ester

A solution of $AlCl_3$ (1.9 g, 14.28 mmol) in 5.3 ml nitromethane was added dropwise to a stirring mixture of ethyl oxalyl chloride (1.6 ml, 14.28 mmol) and 2-iodothiophene (1 g, 4.76 mmol) at 0–5° C. The reaction was stirred for 1 hour at 0° C. following the addition step, then 3 hours at room temperature. The reaction was then poured into 100 ml ice water and extracted with diethyl ether (3×50 ml). The combined diethyl ether layers were extracted with 50 ml saturated $NaHCO_3$ solution. The organic layer was then dried over $Na_2SO_4$, and concentrated under vacuum. The residue was purified by flash chromatography to provide (5-iodothiophen-2-yl)-oxo-acetic acid ethyl ester as an orange solid (0.34 g, 28%). MS (M+H)$^+$: 310.76; $^1$H NMR (300 MHz, DMSO-$d_6$) δ7.77 (1H, d, J=4.0 Hz), 7.59 (1H, d, J=4.0 Hz), 4.35 (2H, q, J=7.1 Hz), 1.32 (3H, t, J=7.1 Hz).

Step 2: Preparation of (5-iodothiophen-2-yl)-oxo-acetic acid (5-Iodothiophen-2-yl)-oxo-acetic acid ethyl ester (0.298 g, 0.96 mmol) was dissolved in 1,4 dioxane (4 ml) and 20% KOH (0.5 ml). The reaction mixture was stirred at ambient temperature for 4 hours then volatile solvent was removed by rotary evaporation. The residue was dissolved in 5 ml water and extracted with diethyl ether (35 ml). The aqueous layer was acidified to pH 3–4 with glacial acetic acid, and extracted with ethyl acetate (3×35 ml). The combined ethyl acetate extracts were dried over $Na_2SO_4$ and concentrated under vacuum to provide Preparation 1c (92 mg, 34%). MS (M−H)$^-$: 280.77; $^1$H NMR (300 MHz, DMSO-$d_6$) δ7.59 (1H, d, J=3.9 Hz), 7.50 (1H, d, J=4.0 Hz).

Preparation 1d

(4-Bromothiophen-2-yl)-oxo-acetic acid (IVa, $R^4$=$R^6$=H, $R^5$=Br)

Step 1: Preparation of 4-bromo-2-acetylthiophene

2-Acetylthiophene (21.6 ml, 0.20 mol) was dissolved in 200 ml $CHCl_3$ at 0° C. $AlCl_3$ (40 g, 0.30 mol) was added in small portions at such a rate as to maintain the temperature at 5–10° C. The reaction mixture was then cooled to 0° C. and bromine, $Br_2$ (11.34 ml, 0.22 mol) was added quickly. The reaction mixture was refluxed for two hours, then was allowed to cool and was poured into a mixture of 400 ml ice water and 50 ml concentrated HCl and stirred for 30 minutes. The organic layer was separated, dried over $Na_2SO_4$, and concentrated under vacuum. The crude product was distilled under vacuum to yield pure 4-bromo-2-acetylthiophene (27.6 g, 67%). MS (M–H)[−]: 204.85; $^1$H NMR (300 MHz, $CDCl_3$) δ7.58 (1H, d, J=1.3 Hz), 7.53 (1H, d, J=1.3 Hz), 2.55 (3H, s).

Step 2: Preparation of (4-bromothiophen-2-yl)-oxo-acetic acid

4-Bromo-2-acetylthiophene (14.35 g, 70.0 mmol) and $SeO_2$ were stirred in 50 ml pyridine at 70° C. for 3 hours. The reaction mixture was cooled and poured into 300 ml 1N HCl. This mixture was then extracted with diethyl ether (2×150 ml). The combined diethyl ether extracts were dried over $Na_2SO_4$ and concentrated under vacuum to provide Preparation 1d (15.24 g, 93%). The product thus obtained was then recrystallized twice from $CH_2Cl_2$. MS (M–H)[−]: 232.79; $^1$H NMR (300 MHz, DMSO-$d_6$) δ8.30 (1H, d, J=1.5 Hz), 8.05 (1H, d, J=1.5 Hz). $^{13}$C NMR (75 MHz, DMSO-$d_6$) δ177.46, 162.75, 139.39, 138.38, 135.67, 110.91.

Anal. Calcd. for $C_6H_3BrO_3S$: C, 30.66; H, 1.29. Found: C, 30.39; H, 1.30.

Preparation 1e (4-Chlorothiophen-2-yl)-oxo-acetic acid (IVa, $R^4$= $R^6$=H, $R^5$=Cl)

Step 1: Preparation of 4-chloro-2-acetylthiophene

2-Acetylthiophene (21.6 ml, 0.20 mol) was dissolved in chloroform (200 ml) at −10° C. $AlCl_3$ (54 g, 0.40 mole) was added in small portions at such a rate as to keep temperature below 5° C. A saturated solution of chlorine, $Cl_2$, in chloroform (100 ml) was then added dropwise at −10° C. over a period of 30 minutes. After the addition was completed, the reaction mixture was immediately poured into a mixture of 1 L ice water and 500 ml of 1 N HCl and stirred for 30 minutes. The organic layer was separated, dried over $Na_2SO_4$, and concentrated under vacuum to a yellow liquid. NMR analysis showed this to be a 3:1 mixture of 4-chloro-2-acetylthiophene and 4,5-dichloro-2-acetylthiophene. Partial purification was achieved by a Kugelrohr distillation, yielding 4-chloro-2-acetylthiophene (31 g, 83% pure, 80% yield). This material was used without further purification in the next step. $^1$H NMR (300 MHz, $CDCl_3$) δ7.53 (1H, d, J=1.2 Hz), 7.41 (1H, d, J=1.2 Hz), 2.54 (3H, s).

Step 2: Preparation of (4-chlorothiophen-2-yl)-oxo-acetic acid

The 4-chloro-2-acetylthiophene (product of Step 1, 161 mmol) was stirred with $SeO_2$ (26.85 g, 242 mmol) in pyridine (115 ml) at 70° C. for 3 hours. The reaction mixture was cooled and poured into 1 L 1N HCl. The resulting mixture was extracted with diethyl ether (3×300 ml). The combined diethyl ether extracts were dried over $Na_2SO_4$ and concentrated under vacuum. A portion of the crude product was purified in multiple runs by preparative HPLC on a YMC S5 ODS column (30×50 mm). A gradient of 50% eluant B to 100% eluant B at 45 ml/min. over 6 minutes was used (Eluant A: 10% methanol, 90% water, 0.1% TFA; Eluant B: 90% methanol, 10% water, 0.1% TFA). The desired fractions were pooled and concentrated under vacuum. (4-chlorothiophen-2-yl)-oxo-acetic acid, Preparation 1e was thus obtained (1.8 g). MS (M–H)[−]: 188.87; $^1$H NMR (300 MHz, DMSO-$d_6$) δ8.17 (1H, d, J=1.5 Hz), 7.99 (1H, d, J=1.5 Hz). $^{13}$C NMR (75 MHz, DMSO-$d_6$) δ177.64, 162.78, 138.65, 135.96, 133.13, 125.71.

Anal. Calcd. for $C_6H_3ClO_3S$: C, 37.81; H, 1.59. Found: C, 37.79; H, 1.49.

Preparation 1f (3-Bromothiophen-2-yl)-oxo-acetic acid (IVa, $R^5$= $R^6$=H, $R^4$=Br)

Step 1: Preparation of (3-bromothiophen-2-yl)-oxo-acetic acid ethyl ester

A solution of $AlCl_3$ (10 g, 75 mmol) in 20 ml of nitromethane was added dropwise to a stirring mixture of ethyl oxalyl chloride (8.4 ml, 75 mmol) and 3-bromothiophene (4.69 ml, 50 mmol) at 5–10° C. The reaction mixture was stirred for 1 hour at 0° C. following the addition step, then 1 hour at room temperature. The reaction mixture was then poured into 400 ml ice water and extracted with diethyl ether (3×100 ml). The combined diethyl ether layers were then extracted with saturated $Na_2CO_3$ solution (100 ml), then the organic layer was dried over $Na_2SO_4$, and concentrated under vacuum. The residue was Kugelrohr distilled to provide (3-bromothiophen-2-yl)-oxo-acetic acid ethyl ester as a yellow liquid (7.35 g, 56%). MS (DCl) (MH[+]): 264.68; $^1$H NMR (300 MHz, $CDCl_3$) δ7.72 (1H, d, J=5.2 Hz), 7.18 (1H, d, J=5.2 Hz), 4.44 (2H, q, J=7.2 Hz), 1.43 (3H, t, J=7.2 Hz).

Step 2: Preparation of (3-bromothiophen-2-yl)-oxo-acetic acid (3-Bromothiophen-2-yl)-oxo-acetic acid ethyl (5.26 g, 20 mmol) was dissolved in 100 ml of water and treated with 10 N NaOH (10 ml, 100 mmol) at room temperature for 20 hours. The reaction mixture was then acidified with 3N HCl, and extracted with ethyl acetate (3×50 ml). The combined ethyl acetate extracts were dried over $Na_2SO_4$ and concentrated under vacuum to provide (3-bromothiophen-2-yl)-oxo-acetic acid (4.51 g, 96%). MS (M–H)[−]: 235.00; $^1$H NMR (300 MHz, DMSO-$d_6$) δ8.22 (1H, d, J=5.1 Hz), 7.39 (1H, d, J=5.2 Hz).

Anal. Calcd. for $C_6H_3O_3SBr$: C, 30.66; H, 1.29. Found: C, 30.82; H, 1.47.

Preparation 1g (3-Chlorothiophen-2-yl)-oxo-acetic acid (IVa, $R^5$= $R^6$=H, $R^4$=Cl)

Step 1: Preparation of (3-chlorothiophen-2-yl)-oxo-acetic acid ethyl ester

A solution of $AlCl_3$ (8.6 g, 65 mmol) in 20 ml of nitromethane was added dropwise to a stirring mixture of ethyl oxalyl chloride (7.2 ml, 65 mmol) and 3-chlorothiophene (4.0 ml, 43 mmole) at 5–10° C. The reaction mixture was stirred for 1 hour at 0° C. following the addition step, then 1 hour at room temperature then was poured into 400 ml ice water. The resulting mixture was extracted with diethyl ether (3×100 ml). The combined diethyl ether layers were extracted with 100 ml saturated $Na_2CO_3$ solution. The organic layer was then dried over $Na_2SO_4$, and concentrated under vacuum. The residue was Kugelrohr distilled to yield pure (3-chlorothiophen-2-yl)-oxo-acetic acid ethyl ester (6.43 g, 68%). MS (M+H)[+]: 218.90; $^1$H NMR (300 MHz, $CDCl_3$) δ7.74 (1H, d, J=5.2 Hz), 7.09 (1H, d, J=5.2 Hz), 4.43 (2H, q, J=7.2 Hz), 1.42 (3H, t, J=7.2 Hz); IR (KBr) 3109, 2985, 1740, 1676, 1660, 1499, 1488, 1408, 1363, 1299 cm[−1].

Anal. Calcd. for $C_8H_7O_3SCl$: C, 43.95; H, 3.23. Found: C, 44.12; H, 3.21.

Step 2: Preparation of (3-chlorothiophen-2-yl)-oxo-acetic acid (3-Chlorothiophen-2-yl)-oxo-acetic acid ethyl ester (4.37 g, 20 mmol) was stirred in a mixture of 100 ml water and 10 N NaOH (10 ml, 100 mmol) at room temperature for 20 hours. The reaction was then acidified with 3N HCl, and extracted with ethyl acetate (3×50 ml). The combined ethyl acetate extracts were dried over $Na_2SO_4$ and concentrated under vacuum to provide (3-chlorothiophen-2-yl)-oxo-acetic acid (3.55 g, 93%). MS (M–H)$^-$: 188.96; $^1$H NMR (300 MHz, DMSO-d$_6$) δ14.20 (1H, br s), 8.25 (1H, d, J=5.2 Hz), 7.34 (1H, d, J=5.2 Hz); IR (KBr) 3098, 1740, 1727, 1645, 1485, 1396, 1364, 1249 cm$^{-1}$.

Anal. Calcd. for $C_6H_3O_3SCl$: C, 37.81; H, 1.59. Found: C, 37.79; H, 1.65.

Preparation 1h (3-Iodothiophen-2-yl)-oxo-acetic acid (IVa, R$^5$=R$^6$=H, R$^4$=I).

Step 1: Preparation of (3-iodothiophen-2-yl)-oxo-acetic acid ethyl ester

A solution of AlCl$_3$ (1.9 g, 14.3 mmol) in 5.3 ml of nitromethane was added dropwise to a stirring mixture of ethyl oxalyl chloride (1.6 ml, 14.3 mmol) and 3-iodothiophene (1 g, 4.8 mmol) at 0–5° C. The reaction mixture was stirred for 1 hour at 0° C. following the addition step, then 3 hours at room temperature then was poured into 100 ml ice water. The resulting mixture was extracted with diethyl ether (3×50 ml). The combined diethyl ether layers were extracted with 50 ml saturated NaHCO$_3$ solution, then the organic layer was dried over Na$_2$SO$_4$, and concentrated under vacuum. The residue was purified by flash chromatography to yield (3-iodothiophen-2-yl)-oxo-acetic acid ethyl ester as a yellow oil (0.64 g, 49%). MS (M+H)$^+$: 310.85; $^1$H NMR (300 MHz, DMSO-d$_6$) δ8.17 (1H, d, J=3.0 Hz), 7.51 (1H, d, J=3.0 Hz), 4.39 (2H, q, J=4.4 Hz), 1.35 (3H, t, J=4.2 Hz).

Step 2: Preparation of (3-iodothiophen-2-yl)-oxo-acetic acid (3-Iodothiophen-2-yl)-oxo-acetic acid ethyl ester (0.6 g, 1.93 mmol) was dissolved in 1,4 dioxane (6 ml) and 20% KOH (1 ml). The reaction mixture was stirred at ambient temperature for 4 hours then volatile solvent was removed by rotary evaporation. The residue was dissolved in 10 ml water and extracted with 35 ml of diethyl ether. The aqueous layer was acidified to pH 3–4 with glacial acetic acid, and extracted with ethyl acetate (3×35 ml). The combined ethyl acetate extracts were dried over Na$_2$SO$_4$ and concentrated under vacuum to provide (3-iodothiophen-2-yl)-oxo-acetic acid (107 mg, 20%). MS (M+H)$^+$: 310.85; $^1$H NMR (300 MHz, DMSO-d$_6$) δ8.17 (1H, d, J=3.0 Hz), 7.51 (1H, d, J=3.0 Hz), 4.39 (2H, q, J=4.4 Hz), 1.35 (3H, t, J=4.2 Hz).

Preparation 1i (4,5-Dibromothiophen-2-yl)-oxo-acetic acid (IVa, R$^5$=R$^6$=Br, R$^4$=H)

Step 1: Preparation of (4,5-dibromothiophen-2-yl)-oxo-acetic acid ethyl ester

A solution of AlCl$_3$ (8.18 g, 61.4 mmol) in 20 ml of nitromethane was added dropwise to a stirring mixture of ethyl oxalyl chloride (6.9 ml, 61.4 mmol) and 2,3-dibromothiophene (9.90 g, 40.9 mmol) at −5–0° C. The reaction mixture was stirred for 0.5 hour at −5° C. following the addition step, then 2 hours at room temperature then was poured into 400 ml ice water and extracted with diethyl ether (150 ml). The diethyl ether layer was extracted with 100 ml saturated NaHCO$_3$ solution, dried over Na$_2$SO$_4$, and concentrated under vacuum. The residue was partially purified by flash chromatography on silica gel 60 with hexane/ethyl acetate 9:1. The resulting product was then recrystallized from diethyl ether to yield (4,5-dibromothiophen-2-yl)-oxo-acetic acid ethyl ester (3.55 g, 25%). MS (M+H)$^+$: 342.70; $^1$H NMR (300 MHz, CDCl$_3$) δ7.97 (1H, s), 4.44 (2H, q, J=7.1 Hz), 1.44 (3H, t, J=7.1 Hz).

Anal. Calcd. for $C_8H_6O_3SBr_2$: C, 28.10; H, 1.77. Found: C, 28.05; H, 1.72.

Step 2: Preparation of (4,5-dibromothiophen-2-yl)-oxo-acetic acid (4,5-Dibromothiophen-2-yl)-oxo-acetic acid ethyl ester (1.00 g, 2.92 mmol) was stirred in a mixture of 5 ml water and 1 N NaOH (3.65 ml, 3.65 mmol) at room temperature for 2 hours. The reaction was then poured into 2 N acetic acid, and extracted into 100 ml ethyl acetate. The ethyl acetate layer was dried over Na$_2$SO$_4$ and concentrated under vacuum to provide (4,5-dibromothiophen-2-yl)-oxo-acetic acid (788 mg, 86%). MS (M–H)$^-$: 312.73; $^1$H NMR (300 MHz, DMSO-d$_6$) δ7.98 (s).

Anal. Calcd. for $C_6H_2O_3SBr_2$: C, 22.95; H, 0.64. Found: C, 22.64; H, 0.94.

Preparation 1j (4.5-Dichlorothiophen-2-yl)-oxo-acetic acid (IVa, R$^5$=R$^6$=Cl, R$^4$=H)

Step 1: Preparation of (4,5-dichlorothiophen-2-yl)-oxo-acetic acid ethyl ester

A solution of AlCl$_3$ (10.0 g, 75 mmol) in 20 ml of nitromethane was added dropwise to a stirring mixture of ethyl oxalyl chloride (8.4 ml, 75 mmol) and 2,3-dichlorothiophene (7.65 g, 50 mmol) at −5–0° C. The reaction mixture was stirred for 0.5 hour at −5° C. following the addition step, then 2 hours at room temperature. The reaction was then poured into 400 ml ice water and extracted with 150 ml of diethyl ether. The diethyl ether layer was then extracted with 100 ml saturated NaHCO$_3$ solution, dried over Na$_2$SO$_4$, and concentrated under vacuum to yield pure (4,5-dichlorothiophen-2-yl)-oxo-acetic acid ethyl ester (9.61 g, 76%). MS (M+H)$^+$: 252.80; $^1$H NMR (300 MHz, CDCl$_3$) δ7.97 (1H, s), 4.43 (2H, q, J=7.1 Hz), 1.44 (3H, t, J=7.1 Hz).

Anal. Calcd. for $C_8H_6O_3SCl_2$: C, 37.96; H, 2.39. Found: C, 38.22; H, 2.36.

Step 2: Preparation of (4,5-dichlorothiophen-2-yl)-oxo-acetic acid

A solution of (4,5-dichlorothiophen-2-yl)-oxo-acetic acid ethyl ester (2.53 g, 10.0 mmol) in acetone (15 ml), water (5 ml), and conc. HCl (20 ml) was stirred under reflux for 2 hr. The reaction mixture was then allowed to cool to ambient temperature and was poured into CH$_2$Cl$_2$ and water. The organic layer was dried over Na$_2$SO$_4$ and concentrated under vacuum. Crystallization of the residue from dichloromethane provided pure (4,5-dichlorothiophen-2-yl)-oxo-acetic acid as a yellow solid (557 mg, 25%). MS (M–H)$^-$: 222.78; $^1$H NMR (300 MHz, DMSO-d$_6$) δ8.06 (s).

Anal. Calcd. for $C_6H_2O_3SCl_2 \cdot 1.0H_2O$: C, 29.65; H, 1.66. Found: C, 29.70; H, 1.41.

Preparation 1k (4-Bromo-5-chlorothiophen-2-yl)-oxo-acetic acid (IVa, R$^5$=Br, R$^6$=Cl, R$^4$=H)

Step 1: Preparation of (4-bromo-5-chlorothiophen-2-yl)-oxo-acetic acid ethyl ester A solution of AlCl$_3$ (10 g, 75 mmol) in 20 ml of nitromethane was added dropwise to a stirring mixture of ethyl oxalyl chloride (8.4 ml, 75 mmol) and 3-bromo-2- chlorothiophene (9.87 g, 50 mmol) at −5–0° C. The reaction mixture was stirred for 45 minutes at 0° C. following the addition step, then 3 hours at room temperature. The reaction mixture was then poured into 400 ml ice water and extracted with 200 ml ethyl acetate/200 ml diethyl ether. The organic layer was extracted with 1 L saturated $NaHCO_3$ solution, dried over $Na_2SO_4$, and concentrated under vacuum. The residue was purified by flash chromatography on silica gel 60 with hexane/ethyl acetate 9:1 to yield pure (4-bromo-5-chlorothiophen-2-yl)-oxo-acetic acid ethyl ester (6.04 g, 41%). MS $(M+H)^+$: 298.83; $^1H$ NMR (300 MHz, $CDCl_3$) δ8.00 (1H, s), 4.43 (2H, q, J=7.1 Hz), 1.43 (3H, t, J=7.1 Hz). $^{13}C$ NMR (75 MHz, $CDCl_3$) δ173.74, 160.21, 138.42, 137.95, 135.78, 113.03, 63.09, 13.98.

Anal. Calcd. for $C_8H_6BrClO_3S$: C, 32.29; H, 2.03. Found: C, 32.24; H, 1.75.

Step 2: Preparation of (4-bromo-5-chlorothiophen-2-yl)-oxo-acetic acid (4-Bromo-5-chlorothiophen-2-yl)-oxo-acetic acid ethyl ester (1.03 g, 3.47 mmol) was sonicated in a mixture of 5 ml water and 1 N NaOH (4.34 ml, 4.34 mmol) at room temperature for 2 hours. The reaction mixture was then poured into 2 N acetic acid, and extracted into 100 ml ethyl acetate. The ethyl acetate layer was separated and extracted twice with 150 ml saturated $Na_2CO_3$ solution. The aqueous layer was carefully acidified to pH 3 with 3 N HCl, then extracted with 150 ml ethyl acetate. The organic layer was dried over $Na_2SO_4$ and concentrated under vacuum to provide (4-bromo-5-chlorothiophen-2-yl)-oxo-acetic (389 mg, 40%). MS $(M-H)^-$: 268.82; $^1H$ NMR (300 MHz, $CDCl_3$) δ8.10 (1H, s).

Anal. Calcd. for $C_6H_2BrClO_3S·1.0 H_2O$: C, 25.07; H, 1.40. Found: C, 25.34; H, 1.45.

Preparation 1l (3,4-Dibromothiophen-2-yl)-oxo-acetic acid (IVa, $R^4=R^5=Br, R^6=H$)

Step 1: Preparation of (3,4-dibromothiophen-2-yl)-oxo-acetic acid ethyl ester

A solution of $AlCl_3$ (7.3 g, 55 mmol) in 15 ml of nitromethane was added dropwise to a stirred mixture of ethyl oxalyl chloride (6.2 ml, 55 mmol) and 3,4-dibromothiophene (8.83 g, 37 mmol) at 5–10° C. The reaction mixture was stirred for 45 minutes at 0° C. following the addition step, then 1 hour at room temperature. The reaction mixture was then poured into 400 ml ice water and extracted with diethyl ether (3×100 ml). The combined diethyl ether layers were extracted with 100 ml saturated $Na_2CO_3$ solution, then the organic layer was dried over $Na_2SO_4$, and concentrated under vacuum. The residue was Kugelrohr distilled to yield pure (3,4-dibromothiophen-2-yl)-oxo-acetic acid ethyl ester (8.25 g, 66%). m.p. 71° C.; MS (M+H)–: 340.84; $^1H$ NMR (300 MHz, $CDCl_3$) δ7.79 (1H, s), 4.45 (2H, q, J=7.1 Hz), 1.44 (3H, t, J=7.1 Hz).

Step 2: Preparation of (3,4-dibromothiophen-2-yl)-oxo-acetic acid (3,4-Dibromothiophen-2-yl)-oxo-acetic acid ethyl ester (6.84 g, 20 mmol) was stirred in a mixture of 100 ml water and 10 N NaOH (10 ml, 100 mmol) at room temperature for 20 hours. The reaction mixture was then acidified with 3N HCl, and extracted with ethyl acetate (3×50 ml). The combined ethyl acetate extracts were dried over $Na_2SO_4$ and concentrated under vacuum to yield (3,4-dibromothiophen-2-yl)-oxo-acetic acid (3.15 g, 50%). MS $(M-H)^-$: 312.74; $^1H$ NMR (300 MHz, DMSO-$d_6$) δ8.45 (1H, s).

Anal. Calcd. for $C_6H_2Br_2O_3S·0.5 H_2O$: C, 22.31; H, 0.94. Found: C, 22.27; H, 0.99.

Preparation 1m (3,4-Dichlorothiophen-2-yl)-oxo-acetic acid (IVa, $R^4=R^5=Cl, R^6=H$)

Step 1: Preparation of 3,4-dichlorothiophene

To tetrachlorothiophene (10.0 g, 45.1 mmol) in an oven dried 100 mL flask, evacuated and flushed with nitrogen, was added anhydrous diethyl ether (60 ml). The resulting solution was cooled to −18° C., then n-butyllithium (1.6 M in hexane) (56 ml, 90 mmol) was added dropwise via a syringe. After stirring for 1 hr at −18° C., the reaction was allowed to warm to ambient temperature and stirred further for 30 min. The reaction was quenched with 1N HCl. The organic layer was separated, dried over $Na_2SO_4$ and concentrated under vacuum. The crude material, 3,4-dichlorothiophene (6.12 g) was used directly in the next step without further purification.

Step 2: Preparation of (3,4-dichlorothiophen-2-yl)-oxo-acetic acid ethyl ester

Aluminum trichloride (16.2 g, 121.6 mmol) in nitromethane (40 ml) was added dropwise via an addition funnel to a stirring solution of 3,4-dichlorothiophene (6.1 g, 40.5 mmol) and ethyl oxalyl chloride (13.6 ml, 121.6 mmol) at −5° C. under nitrogen. The reaction mixture was stirred at 0° C. for 1 hour, and at ambient temperature for 3 hours, then was poured into ice water (300 ml), and extracted with diethyl ether (200 ml). The organic layer was separated, washed with saturated $NaHCO_3$, dried over $Na_2SO_4$ and concentrated under vacuum. Purification was performed by column chromatography using hexane/ethyl acetate (20:1) to yield (3,4-dichlorothiophen-2-yl)-oxo-acetic acid ethyl ester as a light yellow solid (4.89 g, 48%). MS $(M+H)^+$: 253.03; $^1H$ NMR (300 MHz, DMSO-$d_6$) δ8.43 (1H, s), 4.37 (2H, q, J=7.1 Hz), 1.32 (3H, t, J=7.1 Hz). $^{13}C$ NMR (75 MHz, $CDCl_3$) δ175.55, 162.12, 130.38, 130.24, 129.83, 128.13, 63.48, 14.13.

Step 3: Preparation of (3,4-dichlorothiophen-2-yl)-oxo-acetic acid

A solution of yield (3,4-dichlorothiophen-2-yl)-oxo-acetic acid ethyl ester (0.42 g, 1.66 mmol) in acetone (10 ml), water (2 ml), and conc. HCl (10 ml) was stirred under reflux for 1 hour. The reaction mixture was allowed to cool to ambient temperature then was concentrated in vacuo to provide a crude oil. The crude oil was purified by preparative HPLC to provide pure (3,4-dichlorothiophen-2-yl)-oxo-acetic acid as a yellow solid (85 mg, 38%). MS $(M-H)^-$: 222.80; $^1H$ NMR (300 MHz, DMSO-$d_6$) δ8.38 (1H, s). $^{13}C$ NMR (75 MHz, $CDCl_3$) δ173.14, 159.44, 136.57, 133.43, 128.97, 125.20.

Preparation 1n (3,5-Dibromothiophen-2-yl)-oxo-acetic acid (IVa, $R^4=R^6=Br, R^5=H$)

Step 1: Preparation of (3,5-dibromothiophen-2-yl)-oxo-acetic acid ethyl ester

A solution of $AlCl_3$ (5.0 g, 37.5 mmol) in 10 ml of nitromethane was added dropwise to a stirred mixture of ethyl oxalyl chloride (4.2 ml, 37.5 mmol) and 2,4-dibromothiophene (6.05 g, 25 mmol) at −5–0° C. The reaction mixture was stirred for 45 minutes at 0° C. following the addition step, then 3 hours at room temperature. The reaction mixture was then poured into 400 ml ice water and extracted with 200 ml ethyl acetate/200 ml ether. The organic layer was extracted with 1 L saturated $NaHCO_3$ solution, dried over $Na_2SO_4$, and concentrated under vacuum to yield pure (3,5-dibromothiophen-2-yl)-oxo-acetic acid ethyl ester (6.20 g, 73%). MS $(M+H)^+$: 342.71;

¹H NMR (300 MHz, CDCl₃) δ7.18 (1H, s), 4.42 (2H, q, J=7.1 Hz), 1.42 (3H, t, J=7.1 Hz).

Anal. Calcd. for C₈H₆Br₂O3S: C, 28.10; H, 1.77. Found: C, 28.01; H, 1.89.

Step 1: Preparation of (3,5-dibromothiophen-2-yl)-oxo-acetic acid (3,5-Dibromothiophen-2-yl)-oxo-acetic acid ethyl ester (513 mg, 1.50 mmol) was dissolved in 25 ml acetone and treated with 15 ml 8 N HCl at reflux for a total of 4 hours. The reaction mixture was concentrated in vacuo, poured into 50 ml water, and extracted into 100 ml of dichloromethane. The organic layer was dried over Na₂SO₄ and concentrated in vacuo to yield (3,5-dibromothiophen-2-yl)-oxo-acetic acid (467 mg, 99%). MS (M+H)⁺: 314.84; ¹H NMR (300 MHz, DMSO-d₆) δ7.64 (1H, s).

Preparation 1o (3,4,5-Tribromothiophen-2-yl)-oxo-acetic acid (IVa, R⁴=R⁵=R⁶=Br)

Step 1: Preparation of (3,4,5-tribromothiophen-2-yl)-oxo-acetic acid ethyl ester To tetrabromothiophene (2.0 g, 5.0 mmol) in an oven dried 50 mL flask, evacuated and flushed with nitrogen, was added anhydrous diethyl ether (12 ml). The resulting solution was cooled to −18° C., then n-butyllithium (1.6 M in hexane) (3.1 ml, 5.0 mmol ) was added dropwise via a syringe. After stirring for 10 min at −18° C., diethyl oxalate (0.75 ml, 5.5 mmol) was added dropwise. Stirring was continued for 30 min, then the reaction mixture was quenched with 1N HCl. The organic layer was separated, dried over Na₂SO₄ and concentrated under vacuum. Purification was performed by column chromatography using hexane/ethyl acetate (20:1) to yield (3,4,5-tribromothiophen-2-yl)-oxo-acetic acid ethyl ester as a yellow solid (1.5 g, 71%). MS (M+H)⁺: 422.55; ¹H NMR (300 MHz, CDCl₃) δ4.45 (2H, q, J=7.1 Hz), 1.44 (3H, t, J=7.1 Hz). ¹³C NMR (75 MHz, CDCl₃) δ173.89, 161.64, 133.35, 124.81, 123.05, 122.54, 63.75, 14.11.

Step 1: Preparation of (3,4,5-Tribromothiophen-2-yl)-oxo-acetic acid

A solution of (3,4,5-tribromothiophen-2-yl)-oxo-acetic acid ethyl ester (0.4 g, 0.95 mmol) in acetone (10 ml), water (2 ml), and conc. HCl (8 ml) was stirred under reflux for 1.5 hours. The reaction mixture was allowed to cool to ambient temperature and concentrated in vacuo to remove acetone which gave rise to solids which were collected, washed with water and dried. (3,4,5-tribromothiophen-2-yl)-oxo-acetic acid was thus obtained as a light yellow solid (0.17 g, 49%). MS (M−H)⁻: 392.75; ¹³C NMR (75 MHz, CDCl₃) δ124.19, 117.80, 113.26, 111.72. IR (KBr) cm⁻¹ 3477.9, 3107.1, 2922.5, 1715.9, 1681.5, 1666.0, 1484.5, 1306.5, 1268.9.

Preparation 1p (3,4,5-Trichlorothiophen-2-yl)-oxo-acetic acid (IVa, R⁴=R⁵=R⁶=Cl)

Step 1: Preparation of (3,4,5-trichlorothiophen-2-yl)-oxo-acetic acid ethyl ester To tetrachlorothiophene (2.0 g, 9.0 mmol) in an oven dried 50 mL flask, evacuated and flushed with nitrogen, was added anhydrous diethyl ether (12 ml). The resulting solution was cooled to −18° C., then n-butyllithium (1.6 M in hexane) (5.6 ml, 9.0 mmol) was added dropwise via a syringe. After stirring for 10 min at −18° C., diethyl oxalate (1.4 ml, 9.9 mmol) was added dropwise. Stirring was continued for 30 min, then the reaction mixture was quenched with 1N HCl. The organic layer was separated, dried over Na₂SO₄ and concentrated under vacuum. Purification was performed by column chromatography using hexane/ethyl acetate (20:1) to provide (3,4,5-trichlorothiophen-2-yl)-oxo-acetic acid ethyl ester as a yellow solid (0.93 g, 47%). MS (M+H)⁺: 288.92; ¹H NMR (300 MHz, CDCl₃) δ4.44 (2H, q, J=7.1 Hz), 1.43 (3H, t, J=7.1 Hz). ¹³C NMR (75 MHz, CDCl₃) δ173.72, 161.82, 136.83, 133.16, 127.30, 126.53, 63.76, 14.11.

Step 2: Preparation of (3,4,5-trichlorothiophen-2-yl)-oxo-acetic acid

A solution of (3,4,5-trichlorothiophen-2-yl)-oxo-acetic acid ethyl ester (0.25 g, 0.86 mmol) in acetone (6 ml), water (2 ml), and conc. HCl (6 ml) was stirred under reflux for 1.5 hours. The reaction mixture was allowed to cool to ambient temperature then evaporation of acetone gave rise to solids which were collected, washed with water and dried. (3,4,5-trichlorothiophen-2-yl)-oxo-acetic acid was thus obtained as a light yellow solid (99 mg, 50%). MS (M−H)⁻: 258.74; ¹³C NMR (75 MHz, DMSO-d₆) δ174.16, 162.74, 134.73, 130.43, 125.92, 125.26. IR (KBr) cm⁻¹ 3547.5, 2855.3, 2515.5, 1924.8, 1716.3, 1667.1, 1405.7, 1339.7, 1305.4

Preparation 1q (4-Bromo-5-methylthiophen-2-yl)-oxo-acetic acid (IVa, R⁴=H, R⁵=Br, R⁶=CH₃)

Step 1: Preparation of (5-methylthiophen-2-yl)-oxo-acetic acid ethyl ester

A solution of AlCl₃ (10 g, 75 mmol) in 20 ml of nitromethane was added dropwise to a stirred mixture of ethyl oxalyl chloride (8.4 ml, 75 mmol) and 2-methylthiophene (4.84 ml, 50 mmol) at −5–0° C. The reaction mixture was stirred for 45 minutes at 0° C. following the addition step, then 18 hours at room temperature. The reaction mixture was then poured into 100 ml ice water and was extracted with diethyl ether (3×75 ml). The combined organic layer was extracted with 100 mL saturated NaHCO₃ solution, then the organic layer was dried over Na₂SO₄, and concentrated under vacuum. The residue was Kugelrohr distilled to yield (5-methylthiophen-2-yl)-oxo-acetic acid ethyl ester (3.51 g, 35%). MS (M+H)⁺: 199.18; ¹H NMR (300 MHz, CDCl₃) δ7.95 (1H, d, J=3.9 Hz), 6.87 (1H, d, J=3.9 Hz), 4.40 (2H, q, J=8.4 Hz), 2.58 (3H, s), 1.41 (3H, t, J=7.1 Hz).

Anal. Calcd. for C₉H₁₀O₃S: C, 54.53; H, 5.08. Found: C, 54.47; H, 5.16.

Step 2: Preparation of (5-methylthiophen-2-yl)-oxo-acetic acid

A solution of (5-methylthiophen-2-yl)-oxo-acetic acid ethyl ester (5.5 g, 28 mmol) in THF (20 ml), water (20 ml), and 50% NaOH (4 ml) was stirred under reflux for 18 hours. The reaction mixture was allowed to cool to ambient temperature. After partial evaporation, the reaction mixture was acidified with 1N HCl and extracted with diethyl ether (2×50 ml). The organic layer was dried over sodium sulfate and concentrated under vacuum to yield (5-methylthiophen-2-yl)-oxo-acetic acid (4.8 g, 100%). ¹H NMR (300 MHz, CDCl₃) δ8.40 (1H, d, J=4.0 Hz), 6.95 (1H, d, J=3.9 Hz), 2.63 (3H, s).

Step 3: Preparation of (4-bromo-5-methylthiophen-2-yl)-oxo-acetic acid

Br₂ (0.665 mL, 12.9 mmol) was added dropwise to a solution of (5-methylthiophen-2-yl)-oxo-acetic acid (1.05 g, 6.15 mmol) and sodium acetate (757 mg, 9.23 mmol) in 10 ml of glacial acetic acid and stirred at room temperature for 6.5 hours. The reaction mixture was poured into 150 ml water and extracted with diethyl ether (2×75 ml). The combined diethyl ether layers were extracted with aqueous Na₂S₂O₃, the organic layer was then dried over sodium sulfate, and concentrated under vacuum to provide crude (4-bromo-5-methylthiophen-2-yl)-oxo-acetic acid (1.40 g, 91%). ¹H NMR (300 MHz, CDCl₃) δ8.35 (1H, s), 2.54 (3H, s).

Preparations 1r and 1s

Preparations 1r and 1s, IVb were prepared as described below.

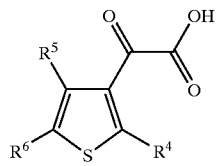

IVb

Preparation 1r (2,5-Dibromothiophen-3-yl)-oxo-acetic acid (IVb, R⁴=R⁶=Br, R⁵=H)

Step 1: Preparation of (2,5-dibromothiophen-3-yl)-oxo-acetic acid ethyl ester

A solution of AlCl₃ (10 g, 75 mmol) in 20 ml of nitromethane was added dropwise to a stirred mixture of ethyl oxalyl chloride (8.4 ml, 75 mmol) and 2,5-dibromothiophene (12.10 g, 50 mmol) at −5–0° C. The reaction mixture was stirred for 6 hours at room temperature then was poured into 250 ml ice water and extracted with ethyl acetate (2×150 ml). The combined organic layer was extracted with 150 ml saturated NaHCO₃ solution, then the organic layer was dried over Na₂SO₄, and concentrated under vacuum. The residue was purified by flash chromatography on silica gel 60 with hexane/ethyl acetate 20:1 to yield pure (2,5-dibromothiophen-3-yl)-oxo-acetic acid ethyl ester (4.77 g, 28%). MS (M+H)⁺: 343.05; ¹H NMR (300 MHz, DMSO-d₆) δ7.50 (1H, s), 4.43 (2H, q, J=7.1 Hz), 1.42 (3H, t, J=7.1 Hz).

Anal. Calcd. for C₈H₆Br₂O₃S: C, 28.10; H, 1.77. Found: C, 28.28; H, 1.73.

Step 2: Preparation of (2,5-dibromothiophen-3-yl)-oxo-acetic acid (2,5-Dibromothiophen-3-yl)-oxo-acetic acid ethyl ester (1.71 g, 5.0 mmol) was dissolved in 15 ml acetone and 2 ml water, then treated with 15 ml concentrated HCl at reflux for 2 hours. The reaction mixture was then poured into 100 ml water, and extracted into 100 ml of dichloromethane. The organic layer was dried over Na₂SO₄ and concentrated under vacuum to yield crude (2,5-dibromothiophen-3-yl)-oxo-acetic acid which was used without further purification.

Preparation 1s (2,5-Dichlorothiophen-3-yl)-oxo-acetic acid (IVb, R⁴=R =Cl, R⁵=H)

Step 1: Preparation of (2,5-dichlorothiophen-3-yl)-oxo-acetic acid ethyl ester

A solution of AlCl₃ (10 g, 75 mmol) in 20 ml of nitromethane was added dropwise to a stirring mixture of ethyl oxalyl chloride (8.4 ml, 75 mmol) and 2,5-dichlorothiophene (7.65 ml, 50 mmol) at 5–10° C. The reaction mixture was stirred for 1 hour at 0° C. following the addition step, then 1 hour at room temperature. The reaction mixture was then poured into 400 ml ice water and extracted with diethyl ether (3×100 ml). The combined diethyl ether layers were extracted with 100 ml saturated Na₂CO₃ solution, then the organic layer was dried over Na₂SO₄, and concentrated under vacuum. The residue was Kugelrohr distilled to provide (2,5-dichlorothiophen-3-yl)-oxo-acetic acid ethyl ester as a yellow liquid (5.32 g, 42%). MS (M+H)⁺: 252.97; ¹H NMR (300 MHz, CDCl₃) δ7.32 (1H, s), 4.39 (2H, q, J=7.1 Hz), 1.40 (3H, t, J=7.1 Hz).

Step 1: Preparation of (2,5-dichlorothiophen-3-yl)-oxo-acetic acid (2,5-Dichlorothiophen-3-yl)-oxo-acetic acid ethyl ester (4.51 g, 17.8 mmol) was stirred in a mixture of 100 ml water and 10 N NaOH (10 ml, 100 mmol) at room temperature for 20 hours. The reaction mixture was then acidified with 3N HCl, and extracted with ethyl acetate (3×50 ml). The combined ethyl acetate extracts were dried over Na₂SO₄ and concentrated under vacuum to provide (2,5-dichlorothiophen-3-yl)-oxo-acetic acid (3.90 g, 97%). MS (M−H)⁻: 223.02; ¹H NMR (300 MHz, DMSO-d₆) δ7.54 (s).

Anal. Calcd. for C₆H₂Cl₂O₃S: C, 32.02; H, 0.90. Found: C, 32.15; H, 1.00.

Preparation 2

Preparation of (5-chloro-2-methoxyphenyl) hydrazine

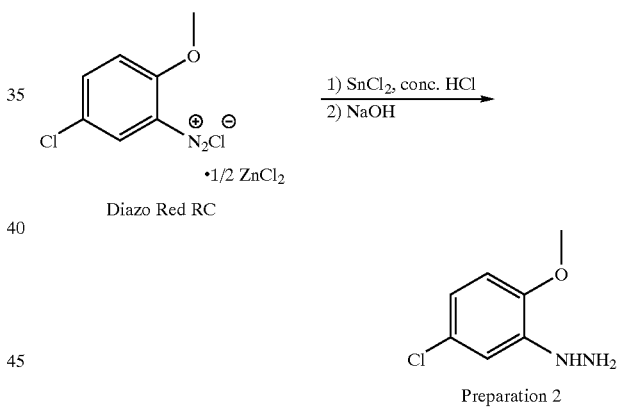

Preparation 2

Tin(II)chloride dihydrate (SnCl₂.2H₂O, 121 g, 0.54 mol) was dissolved in 300 ml concentrated HCl at −72° C. Diazo Red RC (Azoic Diazo No. 10, C.I. 37120, Fast Red RC Salt, Aldrich Chemical Co., 50 g, 0.18 mole) was added in portions with vigorous mechanical stirring. After the addition was complete, the reaction was stirred at 0° C. for three hours. The tan solid was filtered and washed with concentrated HCl, then stirred for 30 minutes in a mixture of 500 ml of dichloromethane and 500 ml 2N NaOH. The organic layer was separated, dried over sodium sulfate, concentrated under vacuum, and the resulting oil crystallized from 100 ml of diethyl ether to yield (5-chloro-2-methoxyphenyl) hydrazine (26.4 g, 84%). ¹H NMR (300 MHz, CDCl₃) δ6.96 (1H, d, J=2.4 Hz), 6.70 (1H, dd, 8.4, 2.4 Hz), 6.65 (1H, d, J=8.4 Hz), 3.81 (3H, s).

Anal. Calcd. for C₇H₉N₂OCl: C, 48.71; H, 5.26; N, 16.23. Found: C, 48.67; H, 5.39; N, 16.20.

Preparations 2a–2i, (III)

Preparations 2a–2i (III) were prepared from the corresponding appropriately substituted 2-methoxyaniline derivative (V) as depicted below and according to the following general procedure.

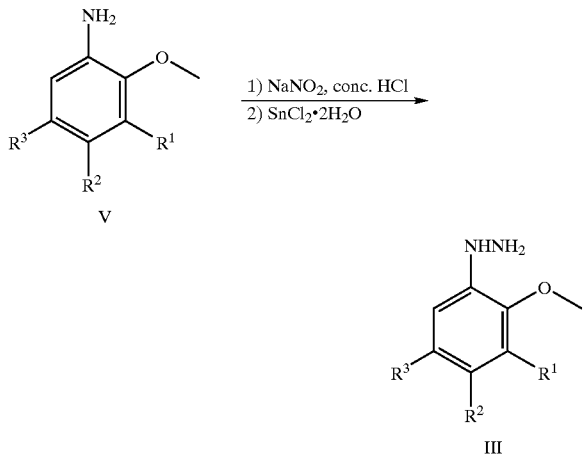

General Procedure for Preparations 2a–2i (III)

A suspension of the appropriately substituted 2-methoxyaniline derivative (of formula V prepared as described below) (80 mmol) in 300 ml concentrated HCl was cooled to −10° C. With mechanical stirring, a solution of sodium nitrite (7.18 g, 104 mmol) in 30 ml water was added slowly via pipette, maintaining the reaction mixture temperature at −10° C. The tip of the addition pipette was kept below the surface of the reaction mixture during the addition. The reaction mixture was warmed to 0° C. and stirred for 1 hour. The reaction mixture was then cooled to −35° C., and a solution of Tin(II)chloride dihydrate ($SnCl_2.2H_2O$, 46.93 g, 208 mmol) in 50 ml concentrated HCl was added slowly, maintaining the reaction mixture temperature at −35° C. The reaction mixture was warmed to 0° C. and stirred for 1 hour. The solid product was collected by filtration and washed with concentrated HCl and water. The solid was then stirred in a mixture of 600 ml ethyl acetate and 1000 ml 3N NaOH for 1 hour. The organic layer was separated, dried over sodium sulfate, and concentrated to dryness under vacuum to provide Preparation 2a–2i, II.

Preparation 2a (3-Allyl-5-chloro-2-methoxyphenyl)hydrazine (III, $R^1=CH_2CH=CH_2$, $R^2=H$, $R^3=Cl$)

Step 1: Preparation of 2-nitro-4-chloro-6-allylphenol

A mixture of 4-chloro-2-nitrophenol (100 g), allyl bromide (69.7 g), and potassium carbonate (95.5 g) in acetone (1 L) was refluxed for 6 hours. After cooling to room temperature and filtration, the filtrate was concentrated to give a residue. The residue was extracted with dichloromethane. The organic layer was washed with water, dried over $MgSO_4$, and concentrated in vacuo to give a crude product (110.9 g, 90%) which was used in the next step without purification. 42 g of the crude product was heated at 180° C. for 8 hours. Purification by flash chromatography over silica gel (elution with 50% ethyl acetate in hexanes) gave 22 g (50%) of 2-nitro-4-chloro-6-allylphenol. $^1$H NMR (300 MHz, $CDCl_3$) δ8.00 (d, J=2.6 Hz, 1 H), 7.44 (d, J=2.6 Hz, 1 H), 6.00–5.89 (m, 1 H), 5.20–5.12 (m, 2 H), 3.48 (d, J=6.69 Hz, 2 H).

Step 2: Preparation of 2-nitro-4-chloro-6-allylanisole

A mixture of 2-nitro-4-chloro-6-allylphenol (21.7 g), methyl iodide (28.28 g), and potassium carbonate (16.6 g) in acetone (300 ml) was refluxed for 16 hours. After cooling to room temperature and filtration, the filtrate was concentrated in vacuo to give a residue. The residue was extracted with dichloromethane. The organic layer was washed with water, dried over $MgSO_4$, and concentrated to give crude 2-nitro-4-chloro-6-allylanisole (21.6 g, 96%) which was used in the next step without purification. $^1$H NMR (300 MHz, $CDCl_3$) δ7.69 (d, J=2.6 Hz, 1 H), 7.41 (d, J=2.6 Hz, 1 H), 5.97–5.89 (m, 1 H), 5.20–5.10 (m, 2 H), 3.88 (s, 3 H), 3.48 (d, J=6.65 Hz, 2 H).

Step 3: Preparation of 2-amino-4-chloro-6-allylanisole (V, $R^1=CH_2CH=CH_2$, $R^2=H$, $R^3=Cl$)

Concentrated HCl (25 ml) was added to a mixture of 2-nitro-4-chloro-6-allylanisole (11.25 g) and granulated tin (9.02 g). The resulting mixture was stirred for 1 hour with heating at a boiling water bath temperature. The reaction mixture was then cooled to 0° C. and was made basic by addition of 10 N NaOH. The resulting mixture was extracted with dichloromethane. The organic layer was washed with water, dried over $MgSO_4$, and concentrated in vacuo to give crude 2-amino-4-chloro-6-allylanisole (9.34 g, 95%) which was used in the next step without purification. $^1$H NMR (300 MHz, $CDCl_3$) δ6.61 (d, J=2.5 Hz, 1 H), 6.55 (d, J=2.5 Hz, 1 H), 5.98–5.89 (m, 1 H), 5.13–5.06 (m, 2 H), 3.72 (s, 3 H), 3.36 (d, J=6.5 Hz, 2 H).

Step 4: Preparation of (3-allyl-5-chloro-2-methoxyphenyl)hydrazine

The title compound was prepared by the general procedure described above for Preparations 2a–i using 2-amino-4-chloro-6-allylanisole (18 g), $NaNO_2$ (9.02 g), and $SnCl_2.2H_2O$ (3.48 g). Workup gave 16 g (82%) of (3-allyl-5-chloro-2-methoxyphenyl)hydrazine which was used without further purification.

Preparation 2b (3-Bromo-5-chloro-2-methoxyphenyl)hydrazine (III, $R^1=Br$, $R^2=H$, $R^3=Cl$)

Step 1: Preparation of 2-nitro-4-chloro-6-bromophenol

Bromine, $Br_2$ (63.9 g) in 50 ml of dichloromethane was added dropwise to a solution of 4-chloro-6-nitrophenol (34.7 g) in 300 ml of dichloromethane. After the addition was completed, the mixture was stirred at room temperature for 30 min. Pyridine (19.0 g, 240 mmol) in 50 ml of dichloromethane was added. This mixture was stirred at room temperature for 2 hours and a white precipitate was formed. The reaction mixture was quenched with 200 ml of water and the white precipitate was dissolved. The organic layer was then washed with water (2×150 ml), 150 ml of brine and dried over $MgSO_4$. The solvent was evaporated under vacuum to give the crude product which was recrystallized from ethyl acetate to afford 41.5 g (82%) yellow crystalline 2-nitro-4-chloro-6-bromophenol. $^1$H NMR (300 MHz, $CDCl_3$) δ8.11 (d, J=2.5 Hz, 1 H), 7.87 (d, J=2.5 Hz, 1H).

Step 2: Preparation of 2-nitro-4-chloro-6-bromoanisole

2-Nitro-4-chloro-6-bromoanisole was prepared by the same procedure as described for Step 2 of Preparation 2a using 2-nitro-4-chloro-6-bromophenol (16 g), methyl iodide (10.8 g), and potassium carbonate (26.3 g). Workup gave crude 2-nitro-4-chloro-6-bromoanisole (16.3 g, 96%) which was used in the next step without purification. $^1$H NMR (300 MHz, $CDCl_3$) δ7.80 (d, J=2.5 Hz, 1 H), 7.77 (d, J=2.5 Hz, 1H), 4.01 (s, 3H). $^{13}$C NMR (75 MHz, $CDCl_3$) δ149.7, 137.2 (2C), 130.0, 124.4, 120.5, 62.8.

Step 3: Preparation of 2-amino-4-chloro-6-bromoanisole (V, $R^1$=Br, $R^2$=H, $R^3$=Cl)

2-Amino-4-chloro-6-bromoanisole was prepared by the same procedure described for Step 3 of Preparation 2a except using 2-nitro-4-chloro-6-bromoanisole (16.2 g) and tin (14.5 g). Workup provided 2-amino-4-chloro-6-bromoanisole (14.0 g, 97%). $^1$H NMR (300 MHz, CDCl$_3$) δ6.88 (d, J=2.4 Hz, 1H), 6.65 (d, J=2.4 Hz, 1H), 3.80 (s, 3H). $^{13}$C NMR (75 MHz, CDCl$_3$) δ142.9, 141.9, 130.2, 121.4, 117.1, 114.6, 59.6.

Step 4: Preparation of (3-bromo-5-chloro-2-methoxyphenyl)hydrazine

The title compound was prepared by the general procedure described above for Preparations 2a–i using 2-amino-4-chloro-6-bromoanisole (6 g), NaNO$_2$ (1.9 g), and SnCl$_2$.2H$_2$O (112.6 g). Workup gave 4 g (63%) of 3-bromo-5-chloro-2-methoxyphenyl)hydrazine which was used without further purification.

Preparation 2c (5-Chloro-3-methyl-2-methoxyphenyl)hydrazine (III, $R^1$=CH$_3$, $R^2$=H, $R^3$=Cl)

Step 1: Preparation of 2-nitro-4-chloro-6-methylanisole

4-Chloro-2-methylanisole (46.8 g) was added dropwise to a mixture of concentrated HNO$_3$ (33 ml) and H$_2$SO$_4$ (99 ml) at 0° C. The reaction mixture was then poured into a ice water and extracted with dichloromethane. The organic layer was washed with water, dried over MgSO$_4$, and concentrated in vacuo to give a residue. The residue was purified by flash chromatography over silica gel (elution with 5% ethyl acetate in hexanes) to give 25 g (41%) of 2-nitro-4-chloro-6-methylanisole. $^1$H NMR (300 MHz, CDCl$_3$) δ7.64 (d, J=2.5 Hz, 1 H), 7.40 (d, J=2.5 Hz, 1 H), 3.89 (s, 3 H), 2.36 (s, 3 H).

Step 2: Preparation of 2-amino-4-chloro-6-methylanisole, (V, $R^1$=CH$_3$, $R^2$=H, $R^3$=Cl)

A suspension of 2-nitro-4-chloro-6-methylanisole (16 g) and 10% Pt(S)/C (1.6 g) in ethanol was hydrogenated at 50 psi for 3 hours. After filtration and concentration, purification by flash chromatography over silica gel (eluted with 10% ethyl acetate in hexanes) gave 12.3 g (90%) of 2-amino-4-chloro-6-methylanisole. $^1$H NMR (300 MHz, CDCl$_3$) δ6.58 (d, J=2.4 Hz, 1 H), 6.53 (d, J=2.4 Hz, 1 H), 3.77 (s, 3 H), 2.22 (s, 3 H).

Step 3: Preparation of (5-chloro-3-methyl-2-methoxyphenyl)hydrazine

The title compound was prepared by the general procedure described above for Preparations 2a–i using 2-amino-4-chloro-6-methylanisole, V (5.13 g), NaNO$_2$ (2.28 g), and SnCl$_2$.2H$_2$O(14.89 g). Workup gave 5 g (90%) of 5-chloro-3-methyl-2-methoxyphenyl)hydrazine.

Preparation 2d (3,5-Dichloro-2-methoxyphenyl)hydrazine (III, $R^1$=$R^3$=Cl, $R^2$=H)

Step 1: Preparation of 2-nitro-4,6-dichloroanisole

2-Nitro-4,6-dichloroanisole was prepared by the same procedure as described for Step 2 of Preparation 2a except using 2,4-dichloro-6-nitrophenol (52 g), methyl iodide (71 g), and potassium carbonate (41.4 g). Workup gave crude 2-nitro-4,6-dichloroanisole (50 g, 90%) which was used in the next step without purification.

Step 2: Preparation of 2-amino-4,6-dichloroanisole, (V, $R^1$=$R^3$=Cl, $R^2$=H)

2-Amino-4,6-dichloroanisole was prepared by same method as described in Step 2 of Preparation 2c except using 2-nitro-4,6-dichloroanisole (13.32 g) and 10%Pt(S)/C (1.33 g). Workup gave crude 2-amino-4,6-dichloroanisole (11 g, 95%) which was used in the next step without purification. $^1$H NMR (300 MHz, CDCl$_3$) δ6.73 (d, J=2.4 Hz, 1 H), 6.62 (d, J=2.4 Hz, 1 H), 3.82 (s, 3 H).

Step 3: Preparation of (3,5-dichloro-2-methoxyphenyl) hydrazine

The title compound was prepared by the general procedure described above for Preparations 2a–i using 2-amino-4,6-dichloroanisole, V (11 g), NaNO$_2$ (4.5 g), and SnCl$_2$.2H$_2$O(30 g). Workup gave 8 g (65%) of (3,5-dichloro-2-methoxyphenyl)hydrazine, Preparation 2d which was used in the next step without purification. $^1$H NMR (300 MHz, CDCl$_3$) δ6.97 (d, J=2.4 Hz, 1 H), 6.76 (d, J=2.4 Hz, 1 H), 3.79 (s, 3 H).

Preparation 2e (5-Chloro-4-methyl-2-methoxyphenyl)hydrazine (III, $R^1$=H, $R^2$=CH$_3$, $R^3$=Cl)

Step 1: Preparation of 4-chloro-5-methyl-2-nitroanisole

4-Chloro-5-methyl-2-nitroanisole was prepared by the same procedure as described for Step 2 of Preparation 2a except using 4-chloro-5-methyl-2-nitrophenol (50 g), methyl iodide (75.8 g), and potassium carbonate (44 g). Workup gave crude 4-chloro-5-methyl-2-nitroanisole (52.3 g, 97%) which was used in the next step without purification. $^1$H NMR (300 MHz, CDCl$_3$) δ7.85 (s, 1 H), 6.95 (s, 1 H), 3.94 (s, 3 H), 2.45 (s, 3 H).

Step 2: Preparation of 4-chloro-5-methyl-2-aminoanisole (V, $R^1$=H, $R^2$=CH$_3$, $R^3$=Cl)

4-Chloro-5-methyl-2-aminoanisole was prepared by the same method as described in Step 2 of Preparation 2c except using 4-chloro-5-methyl-2-nitroanisole (20 g) and 10%Pt (S)/C (2 g). Workup gave crude 4-chloro-5-methyl-2-aminoanisole, V (16 g, 94%) which was used in the next step without further purification. $^1$H NMR (300 MHz, CDCl$_3$) δ6.69 (s, 1 H), 6.60 (s, 1 H), 3.81 (s, 3 H), 2.25 (s, 3 H).

Step 3: Preparation of (5-chloro-4-methyl-2-methoxyphenyl)hydrazine

The title compound was prepared by the general procedure described above for Preparations 2a–i using 4-chloro-5-methyl-2-aminoanisole (10.26 g), NaNO$_2$ (4.5 g), and SnCl$_2$.2H$_2$O (30 g). Workup gave 3.7 g (33%) of (5-chloro-4-methyl-2-methoxyphenyl)hydrazine.

Preparation 2f (4-Bromo-5-chloro-2-methoxyphenyl)hydrazine (III, $R^1$=H, $R^2$=Br, $R^3$=Cl)

Step 1: Preparation of 4-chloro-5-bromo-2-aminoanisole (V, $R^1$=H, $R^2$=Br, $R^3$=Cl)

Bromine, Br$_2$ (26.4 g) was added to a solution of 4-chloro-o-anisidine (23.55 g) in dichloromethane (400 mL) at room temperature. The resulting mixture was stirred for 10 hours at room temperature and then was quenched with NaOH. The organic layer was washed with brine, dried over MgSO$_4$, and concentrated in vacuo. Purification of the residue by flash chromatography over silica gel (eluted with 10% ethyl acetate in hexanes) gave 11.8 g (33%) of the desired product 4-chloro-5-bromo-2-aminoanisole, V. $^1$H NMR (300 MHz, CDCl$_3$) δ6.94 (s, 1 H), 6.78 (s, 1 H), 3.83 (s, 3 H).

Step 2: Preparation of (4-bromo-5-chloro-2-methoxyphenyl)hydrazine

The title compound was prepared by the general procedure described above for Preparations 2a–i using 4-chloro-5-bromo-2-aminoanisole (7.68 g), NaNO$_2$ (2.25 g), and SnCl$_2$.2H$_2$O (15 g). Workup gave 5.5 g (73%) of (4-bromo-5-chloro-2-methoxyphenyl)hydrazine which was used in the next step without further purification.

Preparation 2g (2-methoxy-5-trifluoromethylphenyl)hydrazine (III, $R^1=R^2=H$, $R^3=CF_3$)

The title compound was prepared by the general procedure described above for Preparations 2a–i using 4-trifluromethyl-o-anisidine (V, $R^1=R^2=H$, $R^3=CF_3$), (22.7 g), NaNO$_2$ (9.02 g), and SnCl$_2$.2H$_2$O (60 g). Workup gave 18.1 g (74%) of (2-methoxy-5-trifluoromethylphenyl)hydrazine which was used in the next step without further purification. $^1$H NMR (300 MHz, CDCl$_3$) δ7.23 (d, J=2.0 Hz, 1 H), 7.05 (dd, J=8.2, 2.0 Hz, 1 H), 6.81 (d, J=8.3 Hz, 1 H), 3.89 (s, 3 H).

Preparation 2h (5-Bromo-2-methoxyphenyl)hydrazine (III, $R^1=R^2=H$, $R^3=Br$)

Step 1: Preparation of 4-bromo-2-nitroanisole

Bromine, Br$_2$ (16 ml, 311 mmol) was added in small portions to a solution of 2-nitroanisole (17.1 ml, 140 mmol) in glacial acetic acid (80 ml). The reaction mixture was then heated at 60° C. for one hour. The reaction was poured into 400 ml water, and extracted with 600 ml diethyl ether/600 ml saturated NaHSO$_3$ (aqueous). The organic layer was washed with NaHSO$_3$ solution, then with water, dried over sodium sulfate, and concentrated under vacuum. The residue was recrystallized from diethyl ether to give 28.4 g (87%) of 4-bromo-2-nitroanisole. $^1$H NMR (300 MHz, CDCl$_3$) δ7.970 (1H, d, J=2.5 Hz), 7.64 (1H, dd, J=8.9, 2.4 Hz), 7.00 (1H, d, J=8.9 Hz), 3.96 (3H, s).

Step 2: Preparation of 4-bromo-2-aminoanisole (V, $R^1=R^2=H$, $R^3=Br$).

Iron powder (16.1 g) was added to a stirring mixture of 4-bromo-2-nitroanisole (13.92 g, 60 mmol) in 200 ml ethanol. The reaction mixture was heated to reflux, whereupon 50 ml of 0.5N HCl solution was added dropwise over a 45 minute period. The reaction mixture was then refluxed for an additional 3 hours then was allowed to cool to room temperature and was then filtered through celite and the resulting filtrate was concentrated under vacuum. The resulting solid was suspended in saturated NaHCO$_3$ solution, then collected by filtration, and washed with water. The solid was recrystallized from cyclohexane to yield 4-bromo-2-aminoanisole (9.90 g, 82%). m.p. 93° C.; $^1$H NMR (300 MHz, CDCl$_3$) δ6.69 (2H, m), 6.52 (1H, d, J=9.0 Hz), 3.72 (3H, s).

Step 3: Preparation of (5-bromo-2-methoxyphenyl)hydrazine

The title compound was prepared by the general procedure described above for Preparations 2a–i using 4-bromo-2-aminoanisole (9.09 g), NaNO$_2$ (3.45 g), and SnCl$_2$.2H$_2$O (22.6 g). Workup gave 8.7 g (89%) of (5-bromo-2-methoxyphenyl)hydrazine which was used without further purification.

$^1$H NMR (300 MHz, CDCl$_3$) δ7.10 (1H, d, J=2.4 Hz), 6.85 (1H, dd, J=8.5, 2.4 Hz), 6.61 (1H, d, J=8.4 Hz), 3.81 (3H, s).

Preparation 2i (5-Fluoro-2-methoxyphenyl)hydrazine (III, $R^1=R^2=H$, $R^3=F$)

Step 1: Preparation of 4-fluoro-2-aminoanisole, (V, $R^1=R^2=H$, $R^3=F$)

A solution of 4-fluoro-2-nitroanisole (20.5 g, 120 mmol) in ethyl acetate (100 ml) was hydrogenated in a Parr shaker apparatus with 10% Pd on carbon (2 g) until a stable pressure reading was obtained. The reaction was filtered through Celite and concentrated under vacuum to an oil. The 4-fluoro-2-aminoanisole thus obtained (16.14 g, 96%) was used in the next step.

$^1$H NMR (300 MHz, CDCl$_3$) δ6.68 (1H, dd, J=8.7, 5.0 Hz), 6.45 (1H, dd, J=9.0, 2.9 Hz), 6.39 (1H, dt, J=8.7, 3.0 Hz), 3.83 (3H, s).

Step 2: Preparation of (5-fluoro-2-methoxyphenyl)hydrazine

The title compound was prepared by the general procedure described above for Preparations 2a–i using 4-fluoro-2-aminoanisole (14.11 g), NaNO$_2$ (7.59 g) and SnCl$_2$.2H$_2$O (49.64 g). Workup gave 4.9 g (31%) of (5-fluoro-2-methoxyphenyl)hydrazine. MS (M–H)$^+$: 157.00; $^1$H NMR (300 MHz, CDCl$_3$) δ6.71 (1H, dd, J=10.5, 3.0 Hz), 6.32 (1H, dd, J=7.5, 4.9 Hz), 6.38 (1H, dt, J=8.4, 3.0 Hz), 3.78 (3H, s).

Anal. Calcd. for C$_7$H$_9$N$_2$OF.0.1 EtOAc: C, 53.88; H, 5.99; N, 16.98. Found: C, 53.86; H, 5.64; N, 16.93.

Preparations 3a–q

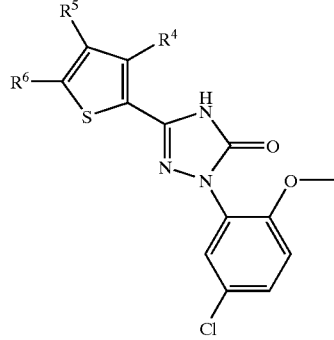

IIc

Preparations 3a–q (IIc) were prepared from the corresponding Preparation 1a–q (IVa) and Preparation 2 (III, $R^1=R^2=H$, $R^3=Cl$) according to the following general procedure.

General Procedure for the Preparation of Preparations 3a–q

An appropriate thiophen-2-yl oxo-acetic acid, Preparation 1a–q (1.0 equivalent) and (2-methoxy-5-chlorophenyl)hydrazine, Preparation 2 (1.0 equivalent) were refluxed in acetonitrile (15–25 ml/mmol starting material) for 30–60 min. The reaction was cooled to room temperature. Triethylamine (1.1 equivalent) and diphenylphosphorylazide (DPPA, 1.1 equivalent) were added, and the reaction was heated at reflux for approximately 3 to 18 hours. After the reaction mixture cooled to room temperature, solids were collected by filtration and washed with acetonitrile and diethyl ether to provide Preparations 3a–q. If necessary, the product was further purified by flash chromatography on silica gel 60 eluted with an hexane/ethyl acetate.

Preparation 3a 5-(5-Bromothiophen-2-yl)-2-(5-chloro-2-methoxyphenyl)-2,4-dihydro-[1,2,4]triazol-3-one (IIc, $R^4=R^5=H$, $R^6=Br$)

Preparation 3a was prepared by the general procedure described above for Preparations 3a–q using Preparation 1a (4.70 g, 20 mmol), Preparation 2 (3.46 g, 20 mmole), Et$_3$N (3.06 ml, 22 mmol), and diphenylphosphorylazide (DPPA, 4.74 ml, 22 mmol). Workup gave 5.44 g (70%) of 5-(5-bromothiophen-2-yl)-2-(5-chloro-2-methoxyphenyl)-2,4-dihydro-[1,2,4]triazol-3-one. MS (M–H)⁻: 386.0; ¹H NMR (300 MHz, DMSO-d₆) δ12.57 (1H, s), 7.53–7.49 (2H, m), 7.42 (1H, d, J=3.9 Hz), 7.35 (1H, d, J=3.9 Hz), 7.22 (1H, d, J=9.3 Hz), 3.79 (3H, s). IR (KBr) 3420, 2936, 1698, 1595, 1502, 1474, 1288, 1227 cm⁻¹.

Anal. Calcd. for $C_{13}H_9N_3O_2SBrCl\cdot 0.1$ EtOAc: C, 40.70; H, 2.50; N, 10.63. Found: C, 40.78; H, 2.71; N, 10.55.

Preparation 3b 5-(5-Chlorothiophen-2-yl)-2-(5-chloro-2-methoxyphenyl)-2,4-dihydro-[1,2,4]triazol-3-one
(IIc, $R^4=R^5=H$, $R^6=Cl$)

Preparation 3b was prepared by the general procedure described for Preparations 3a–q using Preparation 1b (1.91 g, 10 mmol), Preparation 2 (1.73 g, 10 mmol), Et₃N (1.53 ml, 11 mmol), and diphenylphosphorylazide, DPPA (2.37 ml, 11 mmol). Workup gave 2.54 g (74%) of 5-(5-chlorothiophen-2-yl)-2-(5-chloro-2-methoxyphenyl)-2,4-dihydro-[1,2,4]triazol-3-one. MS (M+H)⁺: 341.99; ¹H NMR (300 MHz, DMSO-d₆) δ12.59 (1H, s), 7.53 (1H, d, J=2.7 Hz), 7.50 (1H, s), 7.46 (1H, d, J=3.9 Hz), 7.25 (1H, d, J=3.9 Hz), 7.22 (1H, d, J=9.3 Hz), 3.79 (3H, s). IR (KBr) 3088, 2837, 1699, 1595, 1503, 1477, 1426, 1289, 1227 cm⁻.

Anal. Calcd. for $C_{13}H_9N_3O_2SCl_2$: C, 45.63; H, 2.65; N, 12.28. Found: C, 45.47; H, 2.57; N, 12.14.

Preparation 3c 5-(5-Iodothiophen-2-yl)-2-(5-chloro-2-methoxyphenyl)-2,4-dihydro-[1,2,4]triazol-3-one
(IIc, $R^4=R^5=H$, $R^6=I$)

The title compound was prepared by the general procedure described for Preparations 3a–q using Preparation 1c (80 mg, 0.28 mmol), Preparation 2 (49 mg, 0.28 mmol), Et₃N (0.044 ml, 0.31 mmol), and diphenylphosphorylazide, DPPA (0.067 ml, 0.31 mmol). Workup gave 42 mg (19%) of 5-(5-iodothiophen-2-yl)-2-(5-chloro-2-methoxyphenyl)-2,4-dihydro-[1,2,4]triazol-3-one after flash chromatography on silica gel 60 with hexane/ethyl acetate 10:1 to 1:1. MS (M–H)⁻: 431.85; ¹H NMR (300 MHz, CDCl₃) δ12.15 (1H, s), 7.44–7.37 (2H, m), 7.24–7.13 (2H, m), 6.98 (1H, d, J=8.8 Hz), 3.85 (3H, s).

Preparation 3d 5-(4-Bromothiophen-2-yl)-2-(5-chloro-2-methoxyphenyl)-2,4-dihydro-[1,2,4]triazol-3-one
(IIc, $R^4=R^6=H$, $R^5=Br$)

The title compound was prepared by the general procedure described for Preparations 3a–q using Preparation 1d (1.18 g, 5.0 mmol), Preparation 2 (0.865 g, 5.0 mmol), Et₃N (0.765 ml, 5.5 mmole), and diphenylphosphorylazide, DPPA (1.19 ml, 5.5 mmol). Workup gave 1.22 g (63%) of 5-(4-bromothiophen-2-yl)-2-(5-chloro-2-methoxyphenyl)-2,4-dihydro-[1,2,4]triazol-3-one. MS (M–H)⁻: 385.81; ¹H NMR (300 MHz, DMSO-d₆) δ12.55 (1H, s), 7.87 (1H, d, J=1.5 Hz), 7.58 (1H, d, J=1.5 Hz), 7.54–7.51 (2H, m), 7.23 (1H, dd, J=7.2 Hz, 2.4 Hz), 3.79 (3H, s).

Anal. Calcd. for $C_{13}H_9BrClN_3O_2S$: C, 40.38; H, 2.35; N, 10.87. Found: C, 40.22; H, 2.38; N, 10.85.

Preparation 3e 5-(4-Chlorothiophen-2-yl)-2-(5-chloro-2-methoxyphenyl)-2,4-dihydro-[1,2,4]triazol-3-one
(IIc, $R^4=R^6=H$, $R^5=Cl$)

The title compound was prepared by the general procedure described for Preparations 3a–q using Preparation 1e (0.953 g, 5.0 mmol), Preparation 2 (0.865 g, 5.0 mmol), Et₃N (0.765 ml, 5.5 mmole), and diphenylphosphorylazide, DPPA (1.19 ml, 5.5 mmol). Workup gave 1.24 g (72%) of 5-(4-chlorothiophen-2-yl)-2-(5-chloro-2-methoxyphenyl)-2,4-dihydro-[1,2,4]triazol-3-one. MS (M–H)⁻: 339.84; ¹H NMR (300 MHz, DMSO-d6) δ7.78 (1H, d, J=1.5 Hz), 7.55–7.51 (3H, m), 7.23 (1H, dd, J=7.3, J=2.2 Hz), 3.80 (3H, s).

Anal. Calcd. for $C_{13}H_9Cl_2N_3O_2S$: C, 45.63; H, 2.65; N, 12.28. Found: C, 45.51; H, 2.60; N, 12.38.

Preparation 3f 5-(3-Bromothiophen-2-yl)-2-(5-chloro-2-methoxyphenyl)-2,4-dihydro-[1,2,4]triazol-3-one
(IIc, $R^4=Br$, $R^5=R^5=H$)

The title compound was prepared by the general procedure described for Preparations 3a–q using Preparation 1f (438 mg, 2.0 mmol), Preparation 2 (346 mg, 2.0 mmol), Et₃N (0.31 ml, 2.2 mmol), and diphenylphosphorylazide, DPPA (0.50 ml, 2.2 mmol). Workup gave 540 mg (70%) of 5-(3-bromothiophen-2-yl)-2-(5-chloro-2-methoxyphenyl)-2,4-dihydro-[1,2,4]triazol-3-one after flash chromatography on silica gel 60 eluted with hexane/ethyl acetate 2:1. MS (M–H)⁻: 385.99; ¹H NMR (300 MHz, DMSO-d6) δ12.31 (1H, s), 7.86 (1H, d, J=5.3 Hz), 7.54–7.49 (2H, m), 7.27–7.21 (2H, m), 3.79 (3H, s); IR (KBr) cm⁻¹ 3082.9, 1695.2, 1590.1, 1504.0, 1419.7, 1273.1, 1260.4.

Anal. Calcd. for $C_{13}H_9N_3ClBrO_2S$: C, 40.38; H, 2.35; N, 10.87. Found: C, 40.56; H, 2.59; N, 10.71.

Preparation 3g 5-(3-Chlorothiophen-2-yl)-2-(5-chloro-2-methoxyphenyl)-2,4-dihydro-[1,2,4]triazol-3-one
(IIc, $R^4=Cl$, $R^5=R^6=H$)

The title compound was prepared by the general procedure described for Preparations 3a–q using Preparation 1 g (0.381 g, 2.0 mmol), Preparation 2 (0.346 g, 2.0 mmol), Et₃N (0.306 ml, 2.2 mmol), and diphenylphosphorylazide, DPPA (0.474 ml, 2.2 mmol). Workup gave 0.519 g (75%) of 5-(3-chlorothiophen-2-yl)-2-(5-chloro-2-methoxyphenyl)-2,4-dihydro-[1,2,4]triazol-3-one. MS (M+H)⁺: 344.00; ¹H NMR (300 MHz, DMSO-d₆) δ12.30 (1H, s), 7.88 (1H, d, J=5.4 Hz), 7.55–7.50 (2H, m), 7.25–7.22 (2H, m), 3.80 (3H, s). IR (KBr) 3083, 2969, 1713, 1697, 1586, 1503, 1471, 1444, 1352, 1271 cm⁻¹.

Anal. Calcd. for $C_{13}H_9N_3O_2SCl_2\cdot 0.2$ Et₂O: C, 46.43; H, 3.11; N, 11.77. Found: C, 43.43; H, 2.81; N, 11.79.

Preparation 3h 5-(3-Iodothiophen-2-yl)-2-(5-chloro-2-methoxyphenyl)-2,4-dihydro-[1,2,4]triazol-3-one
(IIc, $R^4=I$, $R^5=R^6=H$)

The title compound was prepared by the general procedure described for Preparations 3a–q using Preparation 1h (49 mg, 0.17 mmol), Preparation 2 (30 mg, 0.17 mmol), Et₃N (0.026 ml, 0.19 mmol), and diphenylphosphorylazide, DPPA (0.041 ml, 0.19 mmol). Workup gave 55 mg (42%) of 5-(3-iodothiophen-2-yl)-2-(5-chloro-2-methoxyphenyl)-2, 4-dihydro-[1,2,4]triazol-3-one after flash chromatography on silica gel 60 eluted with hexane/ethyl acetate 4:1 to 1:1. MS (M–H)⁻: 431.84; ¹H NMR (300 MHz, CDCl₃) δ10.39 (1H, s), 7.45 (1H, d, J=2.5 Hz), 7.39–7.36 (2H, m), 7.16 (1H, d, J=5.2 Hz), 6.98 (1H, d, J=8.9 Hz), 3.88 (3H, s).

Preparation 3i 5-(4,5-Dibromothiophen-2-yl)-2-(5-chloro-2-methoxyphenyl)-2,4-dihydro-[1,2,4]triazol-3-one (IIc, $R^4$=H, $R^5$=$R^6$=Br)

The title compound was prepared by the general procedure described for Preparations 3a–q using Preparation 1i (628 mg, 2.0 mmol), Preparation 2 (346 mg, 2.0 mmol), Et$_3$N (0.306 ml, 2.2 mmol), and diphenylphosphorylazide, DPPA (0.474 ml, 2.2 mmol). Workup gave 494 mg (53%) of 5-(4,5-dibromothiophen-2-yl)-2-(5-chloro-2-methoxyphenyl)-2,4-dihydro-[1,2,4]triazol-3-one. MS (M–H)$^-$: 463.81; $^1$H NMR (300 MHz, DMSO-d$_6$) δ12.59 (1H, s), 7.53–7.50 (3H, m), 7.23 (1H, d, J=8.4 Hz), 3.79 (3H, s).

Anal. Calcd. for $C_{13}H_8Br_2ClN_3O_2S$: C, 33.54; H, 1.73; N, 9.03. Found: C, 33.45; H, 1.58; N, 8.85.

Preparation 3j 5-(4,5-Dichlorothiophen-2-yl)-2-(5-chloro-2-methoxyphenyl)-2,4-dihydro-[1,2,4]triazol-3-one (IIc, $R^4$=H, $R^5$=$R^6$=Cl)

The title compound was prepared by the general procedure described for Preparations 3a–q using Preparation 1j (180 mg, 0.80 mmol), Preparation 2 (139 mg, 0.80 mmol), Et$_3$N (0.123 ml, 0.88 mmol), and diphenylphosphorylazide, DPPA (0.19 ml, 0.88 mmol). Workup gave 175 mg (58%) of 5-(4,5-dichlorothiophen-2-yl)-2-(5-chloro-2-methoxyphenyl)-2,4-dihydro-[1,2,4]triazol-3-one. MS (M–H)$^-$: 375.86; $^1$H NMR (300 MHz, DMSO-d$_6$) δ12.65 (1H, s), 7.56–7.51 (3H, m), 7.23 (1H, d, J=8.5 Hz), 3.79 (3H, s).

Preparation 3k 5-(4-Bromo-5-chlorothiophen-2-yl)-2-(5-chloro-2-methoxyphenyl)-2,4-dihydro-[1,2,4]triazol-3-one (IIc, $R^4$=H, $R^5$=Br, $R^6$=Cl)

The title compound was prepared by the general procedure described for Preparations 3a–q using Preparation 1k (270 mg, 1.0 mmol), Preparation 2 (173 mg, 1.0 mmol), Et$_3$N (0.153 ml, 1.1 mmol), and diphenylphosphorylazide, DPPA (0.237 ml, 1.1 mmol). Workup gave 229 mg (54%) of 5-(4-bromo-5-chlorothiophen-2-yl)-2-(5-chloro-2-methoxyphenyl)-2,4-dihydro-[1,2,4]triazol-3-one. MS (M–H)$^-$: 419.84; $^1$H NMR (300 MHz, DMSO-d$_6$) δ12.62 (1H, s), 7.56–7.50 (3H, m), 7.23 (1H, d, J=8.4 Hz), 3.79 (3H, s).

Anal. Calcd. for $C_{13}H_8BrCl_2N_3O_2S$: C, 37.08; H, 1.91; N, 9.98. Found: C, 37.18; H, 1.93; N, 9.99.

Preparation 3l 5-(3,4-Dibromothiophen-2-yl)-2-(5-chloro-2-methoxyphenyl)-2,4-dihydro-[1,2,4]triazol-3-one (IIc, $R^4$=$R^5$=Br, $R^6$=H)

The title compound was prepared by the general procedure described for Preparations 3a–q using Preparation 1l (314 mg, 1.0 mmol), Preparation 2 (173 mg, 1.0 mmol), Et$_3$N (0.153 ml, 1.1 mmol), and diphenylphosphorylazide, DPPA (0.237 ml, 1.1 mmol). Workup gave 371 mg (80%) of 5-(3,4-dibromothiophen-2-yl)-2-(5-chloro-2-methoxyphenyl)-2,4-dihydro-[1,2,4]triazol-3-one. MS (M–H)$^-$: 463.78; $^1$H NMR (300 MHz, DMSO-d$_6$) δ12.43 (1H, s), 8.13 (1H, s), 7.55–7.51 (2H, m), 7.26–7.23 (1H, m), 3.81 (3H, s).

Anal. Calcd. for $C_{13}H_8Br_2ClN_3O_2S$: C, 33.54; H, 1.73; N, 9.03. Found: C, 33.64; H, 1.74; N, 9.07.

Preparation 3m 5-(3,4-Dichlorothiophen-2-yl)-2-(5-chloro-2-methoxyphenyl)-2,4-dihydro-[1,2,4]triazol-3-one (IIc, $R^4$=$R^5$=Cl, $R^6$=H)

The title compound was prepared by the general procedure described for Preparations 3a–q using Preparation 1m (81 mg, 0.36 mmol), Preparation 2 (63 g, 0.36 mmol), Et$_3$N (0.055 ml, 0.40 mmol), and diphenylphosphorylazide, DPPA (0.086 ml, 0.40 mmol). Workup gave 46 g (41%) of 5-(3,4-dichlorothiophen-2-yl)-2-(5-chloro-2-methoxyphenyl)-2,4-dihydro-[1,2,4]triazol-3-one. MS (M–H)$^-$: 375.85; $^1$H NMR (300 MHz, DMSO-d$_6$) δ12.47 (1H, s), 8.06 (1H, s), 7.54–7.52 (2H, m), 7.26–7.23 (1H, m), 3.81 (3H, s).

Preparation 3n 5-(3,5-Dibromothiophen-2-yl)-2-(5-chloro-2-methoxyphenyl)-2,4-dihydro-[1,2,4]triazol-3-one (IIc, $R^4$=$R^6$=Br, $R^5$=H)

The title compound was prepared by the general procedure described for Preparations 3a–q using Preparation 1n (314 mg, 1.0 mmol), Preparation 2 (173 mg, 1.0 mmol), Et$_3$N (0.153 ml, 1.1 mmol), and diphenylphosphorylazide, DPPA (0.237 ml, 1.1 mmol). Workup gave 292 mg (63%) of 5-(3,5-dibromothiophen-2-yl)-2-(5-chloro-2-methoxyphenyl)-2,4-dihydro-[1,2,4]triazol-3-one. MS (M–H)$^-$: 463.77; $^1$H NMR (300 MHz, DMSO-d$_6$) δ12.38 (1H, s), 7.55–7.52 (3H, m), 7.25–7.22 (1H, m), 3.81 (3H, s).

Anal. Calcd. for $C_{13}H_8Br_2ClN_3O_2S$: C, 33.54; H, 1.73; N, 9.03. Found: C, 33.70; H, 1.86; N, 9.04.

Preparation 3o 2-(5-Chloro-2-methoxyphenyl)-5-(3,4,5-tribromothiophen-2-yl)-2,4-dihydro-[1,2,4]triazol-3-one (IIc, $R^4$=$R^5$=$R^6$=Br)

The title compound was prepared by the general procedure described for Preparations 3a–q using Preparation 1o (136 mg, 0.35 mmol), Preparation 2 (60 mg, 0.35 mmol), Et$_3$N (0.053 ml, 0.38 mmol), and diphenylphosphorylazide, DPPA (0.082 ml, 0.38 mmol). Workup gave 95 mg (60%) of 2-(5-chloro-2-methoxyphenyl)-5-(3,4,5-tribromothiophen-2-yl)-2,4-dihydro-[1,2,4]triazol-3-one. MS (M–H)$^-$: 543.70; $^1$H NMR (300 MHz, DMSO-d$_6$) δ12.52 (1H, s), 7.55–7.51 (2H, m), 7.26–7.23 (1H, m), 3.81 (3H, s).

Preparation 3p 2-(5-Chloro-2-methoxyphenyl)-5-(3,4,5-trichlorothiophen-2-yl)-2,4-dihydro-[1,2,4]triazol-3-one (IIc, $R^4$=$R^5$=$R^6$=Cl)

The title compound was prepared by the general procedure described for Preparations 3a–q using Preparation 1p (95 mg, 0.37 mmol), Preparation 2 (64 mg, 0.37 mmol), Et$_3$N (0.056 ml, 0.41 mmol), and diphenylphosphorylazide, DPPA (0.087 ml, 0.41 mmol). Workup gave 90 mg (60%) of 2-(5-chloro-2-methoxyphenyl)-5-(3,4,5-trichlorothiophen-2-yl)-2,4-dihydro-[1,2,4]triazol-3-one.

MS (M–H)$^-$: 409.85; $^1$H NMR (300 MHz, DMSO-d$_6$) δ12.57 (1H, s), 7.56–7.52 (2H, m), 7.26–7.23 (1H, m), 3.81 (3H, s).

Preparation 3q 5-(4-Bromo-5-methylthiophen-2-yl)-2-(5-chloro-2-methoxyphenyl)-2,4-dihydro-[1,2,4]triazol-3-one (IIc, $R^4$=H, $R^5$=Br, $R^6$=CH$_3$)

The title compound was prepared by the general procedure described for Preparations 3a–q using Preparation 1q (747 mg, 3.0 mmol), Preparation 2 (519 mg, 3.0 mmol), Et$_3$N (0.46 ml, 3.3 mmol), and diphenylphosphorylazide, DPPA (0.71 ml, 3.3 mmol). Workup gave 490 mg (41%) of the crude product, which was further purified by preparative HPLC to provide 5-(4-bromo-5-methylthiophen-2-yl)-2-(5-chloro-2-methoxyphenyl)-2,4-dihydro-[1,2,4]triazol-3-one. $^1$H NMR (300 MHz, DMSO-d$_6$) δ12.48 (1H, s), 7.54–7.48 (3H, m), 7.23 (1H, d, J=8.7 Hz), 3.79 (3H, s), 2.40 (3H, s).

Preparations 3r and 3s

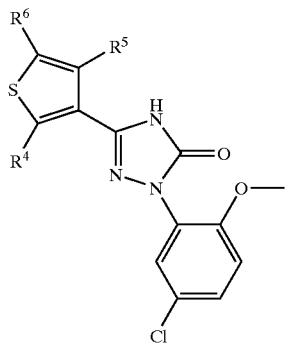

IId

Preparations 3r and 3s (IId) were prepared from the corresponding Preparation 1r or 1s (IVb) and Preparation 2 (III, $R^1$=$R^2$=H, $R^3$=Cl) according to the following general procedure.

General Procedure Preparations of 3r and 3s

An appropriate thiophen-3-yl oxo-acetic acid, Preparation 1r or 1s (1.0 equivalent) and (2-methoxy-5-chlorophenyl)hydrazine, Preparation 2 (1.0 equivalent) were refluxed in acetonitrile (15–25 ml/mmol starting material) for 30–60 min. The reaction was cooled to room temperature. Triethylamine, Et$_3$N (1.1 equivalent) and diphenylphosphorylazide (DPPA, 1.1 equivalent) were added, and the reaction was heated at reflux for approximately 3 to 18 hours. After the reaction mixture cooled to room temperature, solids were collected by filtration and washed with acetonitrile and diethyl ether to provide Preparations 3r–s. If necessary, the product was further purified by flash chromatography on silica gel 60 eluted with an hexane/ethyl acetate.

Preparation 3r 2-(5-Chloro-2-methoxyphenyl)-5-(2,5-dibromothiophen-3-yl)-2,4-dihydro-[1,2,4]triazol-3-one (IId, $R^4$=$R^6$=Br, $R^5$=H)

The title compound was prepared by the general procedure described for Preparations 3r–s using Preparation 1r (111 mg, 0.35 mmol), Preparation 2 (61 mg, 0.35 mmol), Et$_3$N (0.054 ml, 0.39 mmol), and diphenylphosphorylazide, DPPA (0.083 ml, 0.39 mmol). Workup gave 106 mg (65%) of 2-(5-chloro-2-methoxyphenyl)-5-(2,5-dibromothiophen-3-yl)-2,4-dihydro-[1,2,4]triazol-3-one. MS (M–H)$^-$: 463.79; $^1$H NMR (300 MHz, DMSO-d$_6$) δ12.24 (1H, s), 7.54–7.50 (3H, m), 7.24 (1H, d, J=8.7 Hz), 3.80 (3H, s).

Anal. Calcd. for C$_{13}$H$_8$Br$_2$ClN$_3$O$_2$S: C, 33.54; $^1$H, 1.73; N, 9.03. Found: C, 33.83; $^1$H, 1.75; N, 8.81.

Preparation 3s 2-(5-Chloro-2-methoxyphenyl)-5-(2,5-dichlorothiophen-3-yl)-2,4-dihydro-[1,2,4]triazol-3-one (IId, $R^4$=$R^6$=Cl, $R^5$=H)

The title compound was prepared by the general procedure described for Preparations 3r–s using Preparation 1s (392 mg, 2.0 mmol), Preparation 2 (346 mg, 2.0 mmol), Et$_3$N (0.31 ml, 2.2 mmol), and diphenylphosphorylazide, DPPA (0.50 ml, 2.2 mmol). Workup gave 525 mg (70%) of 2-(5-chloro-2-methoxyphenyl)-5-(2,5-dichlorothiophen-3-yl)-2,4-dihydro-[1,2,4]triazol-3-one. MS (M–H)$^-$: 376.08; $^1$H NMR (300 MHz, DMSO-d$_6$) δ12.27 (1H, s), 7.54–7.49 (2H, m), 7.43 (1H, s), 7.23 (1H, d, J=8.6 Hz), 3.79 (3H, s). IR (KBr) cm$^{-1}$ 3423.5, 3074.8, 1702.7, 1594.7, 1584.3, 1545.6, 1503.3, 1462.8, 1366.6, 1293.3.

Anal. Calcd. for C$_{13}$H$_8$N$_3$Cl$_3$O$_2$S: C, 41.46; H, 2.14; N, 11.16. Found: C, 41.68; H, 2.28; N, 10.87.

Preparations 4a–i

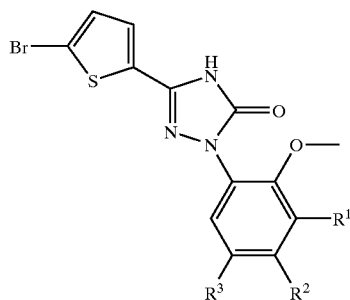

IIe

Preparations 4a–i (IIe) were prepared from the corresponding (2-methoxyphenyl)hydrazine derivative, Preparation 2a–i (III) and (5-bromothiophen-2-yl)-oxo-acetic acid (IVa, $R^4$=$R^5$=H, $R^6$=Br) according to the following general procedure.

General Procedure for Preparations of 4a–i (5-Bromothiophen-2-yl)-oxo-acetic acid, Preparation 1a (1.0 equivalent) and an appropriate (2-methoxyphenyl)hydrazine derivative, Preparation 2a–i (1.0 equivalent) were refluxed in acetonitrile (15–25 ml/mmol starting material) for 30–60 min. The reaction was cooled to room temperature. Triethylamine (1.1 equivalent) and diphenylphosphorylazide (DPPA, 1.1 equivalent) were added, and the reaction was heated at reflux for approximately 3 to 18 hours. After the reaction mixture cooled to room temperature, solids were collected by filtration and washed with acetonitrile and diethyl ether to provide Preparations 4a–i. If necessary, the product was further purified by flash chromatography on silica gel 60 eluted with a hexane/ethyl acetate mixture.

Preparation 4a 2-(3-Allyl-5-chloro-2-methoxyphenyl)-5-(5-bromothiophen-2-yl)-2,4-dihydro-[1,2,4]triazol-3-one (IIe, $R^1$=CH$_2$CH=CH$_2$, $R^2$=H, $R^3$=Cl)

The title compound was prepared by the general procedure described above for Preparations 4a–i using Preparation 2a (16 g), (5-bromothiophen-2-yl)-oxo-acetic acid, Preparation 1a (17.6 g), Et$_3$N (8.3 g), and diphenylphosphorylazide, DPPA (22.7 g). Workup gave 19.2 g (60%) of 2-(3-Allyl-5-chloro-2-methoxyphenyl)-5-(5-bromothiophen-2-yl)-2,4-dihydro-[1,2,4]triazol-3-one. $^1$H NMR (300 MHz, DMSO-d$_6$) δ7.45 (d, J=4 Hz, 1 H), 7.44 (s, 1 H), 7.36 (d, J=4 Hz, 1 H), 7.35 (s, 1 H), 6.02–5.96 (m, 1 H), 5.14–5.09 (m, 2 H), 3.64 (s, 3 H),3.43 (d, J=6.5 Hz, 2 H); $^{13}$C NMR (75 MHz, DMSO-D$_6$) δ153.3, 153.0, 141.0, 136.6, 136.4, 131.7, 130.5, 130.3, 128.5, 127.2, 127.0, 117.0, 114.7, 61.5, 33.5; IR (KBr, cm$^{-1}$) 1700; MS(ESI) 425 (M−1)$^+$.

Anal Calcd for C$_{16}$H$_{13}$Br$_2$ClN$_3$O$_2$S C, 45.04; H, 3.07; N, 9.85. Found: C, 44.92; H, 3.03; N, 9.66.

Preparation 4b 2-(3-Bromo-5-chloro-2-methoxyphenyl)-5-(5-bromothiophen-2-yl)-2,4-dihydro-[1,2,4]triazol-3-one (IIe, R$^1$=Br, R$^2$=H, R$^3$=Cl)

The title compound was prepared by the general procedure described for Preparations 4a–i using Preparation 2b (4 9), (5-bromothiophen-2-yl)-oxo-acetic acid, Preparation 1a (3.7 g), Et$_3$N (1.8 g), and diphenylphosphorylazide, DPPA (4.8 g). Workup gave 3.1 g (42%) of 2-(3-bromo-5-chloro-2-methoxyphenyl)-5-(5-bromothiophen-2-yl)-2,4-dihydro-[1,2,4]triazol-3-one. $^1$H NMR (300 MHz, DMSO-D$_6$) δ7.91 (d, J=2.6 Hz, 1H), 7.68 (d, J=2.6 Hz, 1H), 7.46 (d, J=4.1 Hz, 1H), 7.37 (d, J=4.1 Hz, 1H), 3.74 (s, 3H). $^{13}$C NMR (75 MHz, DMSO-D$_6$) δ153.0, 151.8, 141.0, 132.8, 131.5, 131.4, 129.9, 128.5, 128.2, 128.1, 118.2, 114.7, 61.4.

Preparation 4c 5-(5-Bromothiophen-2-yl)-2-(5-chloro-2-methoxy-3-methylphenyl)-2,4-dihydro-[1,2,4]triazol-3-one (IIe, R$^1$=CH$_3$, R$^2$=H, R$^3$=Cl)

The title compound was prepared by the general procedure described for Preparations 4a–i using Preparation 2c (1.86 g), (5-bromothiophen-2-yl)-oxo-acetic acid, Preparation 1a (2.35 g), Et$_3$N (1.111 g), and diphenylphosphorylazide, DPPA (3.025 g). Workup gave 2.8 g (70%) of 5-(5-bromothiophen-2-yl)-2-(5-chloro-2-methoxy-3-methylphenyl)-2,4-dihydro-[1,2,4]triazol-3-one. $^1$H NMR (300 MHz, DMSO-d$_6$) δ12.67 (s, 1 H), 7.44–7.35 (m, 4 H), 3.64 (s, 3 H), 2.26 (s, 3 H); $^{13}$C NMR (75 MHz, DMSO-d$_6$) δ154.3, 153.3, 140.9, 134.6, 131.7, 131.3, 130.4, 128.4, 127.0, 126.3, 114.7, 60.9, 15.0. IR (KBr, cm$^{-1}$) 3432, 1711; MS(ESI) 399 (M−1)$^+$.

Preparation 4d 5-(5-Bromothiophen-2-yl)-2-(3,5-dichloro-2-methoxyphenyl)-2,4-dihydro-[1,2,4]triazol-3-one (IIe, R$^1$=R$^3$=Cl, R$^2$=H)

The title compound was prepared by the general procedure described for Preparations 4a–i using Preparation 2d (3.5 g), (5-bromothiophen-2-yl)-oxo-acetic acid, Preparation 1a (3.995 g), Et$_3$N (1.9 g), and diphenylphosphorylazide, DPPA (5.146 g). Workup gave 4.10 g (57%) of 5-(5-bromothiophen-2-yl)-2-(3,5-dichloro-2-methoxyphenyl)-2,4-dihydro-[1,2,4]triazol-3-one. $^1$H NMR (300 MHz, DMSO-d$_6$) δ7.80 (d, J=2.6 Hz, 1 H), 7.64 (d, J=2.6 Hz, 1 H), 7.46 (d, J=3.9 Hz, 1 H), 7.37 (d, J=3.9 Hz, 1 H), 3.79 (s, 3 H); $^{13}$C NMR (75 MHz, DMSO-D$_6$) δ153.2, 150.9, 141.3, 131.9, 131.7, 130.2, 129.1, 128.7, 128.1, 127.6, 115.0, 61.7; IR (KBr, cm$^{-1}$) 3442 (br), 1715; MS(ESI) 421 (M)$^+$.

Anal Calcd for C$_{13}$H$_8$BrCl$_2$N$_3$O$_2$S C, 37.08; H, 1.91; N, 9.98. Found: C, 37.20; H, 1.96; N, 10.03.

Preparation 4e 5-(5-Bromothiophen-2-yl)-2-(5-chloro-2-methoxy-4-methylphenyl)-2,4-dihydro-[1,2,4]triazol-3-one (IIe, R$^1$=H, R$^2$=CH$_3$, R$^3$=Cl)

The title compound was prepared by the general procedure described for Preparations 4a–i using Preparation 2e (3.7 g), (5-bromothiophen-2-yl)-oxo-acetic acid, Preparation 1a (4.7 g), Et$_3$N (2.22 g), and diphenylphosphorylazide, DPPA (6.05 g). Workup gave 4 g (50%) of 5-(5-bromothiophen-2-yl)-2-(5-chloro-2-methoxy-4-methylphenyl)-2,4-dihydro-[1,2,4]triazol-3-one. $^1$H NMR (300 MHz, DMSO-d$_6$) δ12.53 (s, 1 H), 7.44 (s, 1 H), 7.41 (d, J=4.0 Hz, 1 H), 7.33 (d, J=4.0 Hz, 1 H), 7.20 (s, 1 H), 3.77 (s, 3 H). 2.32 (s, 3 H); $^{13}$C NMR (75 MHz, DMSO-d$_6$) δ153.8, 153.0, 140.4, 137.9, 131.4, 130.2, 128.9, 128.0, 123.6, 123.0, 115.1, 114.3, 56.2, 19.8; IR (KBr, cm$^{-1}$) 1706; MS(ESI) 399 (M−1)$^+$.

Anal Calcd for C$_{14}$H$_{11}$BrClN$_3$O$_2$S C, 41.97; H, 2.77; N, 10.49. Found: C, 42.03; H, 2.87; N, 10.48.

Preparation 4f 2-(4-Bromo-5-chloro-2-methoxyphenyl)-5-(5-bromothiophen-2-yl)-2,4-dihydro-[1,2,4]triazol-3-one (IIe, R$^1$=H, R$^2$=Br, R$^3$=Cl)

The title compound was prepared by the general procedure described for Preparations 4a–i using Preparation 2f (5.0 g), ), (5-bromothiophen-2-yl)-oxo-acetic acid, Preparation 1a (4.7 g), Et$_3$N (2.22 g), and diphenylphosphorylazide, DPPA (6.05 g). Workup gave 7 g (75%) of 2-(4-bromo-5-chloro-2-methoxyphenyl)-5-(5-bromothiophen-2-yl)-2,4-dihydro-[1,2,4]triazol-3-one. $^1$H NMR (300 MHz, DMSO-d$_6$) δ12.60 (s, 1 H), 7.70 (s, 1 H), 7.59 (s, 1 H), 7.40 (d, J=4.0 Hz, 1 H), 7.34 (d, J=4.0 Hz, 1 H), 3.82 (s, 3 H); $^{13}$C NMR (75 MHz, DMSO-d$_6$) δ154.3, 152.8, 140.8, 131.4, 130.0, 129.9, 128.2, 125.2, 124.0, 122.7, 117.9, 114.5, 56.8; IR (KBr, cm$^{-1}$) 3442, 1712; MS(ESI) 464 (M−1)$^+$.

Anal Calcd for C$_{13}$H$_9$Br$_2$ClN$_3$O$_2$S C, 33.54; H, 1.73; N, 9.03. Found: C, 33.95; H, 1.92; N, 9.04.

Preparation 4g 5-(5-Bromothiophen-2-yl)-2-(2-hydroxy-5-trifluoromethylphenyl)-2,4-dihydro-[1,2,4]triazol-3-one (IIe, R$^1$=R$^2$=H, R$^3$=CF$_3$)

The title compound was prepared by the general procedure described for Preparations 4a–i using Preparation 2g (4.12 g), (5-bromothiophen-2-yl)-oxo-acetic acid, Preparation 1a (4.7 g), Et$_3$N (2.22 g), and diphenylphosphorylazide, DPPA (6.05 g). Workup gave 5.79 g (69%) of 5-(5-bromothiophen-2-yl)-2-(2-hydroxy-5-trifluoromethylphenyl)-2,4-dihydro-[1,2,4]triazol-3-one. $^1$H NMR (300 MHz, DMSO-d$_6$) δ7.85–7.78 (m, 2 H), 7.42 (d, J=4.0 Hz, 1 H), 7.40 (d, J=8.7 Hz, 1 H), 7.35 (d, J=4.0 Hz, 1 H), 3.87 (s, 3 H); $^{13}$C NMR (75 MHz, DMSO-d$_6$) δ163.3, 158.4, 146.2, 136.8, 135.5, 133.5, 133.1, 131.7, 131.1, 130.5, 126.6(q, J=33 Hz), 61.8; IR (KBr, cm$^{-1}$) 3385 (br), 1702; MS(ESI) 420 (M−1)$^+$.

Anal Calcd for C$_{14}$H$_9$BrF$_3$N$_3$O$_2$S C, 40.02; H, 2.16; N, 10.00. Found: C, 40.15; H, 2.06; N, 10.03.

Preparation 4h

2-(5-Bromo-2-methoxyphenyl)-5-(5-bromothiophen-2-yl)-2,4-dihydro-[1,2,4]triazol-3-one (IIe, $R^1=R^2=$H, $R^3=$Br)

The title compound was prepared by the general procedure described for Preparations 4a–i using Preparation 2h (1.09 g), (5-bromothiophen-2-yl)-oxo-acetic acid, Preparation 1a (1.18 g), $Et_3N$ (0.765 ml), and diphenylphosphorylazide, DPPA (1.19 ml). Workup gave 1.52 g (71%) of 2-(5-bromo-2-methoxyphenyl)-5-(5-bromothiophen-2-yl)-2,4-dihydro-[1,2,4]triazol-3-one. MS (M–H)⁻: 429.84; $^1$H NMR (300 MHz, DMSO-$d_6$) δ12.57 (1H, s), 7.65–7.60 (2H, m), 7.41 (1H, d, J=3.3 Hz), 7.35 (1H, d, J=3.9 Hz), 7.17 (1H, d, J=9.0 Hz), 3.79 (3H, s).

Anal. Calcd. for $C_{13}H_9Br_2N_3O_2S$: C, 36.22; H, 2.10; N, 9.75. Found: C, 35.88; H, 2.17; N, 9.18.

Preparation 4i

5-(5-Bromothiophen-2-yl)-2-(5-fluoro-2-methoxyphenyl)-2,4-dihydro-[1,2,4]triazol-3-one (IIe, $R^1=R^2=$H, $R^3=$Br)

The title compound was prepared by the general procedure described for Preparations 4a–i using Preparation 2i (0.781 g), (5-bromothiophen-2-yl)-oxo-acetic acid, Preparation 1a (1.18 g), $Et_3N$ (0.765 ml), and diphenylphosphorylazide, DPPA (1.19 ml). Workup gave 1.18 g (64%) of 5-(5-bromothiophen-2-yl)-2-(5-fluoro-2-methoxyphenyl)-2,4-dihydro-[1,2,4]triazol-3-one. MS (M–H)⁻: 367.86; $^1$H NMR (300 MHz, DMSO-$d_6$) δ12.57 (1H, s), 7.43–7.18 (5H, m), 3.78 (3H, s).

Anal. Calcd. for $C_{13}H_9BrFN_3O_2S$: C, 42.18; H, 2.45; N, 11.35. Found: C, 42.29; H, 2.47; N, 11.46.

Preparations 5a and 5b

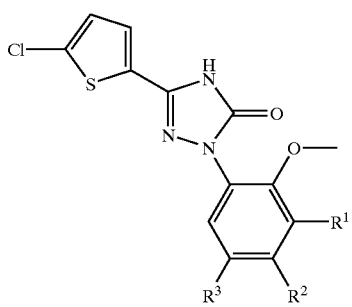

IIf

Preparations 5a and 5b were prepared according to the same general procedure used for Preparations 4a–i with the exception of using (5-chlorothiophen-2-yl)-oxo-acetic acid, Preparation 1b in place of (5-bromothiophen-2-yl)-oxo-acetic acid, Preparation 1b.

Preparation 5a

2-(5-Bromo-2-methoxyphenyl)-5-(5-chlorothiophen-2-yl)-2,4-dihydro-[1,2,4]triazol-3-one (IIf, $R^1=R^2=$H, $R^3=$Br)

The title compound was prepared by the general procedure described for Preparations 5a–b using Preparation 2h (1.085 g, 5.0 mmol), (5-chlorothiophen-2-yl)-oxo-acetic acid, Preparation 1b (953 mg, 5.0 mmol), $Et_3N$ (0.765 mL, 5.5 mmol), and diphenylphosphorylazide, DPPA (1.19 ml, 5.5 mmol). Workup gave 1.34 g (70%) of 2-(5-bromo-2-methoxyphenyl)-5-(5-chlorothiophen-2-yl)-2,4-dihydro-[1,2,4]triazol-3-one. MS (M–H)⁻: 385.88; $^1$H NMR (300 MHz, DMSO-$d_6$) δ7.66–7.60 (2H, m), 7.46 (1H, d, J=4.0 Hz), 7.26 (1H, d, J=4.0 Hz), 7.17 (1H, d, J=8.7 Hz), 3.79 (3H, s).

Anal. Calcd. for $C_{13}H_9BrClN_3O_2S$: C, 40.38; H, 2.35; N, 10.87. Found: C, 40.39; H, 2.29; N, 10.35.

Preparation 5b

5-(5-Chlorothiophen-2-yl)-2-(5-fluoro-2-hydroxyphenyl)-2,4-dihydro-[1,2,4]triazol-3-one (IIf, $R^1=R^2=$H, $R^3=$F)

The title compound was prepared by the general procedure described for Preparations 5a–b using Preparation 2i (781 mg, 5.0 mmol), (5-chlorothiophen-2-yl)-oxo-acetic acid, Preparation 1b (953 mg, 5.0 mmol), $Et_3N$ (0.765 ml, 5.5 mmol), and diphenylphosphorylazide, DPPA (1.19 ml, 5.5 mmol). Workup gave 975 mg (60%) of 5-(5-chlorothiophen-2-yl)-2-(5-fluoro-2-hydroxyphenyl)-2,4-dihydro-[1,2,4]triazol-3-one. MS (M–H)⁻: 323.93; $^1$H NMR (300 MHz, DMSO-$d_6$) δ12.64 (1H, s), 7.68–7.65 (2H, m), 7.47 (1H, d, J=4.2 Hz), 7.40(1H, d, J=3.9 Hz), 7.10 (1H, d, J=8.7 Hz), 3.84 (3H, s).

Anal. Calcd. for $C_{13}H_9FClN_3O_2S$: C, 47.93; H, 2.78; N, 12.90. Found: C, 47.67; H, 2.68; N, 12.96.

Preparation of Compounds of Formula I

Examples 1–28 and 31–32

The compounds of Examples 1–28 and 31–32 were prepared according to the following general procedure.

General Procedure the Preparation of Examples 1–28 and 31–32

An appropriate thiophen-2-yl-2-(5-chloro-2-methoxyphenyl)-2,4-dihydro-[1,2,4]triazol-3-one derivative, Preparation 3a–q (for Examples 1–17); Thiophen-3-yl-2-(5-chloro-2-methoxyphenyl)-2,4-dihydro-[1,2,4]triazol-3-one derivative, Preparation 3r–s (for Examples 18–19); (5-bromothiophen-2-yl)-2-(2-methoxyphenyl)-2,4-dihydro-[1,2,4]triazol-3-one, Preparation 4a–i (for Examples 20–28); or (5-chlorothiophen-2-yl)-2-(2-methoxyphenyl)-2,4-dihydro-[1,2,4]triazol-3-one, Preparation 5a–b (for Examples 31–32) (1.0 equivalent) was suspended in anhydrous dichloromethane (20–25 ml/mmol of Preparation 3a–s, 4a–i, or 5a–b) under argon and cooled to –78° C. A 1M solution of boron tribromide, $BBr_3$ (2–3 equivalents) in anhydrous dichloromethane was added via a dropping funnel over a 45 minute period. After the addition was complete, the reaction mixture was warmed to room temperature and stirred for approximately 5 hours. The reaction mixture was then quenched by the addition of 5–10 ml of water. Volatile solvent was removed under vacuum and the crude product was filtered and washed with water. The resulting solid was refluxed in a mixture of acetone and ethanol for 15 minutes. After cooling to room temperature, the purified product was filtered and washed with acetone and ethanol. The solid was dried under high vacuum to yield the product (compound of Examples 1–17, Ic; Examples 18–19, Id; or Examples 20–28, Ie). If necessary, the product was further purified by recrystallization from THF.

Examples 1–17

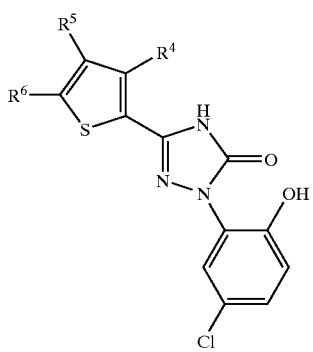

Examples 1–17 (formula Ic) were prepared according to the general procedure above.

Example 1

5-(5-Bromothiophen-2-yl)-2-(5-chloro-2-hydroxyphenyl)-2,4-dihydro-[1,2,4]triazol-3-one (Ic, $R^4=R^5=H$, $R^6=Br$)

The title compound was prepared by the general procedure described above using Preparation 3a (5.00 g, 12.9 mmol) and 1 M BBr$_3$ (40 ml, 40 mmol). Workup gave 3.90 g (81%) of 5-(5-bromothiophen-2-yl)-2-(5-chloro-2-hydroxyphenyl)-2,4-dihydro-[1,2,4]triazol-3-one. MS (M–H)$^-$: 370; $^1$H NMR (300 MHz, DMSO-d$_6$) δ12.66 (1H, s), 10.12 (1H, s), 7.43–7.31 (4H, m), 6.99 (1H, d, J=9.0 Hz). $^{13}$C NMR (75 MHz, DMSO-d$_6$) δ153.20, 151.85, 140.81, 131.49, 130.23, 129.64, 128.14, 127.74, 124.74, 122.11, 118.66, 114.45. IR (KBr) 3234, 1697, 1678, 1606, 1596, 1495, 1460, 1238 cm$^{-1}$.

Anal. Calcd. for C$_{12}$H$_7$N$_3$O$_2$SBrCl: C, 38.68; H, 1.89; N, 11.28. Found: C, 38.80; H, 1.80; N, 11.38.

Example 2

2-(5-Chloro-2-hydroxyphenyl)-5-(5-chlorothiophen-2-yl)-2,4-dihydro-[1,2,4]triazol-3-one (Ic, $R^4=R^5=H$, $R^6=Cl$)

The title compound was prepared by the general procedure described above using Preparation 3b (684 mg, 2.0 mmol) and 1 M BBr$_3$ (4.0 ml, 4.0 mmol). Workup gave 410 mg (63%) of 2-(5-chloro-2-hydroxyphenyl)-5-(5-chlorothiophen-2-yl)-2,4-dihydro-[1,2,4]triazol-3-one. MS (M–H)$^-$: 326.12; $^1$H NMR (300 MHz, DMSO-d$_6$) δ12.67 (1H, s), 10.12 (1H, s), 7.47 (1H, d, J=3.9 Hz), 7.40 (1H, d, J=2.7 Hz), 7.33 (1H, dd, J=8.7 Hz, 2.7 Hz), 7.26 (1H, d, J=4.2 Hz), 6.99 (1H, d, J=8.7 Hz). IR (KBr) 3297, 2884, 1713, 1587, 1500, 1485, 1397, 1264, 1241 cm$^{-1}$.

Anal. Calcd. for C$_{12}$H$_7$N$_3$O$_2$SCl$_2$: C, 43.92; H, 2.15; N, 12.80. Found: C, 43.83; H, 2.30; N, 12.71.

Example 3

2-(5-Chloro-2-hydroxyphenyl)-5-(5-iodothiophen-2-yl)-2,4-dihydro-[1,2,4]triazol-3-one (Ic, $R^4=R^5=H$, $R^6=I$)

The title compound was prepared by the general procedure described above using Preparation 3c (42 mg, 0.096 mmol) and 1 M BBr$_3$ (0.29 ml, 0.29 mmol). Workup gave 21 mg (57%) of 2-(5-chloro-2-hydroxyphenyl)-5-(5-iodothiophen-2-yl)-2,4-dihydro-[1,2,4]triazol-3-one. MS (M–H)$^-$: 417.83; $^1$H NMR (300 MHz, CDCl$_3$) δ9.17 (1H, s), 7.77 (1H, d, J=2.5 Hz), 7.46 (1H, d, J=5.2 Hz), 7.23–7.20 (2H, m), 7.03 (1H, d, J=8.8 Hz).

Example 4

5-(4-Bromothiophen-2-yl)-2-(5-chloro-2-hydroxyphenyl)-2,4-dihydro-[1,2,4]triazol-3-one (Ic, $R^4=R^6=H$, $R^5=Br$)

The title compound was prepared by the general procedure described above using Preparation 3d (774 mg, 2.0 mmol) and 1 M BBr$_3$ (4.0 ml, 4.0 mmol). Workup gave 455 mg (61%) of 5-(4-bromothiophen-2-yl)-2-(5-chloro-2-hydroxyphenyl)-2,4-dihydro-[1,2,4]triazol-3-one. MS (M–H)$^-$: 371.84; $^1$H NMR (300 MHz, DMSO-d$_6$) δ12.62 (1H, s), 10.12 (1H, s), 7.87 (1H, d, J=1.5 Hz), 7.58 (1H, d, J=1.5 Hz), 7.42 (1H, d, J=2.7 Hz), 7.34 (1H, dd, J=8.7 Hz, J=2.7 Hz), 6.99 (1H, d, J=9.0 Hz).

Anal. Calcd. for C$_{12}$H$_7$BrClN$_3$O$_2$S: C, 38.68; H, 1.89; N, 11.28. Found: C, 38.57; H, 2.01; N, 11.21.

Example 5

5-(4-Chlorothiophen-2-yl)-2-(5-chloro-2-hydroxyphenyl)-2,4-dihydro-[1,2,4]triazol-3-one (Ic, $R^4=R^6=H$, $R^5=Cl$)

The title compound was prepared by the general procedure described above using Preparation 3e (684 mg, 2.0 mmol) and 1 M BBr$_3$ (4.0 m, 4.0 mmol). Workup gave 449 mg (68%) of 5-(4-chlorothiophen-2-yl)-2-(5-chloro-2-hydroxyphenyl)-2,4-dihydro-[1,2,4]triazol-3-one. MS (M–H)$^-$: 325.94; $^1$H NMR (300 MHz, DMSO-d6) δ12.64 (1H, s), 10.13 (1H, s), 7.78 (1H, s), 7.55 (1H, s), 7.42–7.31 (2H, m), 6.99 (1H, d, J=8.7 Hz).

Anal. Calcd. for C$_{12}$H$_7$Cl$_2$N$_3$O$_2$S: C, 43.92; H, 2.15; N, 12.80. Found: C, 43.78; H, 2.18; N, 12.99.

Example 6

5-(3-Bromothiophen-2-yl)-2-(5-chloro-2-hydroxyphenyl)-2,4-dihydro-[1,2,4]triazol-3-one (Ic, $R^4=Br$, $R^5=R^6=H$)

The title compound was prepared by the general procedure described above using Preparation 3f (257 mg, 0.67 mmol) and 1 M BBr$_3$ (2.01 ml, 2.01 mmol). Workup gave 148 mg (60%) of 5-(3-bromothiophen-2-yl)-2-(5-chloro-2-hydroxyphenyl)-2,4-dihydro-[1,2,4]triazol-3-one. MS (M–H)$^-$: 371.96; $^1$H NMR (300 MHz, DMSO-d6) δ12.42 (1H, s), 10.16 (1H, s), 7.87 (1H, d, J=5.3 Hz), 7.45 (1H, d, J=2.6 Hz), 7.32 (1H, dd, J=8.8 Hz, J=2.6 Hz), 7.27 (1H, d, J=5.3 Hz), 6.99 (1H, d, J=8.8 Hz). IR (KBr) cm$^{-1}$ 3178.2, 2937.9, 1686.9, 1604.1, 1578.2, 1496.8, 1466.6, 1251.4.

Anal. Calcd. for C$_{12}$H$_7$N$_3$ClBrO$_2$S: C, 38.68; H, 1.89; N, 11.28. Found: C, 38.40; H, 2.11; N, 10.92.

Example 7

2-(5-Chloro-2-hydroxyphenyl)-5-(3-chlorothiophen-2-yl)-2,4-dihydro-[1,2,4]triazol-3-one (Ic, $R^4=Cl$, $R^5=R^6=H$)

The title compound was prepared by the general procedure described above using Preparation 3g (343 mg, 1.0 mmol) and 1 M BBr$_3$ (2.0 mL, 2.0 mmol). Workup gave 186 mg (57%) of 2-(5-chloro-2-hydroxyphenyl)-5-(3-chlorothiophen-2-yl)-2,4-dihydro-[1,2,4]triazol-3-one. MS (M−H)⁻: 326.12; ¹H NMR (300 MHz, DMSO-d₆) δ12.40 (1H, s), 10.15 (1H, s), 7.88 (1H, d, J=5.4 Hz), 7.45 (1H, d, J=2.7 Hz), 7.33 (1H, dd, J=8.7 Hz, 2.7 Hz), 7.24 (1H, d, J=5.4 Hz), 7.00 (1H, d, J=9 Hz). IR (KBr) 3165, 3104, 1688, 1605, 1582, 1497,1469, 1402, 1351, 1252 cm⁻¹.

Anal. Calcd. for $C_{12}H_7N_3O_2SCl_2$: C, 43.92; H, 2.15; N, 12.80. Found: C, 43.95; H, 2.33; N, 12.78.

Example 8

2-(5-Chloro-2-hydroxyphenyl)-5-(3-iodothiophen-2-yl)-2,4-dihydro-[1,2,4]triazol-3-one (Ic, $R^4$=I, $R^5$=$R^6$=H)

The title compound was prepared by the general procedure described above using Preparation 3h (55 mg, 0.13 mmol) and 1 M BBr₃ (0.383 ml, 0.383 mmol). Workup gave 26 mg (63%) of 2-(5-chloro-2-hydroxyphenyl)-5-(3-iodothiophen-2-yl)-2,4-dihydro-[1,2,4]triazol-3-one. MS (M−H)⁻: 417.84; ¹H NMR (300 MHz, DMSO-d₆) δ12.45 (1H, s), 10.15 (1H, s), 7.80 (1H, d, J=5.2 Hz), 7.48 (1H, d, J=2.2 Hz), 7.35–7.31 (2H, m), 7.01 (1H, d, J=8.8 Hz).

Example 9

2-(5-Chloro-2-hydroxyphenyl)-5-(4,5-dibromothiophen-2-yl)-2,4-dihydro-[1,2,4]triazol-3-one (Ic, $R^4$=H, $R^5$=$R^6$=Br)

The title compound was prepared by the general procedure described above using Preparation 3i (270 mg, 0.58 mmol) and 1 M BBr₃ (1.2 ml, 1.2 mmol). Workup gave 191 mg (73%) of 2-(5-chloro-2-hydroxyphenyl)-5-(4,5-dibromothiophen-2-yl)-2,4-dihydro-[1,2,4]triazol-3-one. MS (M−H)⁻: 449.79; ¹H NMR (300 MHz, DMSO-d₆) δ12.65 (1H, s), 10.13 (1H, s), 7.54 (1H, s), 7.41–7.32 (2H, m), 6.99 (1H, d, J=8.7 Hz).

Anal. Calcd. for $C_{12}H_6Br_2ClN_3O_2S \cdot 0.80\ H_2O$: C, 30.93; H, 1.64; N, 9.02. Found: C, 30.87; H, 1.35; N, 8.82.

Example 10

2-(5-Chloro-2-hydroxyphenyl)-5-(4,5-dichlorothiophen-2-yl)-2,4-dihydro-[1,2,4]triazol-3-one (Ic, $R^4$=H, $R^5$=$R^6$=Cl)

The title compound was prepared by the general procedure described above using Preparation 3j (112 mg, 0.30 mmol) and 1 M BBr₃ (0.89 ml, 0.89 mmol). Workup gave 100 mg (90%) of 2-(5-chloro-2-hydroxyphenyl)-5-(4,5-dichlorothiophen-2-yl)-2,4-dihydro-[1,2,4]triazol-3-one. MS (M−H)⁻: 361.82; ¹H NMR (300 MHz, DMSO-d₆) δ12.69 (1H, s), 10.15 (1H, s), 7.56 (1H, s), 7.41 (1H, d, J=2.6 Hz), 7.34 (1H, dd, J=8.8 Hz, J=2.6 Hz), 6.99 (1H, d, J=8.7 Hz).

Example 11

5-(4-Bromo-5-chlorothiophen-2-yl)-2-(5-chloro-2-hydroxyphenyl)-2,4-dihydro-[1,2,4]triazol-3-one (Ic, $R^4$=H, $R^5$=Br, $R^6$=Cl)

The title compound was prepared by the general procedure described above using Preparation 3k (138 mg, 0.33 mmol) and 1 M BBr₃ (0.70 mL, 0.70 mmol). Workup gave 84 mg (63%) of 5-(4-bromo-5-chlorothiophen-2-yl)-2-(5-chloro-2-hydroxyphenyl)-2,4-dihydro-[1,2,4]triazol-3-one. MS (M−H)⁻: 405.81; ¹H NMR (300 MHz, DMSO-d₆) δ12.67 (1H, s), 10.14 (1H, s), 7.56 (1H, s), 7.41 (1H, d, J=2.7 Hz), 7.34 (1H, dd, J=8.7, J=2.7 Hz), 6.99 (1H, d, J=9.0 Hz).

Anal. Calcd. for $C_{12}H_6BrCl_2N_3O_2S$: C, 35.41; H, 1.49; N, 10.32. Found: C, 35.12; H, 1.59; N, 10.28.

Example 12

2-(5-Chloro-2-hydroxyphenyl)-5-(3,4-dibromothiophen-2-yl)-2,4-dihydro-[1,2,4]triazol-3-one (Ic, $R^4$=$R^5$=Br, $R^6$=H)

The title compound was prepared by the general procedure described above using Preparation 3l (271 mg, 0.58 mmol) and 1 M BBr₃ (1.2 ml, 1.2 mmol). Workup gave 227 mg (87%) of 2-(5-chloro-2-hydroxyphenyl)-5-(3,4-dibromothiophen-2-yl)-2,4-dihydro-[1,2,4]triazol-3-one. MS (M−H)⁻: 449.78; ¹H NMR (300 MHz, DMSO-d₆) δ12.52 (1H, s), 10.16 (1H, s), 8.13 (1H, s), 7.45 (1H, d, J=2.7 Hz), 7.34 (1H, dd, J=8.7 Hz, J=2.7 Hz), 7.00 (1H, d, J=8.7 Hz).

Anal. Calcd. for $C_{12}H_6Br_2ClN_3O_2S$: C, 31.92; H, 1.34; N, 9.31. Found: C, 31.88; H, 1.48; N, 9.32.

Example 13

2-(5-Chloro-2-hydroxyphenyl)-5-(3,4-dichlorothiophen-2-yl)-2,4-dihydro-[1,2,4]triazol-3-one (Ic, $R^4$=$R^5$=Cl, $R^6$=H)

The title compound was prepared by the general procedure described above using Preparation 3m (41 mg, 0.11 mmol) and 1 M BBr₃ (0.33 ml, 0.33 mmol). Workup gave 32 mg (82%) of 2-(5-chloro-2-hydroxyphenyl)-5-(3,4-dichlorothiophen-2-yl)-2,4-dihydro-[1,2,4]triazol-3-one. MS (M−H)⁻: 361.89; ¹H NMR (300 MHz, DMSO-d₆) δ12.55 (1H, s), 10.19 (1H, s), 8.07 (1H, s), 7.45 (1H, d, J=2.5 Hz), 7.34 (1H, dd, J=8.8 Hz, J=2.5 Hz), 7.00 (1H, d, J=8.8 Hz).

Example 14

2-(5-Chloro-2-hydroxyphenyl)-5-(3,5-dibromothiophen-2-yl)-2,4-dihydro-[1,2,4]triazol-3-one (Ic, $R^4$=$R^5$=Br, $R^5$=H)

The title compound was prepared by the general procedure described above using Preparation 3n (227 mg, 0.49 mmol) and 1 M BBr₃ (1.0 ml, 1.0 mmol). Workup gave 206 mg (93%) of 2-(5-chloro-2-hydroxyphenyl)-5-(3,5-dibromothiophen-2-yl)-2,4-dihydro-[1,2,4]triazol-3-one. MS (M−H)⁻: 449.80; ¹H NMR (300 MHz, DMSO-d₆) δ12.47 (1H, s), 10.15 (1H, s), 7.53 (1H, s), 7.44 (1H, d, J=2.7 Hz), 7.34 (1H, dd, J=9.0, J=2.7 Hz), 7.00 (1H, d, J=8.7 Hz).

Anal. Calcd. for $C_{12}H_6Br_2ClN_3O_2S \cdot 0.5\ H_2O \cdot 0.25\ CH_2Cl_2$: C, 30.54; H, 1.57; N, 8.72. Found: C, 30.43; H, 1.25; N, 8.61.

Example 15

2-(5-Chloro-2-hydroxyphenyl)-5-(3,4,5-tribromothiophen-2-yl)-2,4-dihydro-[1,2,4]triazol-3-one (Ic, $R^4$=$R^5$=$R^6$=Br)

The title compound was prepared by the general procedure described above using Preparation 3o (78 mg, 0.14 mmol) and 1 M BBr₃ (0.43 ml, 0.43 mmol). Workup gave 45 mg (61%) of 2-(5-chloro-2-hydroxyphenyl)-5-(3,4,5-tribromothiophen-2-yl)-2,4-dihydro-[1,2,4]triazol-3-one.

MS (M−H)$^-$: 529.70; $^1$H NMR (300 MHz, DMSO-$d_6$) δ13.03 (1H, s), 10.62 (1H, s), 7.86 (1H, d, J=2.6 Hz), 7.76 (1H, dd, J=8.8 Hz, J=2.6 Hz), 7.42 (1H, d, J=8.8 Hz). $^{13}$C NMR (75 MHz, DMSO-$d_6$) δ153.14, 151.98, 138.86, 129.84, 127.83, 127.02, 125.73, 124.47, 122.07, 119.29, 118.62, 114.01.

Example 16

2-(5-Chloro-2-hydroxyphenyl)-5-(3,4,5-trichlorothiophen-2-yl)-2,4-dihydro-[1,2,4]triazol-3-one (Ic, $R^4=R^5=R^6=Cl$)

The title compound was prepared by the general procedure described above using Preparation 3p (50 mg, 0.12 mmol) and 1 M BBr$_3$ (0.38 ml, 0.38 mmol). Workup gave 33 mg (66%) of 2-(5-chloro-2-hydroxyphenyl)-5-(3,4,5-trichlorothiophen-2-yl)-2,4-dihydro-[1,2,4]triazol-3one. MS (M−H)$^-$: 395.81; $^1$H NMR (300 MHz, DMSO-$d_6$) δ12.65 (1H, s), 10.22 (1H, s), 7.44 (1H, d, J=2.6 Hz), 7.34 (1H, dd, J=8.7 Hz, J=2.6 Hz), 7.00 (1H, d, J=8.8 Hz). $^{13}$C NMR (75 MHz, DMSO-$d_6$) δ153.17, 152.12, 138.11, 129.96, 128.02, 126.03, 124.35, 123.69, 122.04, 120.79, 118.59.

Example 17

5-(4-Bromo-5-methylthiophen-2-yl)-2-(5-chloro-2-hydroxyphenyl)-2,4-dihydro-[1,2,4]triazol-3-one (Ic, $R^4=H$, $R^5=Br$, $R^6=CH_3$)

The title compound was prepared by the general procedure described above using Preparation 3q (100 mg, 0.25 mmol) and 1 M BBr$_3$ (0.50 ml, 0.50 mmol). Workup gave 55 mg (57%) of 5-(4-bromo-5-methylthiophen-2-yl)-2-(5-chloro-2-hydroxyphenyl)-2,4-dihydro-[1,2,4]triazol-3-one. MS (M−H)$^-$: 385.88; $^1$H NMR (300 MHz, DMSO-$d_6$) δ12.57 (1H, s), 10.12 (1H, s), 7.49 (1H, s), 7.41 (1H, d, J=2.7 Hz), 7.33 (1H, dd, J=8.7, J=2.7 Hz), 6.99 (1H, d, J=8.7 Hz), 2.41 (3H, s).

Anal. Calcd. for $C_{13}H_9BrClN_3O_2S$: C, 40.38; H, 2.35; N, 10.87. Found: C, 41.15; H, 2.61; N, 10.10.

Examples 18–19

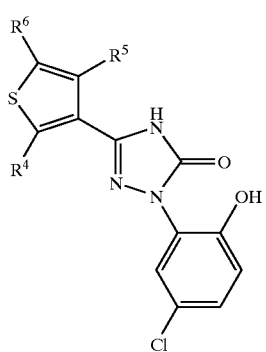

Id

Examples 18–19 (formula Id) were prepared according to the above general procedure.

Example 18

2-(5-Chloro-2-hydroxyphenyl)-5-(2,5-dibromothiophen-3-yl)-2,4-dihydro-[1,2,4]triazol-3-one (Id, $R^4=R^6=Br$, $R^5=H$)

The title compound was prepared by the general procedure described above using Preparation 3r (77 mg, 0.165 mmol) and 1 M BBr$_3$ (0.33 ml, 0.33 mmol). Workup gave 61 mg (82%) of 2-(5-chloro-2-hydroxyphenyl)-5-(2,5-dibromothiophen-3-yl)-2,4-dihydro-[1,2,4]triazol-3-one. MS (M−H)$^-$: 449.75; $^1$H NMR (300 MHz, DMSO-$d_6$) δ12.40 (1H, s), 10.14 (1H, s), 7.51 (1H, s), 7.46 (1H, d, J=2.7 Hz), 7.33 (1H, dd, J=8.7, J=2.4 Hz), 7.00 (1H, d, J=8.7 Hz).

Anal. Calcd. for $C_{12}H_6Br_2ClN_3O_2S$: C, 31.92; H, 1.34; N, 9.31. Found: C, 32.30; H, 1.57; N, 9.24.

Example 19

2-(5-Chloro-2-hydroxyphenyl)-5-(2,5-dichlorothiophen-3-yl)-2,4-dihydro-[1,2,4]triazol-3-one (Id, $R^4=R^6=Cl$, $R^5=H$)

The title compound was prepared by the general procedure described above using Preparation 3s (239 mg, 0.64 mmol) and 1 M BBr$_3$ (1.90 ml, 1.90 mmol). Workup gave 159 mg (70%) of 2-(5-chloro-2-hydroxyphenyl)-5-(2,5-dichlorothiophen-3-yl)-2,4-dihydro-[1,2,4]triazol-3-one. MS (M−H)$^-$: 359.94; $^1$H NMR (300 MHz, DMSO-$d_6$) δ12.40 (1H, s), 10.15 (1H, s), 7.45–7.44 (2H, m), 7.33 (1H, dd, J=8.8 Hz, J=2.6 Hz), 7.00 (1H, d, J=8.8 Hz). IR (KBr) cm$^{-1}$ 3089.1, 2850.9, 2731.6, 1705.8, 1583.2, 1554.5, 1499.9, 1407.2, 1239.8.

Anal. Calcd. for $C_{12}H_6N_3Cl_3O_2S$: C, 39.75; H, 1.67; N, 11.59. Found: C, 39.42; H, 1.94; N, 10.97.

Examples 20–29

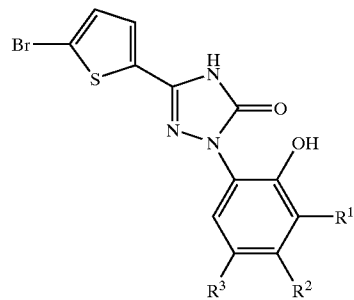

Ie

Examples 20–28 (formula Ie) were prepared according to the general procedure above. Example 29 (formula Ie) was prepared as described below.

Example 20

2-(3-Allyl-5-chloro-2-hydroxyphenyl)-5-(5-bromothiophen-2-yl)-2,4-dihydro-[1,2,4]triazol-3-one (Ie, $R^1=CH_2CH=CH_2$, $R^2=H$, $R^3=Cl$)

The title compound was prepared by the general procedure described above using Preparation 4a (1.28 g) and boron tribromide, BBr$_3$ (9 ml, 1 M). Workup gave 1 g (81%) of 2-(3-Allyl-5-chloro-2-hydroxyphenyl)-5-(5-bromothiophen-2-yl)-2,4-dihydro-[1,2,4]triazol-3-one. $^1$H NMR (300 MHz, DMSO-$d_6$) δ12.9 (s, 1 H), 9.63 (s, 1 H), 7.45 (d, J=4.2 Hz, 1 H), 7.35 (d, J=4.2 Hz, 1 H), 7.31 (d, J=2.7 Hz, 1 H), 7.18 (d, J=2.7 Hz, 1 H), 6.02–5.91 (m, 1 H), 5.14–5.05 (m, 2 H), 3.64 (s, 3 H),3.38 (d, J=6.5 Hz, 2 H); $^{13}$C NMR (75 MHz, DMSO-$d_6$) δ153.7, 148.2, 141.7, 136.1, 131.7, 131.5, 130.2, 129.1, 128.7, 125.4, 123.9, 122.6, 116.6, 115.0, 33.9; IR (KBr, cm$^{-1}$) 1698; MS(ESI) 411 (M−1)$^+$.

Anal Calcd for $C_{15}H_{11}Br_2ClN_3O_2S \cdot 0.2 H_2O$ C, 43.28; H, 2.76; N, 10.09. Found: C, 42.88; H, 2.57; N, 9.98.

Example 21

2-(3-Bromo-5-chloro-2-hydroxyphenyl)-5-(5-bromothiophen-2-yl)-2,4-dihydro-[1,2,4]triazol-3-one (Ie, $R^1$=Br, $R^2$=H, $R^3$=Cl)

The title compound was prepared by the general procedure described above using Preparation 4b (466 mg) and boron tribromide, $BBr_3$ (3 ml, 1 M). Workup gave 100 mg (21%) of 2-(3-bromo-5-chloro-2-hydroxyphenyl)-5-(5-bromothiophen-2-yl)-2,4-dihydro-[1,2,4]triazol-3-one. MS (M−H)⁻: 450; $^1$H NMR (300 MHz, DMSO-$d_6$) δ12.9 (s, 1H), 10.5 (s, 1H), 7.73 (d, J=2.5 Hz, 1H), 7.49 (d, J=2.5 Hz, 1H), 7.45 (d, J=4.0 Hz, 1 H), 7.36 (d, J=4.0 Hz, 1H). $^{13}$C NMR (75 MHz DMSO-$d_6$) δ153.4, 148.2, 141.7, 131.8, 131.5, 130.0, 128.5, 126.1, 125.8, 123.0, 114.8, 112.5.

Example 22

5-(5-Bromothiophen-2-yl)-2-(5-chloro-2-hydroxy-3-methylphenyl)-2,4-dihydro-[1,2,4]triazol-3-one (Ie, $R^1$=$CH_3$, $R^2$=H, $R^3$=Cl)

The title compound was prepared by the general procedure described above using Preparation 4c (1.2 g) and boron tribromide, $BBr_3$ (9 ml, 1 M). Workup gave 1060 mg (92%) of 5-(5-bromothiophen-2-yl)-2-(5-chloro-2-hydroxy-3-methylphenyl)-2,4-dihydro-[1,2,4]triazol-3-one. MS(ESI) 385 (M−1)⁺; IR (KBr, cm⁻¹) 3215 (br), 1698; $^1$H NMR (300 MHz, DMSO-$d_6$) δ9.66 (s, 1 H), 7.59 (d, J=3.6 Hz, 1 H), 7.34 (d, J=3.6 Hz, 1 H), 7.24 (s, 2H), 2.19 (s, 3 H); $^{13}$C NMR (75 MHz, DMSO-$d_6$) δ153.9, 148.7, 142.1, 131.7, 130.5, 129.8, 129.4, 128.9, 125.8, 123.5, 122.3, 114.7, 16.4.

Example 23

5-(5-Bromothiophen-2-yl)-2-(3,5-dichloro-2-hydroxyphenyl)-2,4-dihydro-[1,2,4]triazol-3-one (Ie, $R^1$=$R^3$=Cl, $R^2$=H)

The title compound was prepared by the general procedure described above using Preparation 4d (1.26 g) and boron tribromide, $BBr_3$ (9 ml, 1 M). Workup gave 1039 mg (85%) of 5-(5-bromothiophen-2-yl)-2-(3,5-dichloro-2-hydroxyphenyl)-2,4-dihydro-[1,2,4]triazol-3-one. $^1$H NMR (300 MHz, DMSO-$d_6$) δ7.58 (d, J=2.4 Hz, 1 H), 7.45 (d, J=2.6 Hz, 1 H), 7.44 (d, J=3.9 Hz, 1 H), 7.33 (d, J=3.9 Hz, 1 H); $^{13}$C NMR (75 MHz, DMSO-$d_6$) δ153.6, 147.1, 142.0, 131.4, 130.0, 128.8, 128.4, 126.3, 125.2, 123.1, 122.5, 114.7; IR (KBr, cm⁻¹) 3442 (br), 1715; MS(ESI) 406 (M−1)⁺.

Example 24

5-(5-Bromothiophen-2-yl)-2-(5-chloro-2-hydroxy-4-methylphenyl)-2,4-dihydro-[1,2,4]triazol-3-one (Ie, $R^1$=H, $R^2$=$CH_3$, $R^3$=Cl)

The title compound was prepared by the general procedure described above using Preparation 4e (1.2 g) and boron tribromide, $BBr_3$ (9 ml, 1 M). Workup gave 984 mg (85%) of 5-(5-bromothiophen-2-yl)-2-(5-chloro-2-hydroxy-4-methylphenyl)-2,4-dihydro-[1,2,4]triazol-3-one. $^1$H NMR (300 MHz, DMSO-$d_6$) δ12.5 (s, 1 H), 9.98 (s, 1 H), 7.43 (d, J=4 Hz, 1 H), 7.36 (s, 1 H), 7.34 (d, J=4 Hz, 1 H), 6.90 (s, 1 H), 2.8 (s, 3 H); $^{13}$C NMR (75 MHz, DMSO-$d_6$) δ153.2, 151.4, 140.7, 137.1, 131.4, 130.2, 128.1, 127.7, 122.6, 122.4, 119.3, 114.3, 19.5; IR (KBr, cm⁻¹) 1781; MS(ESI) 385(M−1)⁺.

Anal Calcd for $C_{13}H_9BrClN_3O_2S \cdot 1/2\ H_2O$ C, 39.46; H, 2.55; N, 10.62. Found: C, 39.12; H, 2.31; N, 10.43.

Example 25

2-(4-Bromo-5-chloro-2-hydroxyphenyl)-5-(5-bromothiophen-2-yl)-2,4-dihydro-[1,2,4]triazol-3-one (Ie, $R^1$=H, $R^2$=Br, $R^3$=Cl)

The title compound was prepared by the general procedure described above using Preparation 4f (1.395 g) and boron tribromide, $BBr_3$ (9 ml, 1 M). Workup gave 1098 mg (81%) of 2-(4-bromo-5-chloro-2-hydroxyphenyl)-5-(5-bromothiophen-2-yl)-2,4-dihydro-[1,2,4]triazol-3-one. $^1$H NMR (300 MHz, DMSO-$d_6$) δ12.6 (s, 1 H), 10.5 (s, 1 H), 7.63 (s, 1 H), 7.43 (d, J=4 Hz, 1 H), 7.34 (d, J=4 Hz, 1 H), 7.33 (s, 1 H); $^{13}$C NMR (75 MHz, DMSO-$d_6$) δ153.1, 152.5, 140.9, 131.4, 130.1, 129.2, 128.2, 124.3, 122.4, 121.7, 121.5, 114.5; IR (KBr, cm⁻¹) 3224 (br), 1776; MS(ESI) 450(M−1)⁺.

Anal Calcd for $C_{12}H_6Br_2ClN_3O_2S$ C, 31.92; H, 1.34; N, 9.31. Found: C, 32.34; H, 1.46; N, 9.24.

Example 26

5-(5-Bromothiophen-2-yl)-2-(2-hydroxy-5-trifluoromethylphenyl)-2,4-dihydro-[1,2,4]triazol-3-one (Ie, $R^1$=$R^2$=H, $R^3$=$CF_3$).

The title compound was prepared by the general procedure described above using Preparation 6g (1.26 g) and boron tribromide, $BBr_3$ (9 ml, 1 M). Workup gave 1050 mg (82%) of 5-(5-bromothiophen-2-yl)-2-(2-hydroxy-5-trifluoromethylphenyl)-2,4-dihydro-[1,2,4]triazol-3-one. $^1$H NMR (300 MHz, DMSO-$d_6$) δ12.6 (s, 1 H), 10.8 (s, 1 H), 7.74–7.62 (m, 2 H), 7.43 (d, J=4 Hz, 1 H), 7.37 (d, J=4 Hz, 1 H), 7.16 (d, J=8.5 Hz, 1 H); $^{13}$C NMR (75 MHz, DMSO-$d_6$) δ156.4, 153.2, 140.8, 131.4, 130.2, 128.1, 127.1, 125.9, 123.9, 122.3, 119.5(q, J=32 Hz), 117.8, 114.4; IR (KBr, cm⁻¹) 3188 (br), 1702; MS(ESI) 407 (M)⁺.

Anal Calcd for $C_{13}H_7BrF_3N_3O_2S$ C, 38.44; H, 1.74; N, 10.35. Found: C, 38.21; H, 1.93; N, 10.17.

Example 27

2-(5-Bromo-2-hydroxyphenyl)-5-(5-bromothiophen-2-yl)-2,4-dihydro-[1,2,4]triazol-3-one (Ie, $R^1$=$R^2$=H, $R^3$=Br)

The title compound was prepared by the general procedure described above using Preparation 4h (0.86 g) and boron tribromide, $BBr_3$ (4 ml, 1 M). Workup gave 757 mg (91%) of 2-(5-bromo-2-hydroxyphenyl)-5-(5-bromothiophen-2-yl)-2,4-dihydro-[1,2,4]triazol-3-one. MS (M−H)⁻: 415.80; $^1$H NMR (300 MHz, DMSO-$d_6$) δ12.65 (1H, s), 10.15 (1H, s), 7.52 (1 H, d, J=2.4 Hz), 7.46–7.35 (3H, m), 6.94 (1H, d, J=8.7 Hz).

Anal. Calcd. for $C_{12}H_7Br_2N_3O_2S$: C, 34.56; H,1.69; N, 10.07. Found: C, 34.63; H, 1.85; N, 9.93.

Example 28

5-(5-Bromothiophen-2-yl)-2-(5-fluoro-2-hydroxyphenyl)-2,4-dihydro-[1,2,4]triazol-3-one (Ie, $R^1$=$R^2$=H, $R^3$=F)

The title compound was prepared by the general procedure described above using Preparation 6i (0.74 g) and boron tribromide, $BBr_3$ (4 ml, 1 M). Workup gave 280 mg (40%) of 5-(5-bromothiophen-2-yl)-2-(5-fluoro-2-hydroxyphenyl)-2,4-dihydro-[1,2,4]triazol-3-one. MS (M−H)⁻: 353.88 ; $^1$H NMR (300 MHz, DMSO-$d_6$) δ12.69

(1H, s), 9.77 (1H, s), 7.43 (1H, d, J=3.9 Hz), 7.36 (1H, d, J=3.9 Hz), 7.26–6.95 (3H, m).

Anal. Calcd. for $C_{12}H_7BrFN_3O_2S$: C, 40.47; H, 1.98; N, 11.80. Found: C, 40.68; H, 1.93; N, 11.75.

Example 29

5-(5-Bromothiophen-2-yl)-2-(5-chloro-2-hydroxy-3-(prop-1-en-1-yl)phenyl)-2,4-dihydro-[1,2,4]triazol-3-one (Ie, $R^1$=CH=CHCH$_3$, $R^2$=H, $R^3$=Cl)

A solution of 2-(3-Allyl-5-chloro-2-hydroxyphenyl)-5-(5-bromothiophen-2-yl)-2,4-dihydro-[1,2,4]triazol-3-one (Compound of Example 20) (123 mg) and rhodium trichloride dihydrate, $RhCl_3.2H_2O$ (12 mg) in ethanol (8 ml) was refluxed for 0.5 hours. After concentration, the residue was extracted with ethyl acetate. The organic layer was washed with brine, dried, and concentrated in vacuo to give 110 mg (90%) of 5-(5-bromothiophen-2-yl)-2-(5-chloro-2-hydroxy-3-(prop-2-en-1-yl)phenyl)-2,4-dihydro-[1,2,4]triazol-3-one. $^1$H NMR (300 MHz, DMSO-$d_6$) δ12.9 (s, 1 H), 9.70 (s, 1 H), 7.48 (d, J=2.5 Hz, 1 H), 7.45 (d, J=3.9 Hz, 1 H), 7.35 (d, J=3.9 Hz, 1 H), 7.27 (d, J=2.5 Hz, 1 H), 6.33 (d, J=15.6 Hz, 1 H), 5.14–5.05 (m, 1 H), 1.86 (d, J=5.9 Hz, 3 H); $^{13}$C NMR (75 MHz, DMSO-$d_6$) δ153.5, 147.0, 141.5, 131.5, 130.0, 129.8, 128.4, 128.2, 128.1, 125.6, 125.1, 124.1, 122.9, 114.7, 18.7; IR (KBr, cm$^{-1}$) 1678; MS(ESI) 411 (M+1)$^+$.

Example 30

2-(5-Chloro-2-hydroxy-3-propylphenyl)-5-(thiophen-2-yl)-2,4-dihydro-[1,2,4]triazol-3-one.

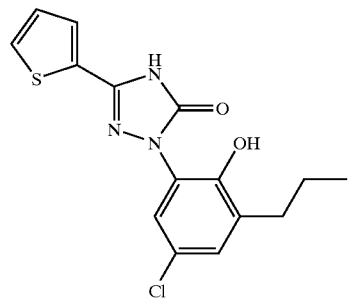

A suspension of 2-(3-Allyl-5-chloro-2-hydroxyphenyl)-5-(5-bromothiophen-2-yl)-2,4-dihydro-[1,2,4]triazol-3-one (Compound of Example 20) (206 mg) and 10%Pt(S)/C (206 mg) in ethanol (8 ml) was hydrogenated at 50 psi for 3 hours. After filtration and concentration, the residue was purified to give 50 mg (30%) of 2-(5-chloro-2-hydroxy-3-propylphenyl)-5-(thiophen-2-yl)-2,4-dihydro-[1,2,4]triazol-3-one. $^1$H NMR (300 MHz, DMSO-$d_6$) δ12.9 (s, 1 H), 9.56 (s, 1 H), 7.79 (dd, J=4.89, 0.9 Hz, 1 H), 7.31 (d, J=2.6 Hz, 1 H), 7.23–7.21 (m, 2 H), 2.61 (t, J=7.4 Hz, 2 H), 1.64 (m, 2 H), 0.94 (t, J=7.2 Hz, 2 H); $^{13}$C NMR (75 MHz, DMSO-$d_6$) δ153.9, 147.9, 142.8, 133.7, 129.4, 129.0, 128.5, 128.3, 125.6, 123.0, 122.6, 31.8, 22.4, 13.9; IR (KBr, cm$^{-1}$) 1701; MS(ESI) 334 (M−1)$^-$.

Examples 31–32

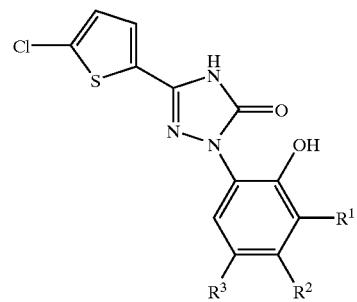

Example 31

2-(5-Bromo-2-hydroxyphenyl)-5-(5-chlorothiophen-2-yl)-2,4-dihydro-[1,2,4]triazol-3-one (If, $R^1$=$R^2$=H, $R^3$=Br)

The title compound was prepared by the general procedure described above using Preparation 5a (773 mg, 2.0 mmol) and boron tribromide, $BBr_3$ (4.0 ml, 4.0 mmol). Workup gave 513 mg (69%) of 2-(5-bromo-2-hydroxyphenyl)-5-(5-chlorothiophen-2-yl)-2,4-dihydro-[1,2,4]triazol-3-one. MS (M−H)$^-$: 371.90; $^1$H NMR (300 MHz, DMSO-$d_6$) δ12.66 (1H, s), 10.17 (1H, s), 7.52–7.42 (3H, m), 7.26 (1H, d, J=3.9 Hz), 6.94(1H, d, J=8.7 Hz).

Anal. Calcd. for $C_{12}H_7BrClN_3O_2S$: C, 38.68; H, 1.89; N, 11.28. Found: C, 38.73; H, 1.89; N, 11.07.

Example 32

5-(5-Chlorothiophen-2-yl)-2-(5-fluoro-2-hydroxyphenyl)-2,4-dihydro-[1,2,4]triazol-3-one (If, $R^1$=$R^2$=H, $R^3$=F)

The title compound was prepared by the general procedure described above using Preparation 5b (652 mg, 2.0 mmol) and boron tribromide, $BBr_3$ (4.0 ml, 4.0 mmol). Workup gave 397 mg (64%) of 5-(5-chlorothiophen-2-yl)-2-(5-fluoro-2-hydroxyphenyl)-2,4-dihydro-[1,2,4]triazol-3-one. MS (M−H)$^-$: 309.99; $^1$H NMR (300 MHz, DMSO-$d_6$) δ12.70 (1H, s), 9.77 (1H, s), 7.47 (1H, d, J=3.9 Hz), 7.27–7.11 (3H, m), 6.99–6.95(1H, m).

Anal. Calcd. for $C_{12}H_7FClN_3O_2S$: C, 46.24; H, 2.26; N, 13.48. Found: C, 46.02; H, 2.27; N, 13.44.

What is claimed is:
1. A compound of formula I

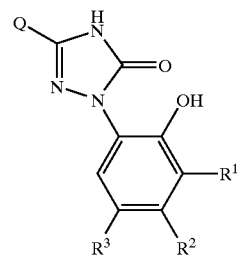

wherein:

Q is

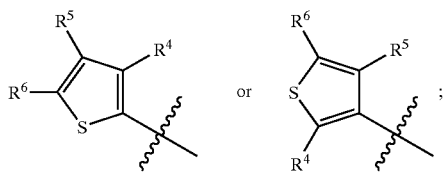

R[1] and R[2] are each independently selected from the group consisting of hydrogen, halogen, $C_{1-6}$alkyl and $C_{2-6}$alkenyl;
R[3] is halogen or trifluoromethyl; and
R[4], R[5] and R[6] are each independently selected from the group consisting of hydrogen, halogen and $C_{1-6}$alkyl;
or a nontoxic pharmaceutically acceptable salt or solvate thereof.

2. The compound of claim 1 in which R[1] and R[2] are hydrogen; or a nontoxic pharmaceutically acceptable salt or solvate thereof.

3. The compound of claim 2 in which Q is

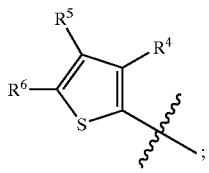

or a nontoxic pharmaceutically acceptable salt or solvate thereof.

4. The compound of claim 3 in which R[3] is selected from the group consisting of fluoro, chloro, bromo and trifluoromethyl; or a nontoxic pharmaceutically acceptable salt or solvate thereof.

5. The compound of claim 4 in which R[4], R[5] and R[6] are each independently selected from the group consisting of hydrogen, chloro, bromo, iodo and methyl; or a nontoxic pharmaceutically acceptable salt or solvate thereof.

6. The compound of claim 2 in which Q is

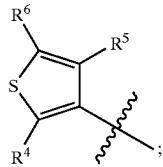

or a nontoxic pharmaceutically acceptable salt or solvate thereof.

7. The compound of claim 6 in which R[3] is chloro; and R[5] is hydrogen; or a nontoxic pharmaceutically acceptable salt or solvate thereof.

8. The compound of claim 7 in which R[4] and R[6] are each independently chloro or bromo; or a nontoxic pharmaceutically acceptable salt or solvate thereof.

9. The compound of claim 1 in which R[1] is hydrogen; and R[2] is halogen or $C_{1-6}$alkyl; or a nontoxic pharmaceutically acceptable salt or solvate thereof.

10. The compound of claim 9 in which Q is

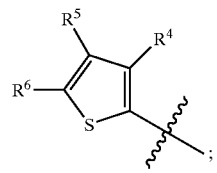

or a nontoxic pharmaceutically acceptable salt or solvate thereof.

11. The compound of claim 10 in which R[2] is bromo or methyl; and R[3] is chloro; or a nontoxic pharmaceutically acceptable salt or solvate thereof.

12. The compound of claim 11 in which R[4] and R[5] are hydrogen; and R[6] is halogen; or a nontoxic pharmaceutically acceptable salt or solvate thereof.

13. The compound of claim 1 in which R[1] is selected from the group consisting of halogen, $C_{1-6}$alkyl and $C_{2-6}$alkenyl; and R[2] is hydrogen; or a nontoxic pharmaceutically acceptable salt or solvate thereof.

14. The compound of claim 13 in which Q is

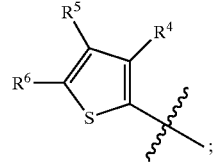

or a nontoxic pharmaceutically acceptable salt or solvate thereof.

15. The compound of claim 14 in which R[1] is selected from the group consisting of chloro, bromo, methyl, propyl, propen-1-yl and propen-3-yl; and R[3] is chloro; or a nontoxic pharmaceutically acceptable salt or solvate thereof.

16. The compound of claim 15 in which R[4] and R[5] are hydrogen; and R[6] is halogen; or a nontoxic pharmaceutically acceptable salt or solvate thereof.

17. The compound of claim 1 selected from the group consisting of:

5-(5-bromothiophen-2-yl)-2-(5-chloro-2-hydroxyphenyl)-2,4-dihydro-[1,2,4]triazol-3-one;
2-(5-chloro-2-hydroxyphenyl)-5-(5-chlorothiophen-2-yl)-2,4-dihydro-[1,2,4]triazol-3-one;
2-(5-chloro-2-hydroxyphenyl)-5-(5-iodothiophen-2-yl)-2,4-dihydro-[1,2,4]triazol-3-one;
5-(4-bromothiophen-2-yl)-2-(5-chloro-2-hydroxyphenyl)-2,4-dihydro-[1,2,4]triazol-3-one;
5-(4-chlorothiophen-2-yl)-2-(5-chloro-2-hydroxyphenyl)-2,4-dihydro-[1,2,4]triazol-3-one;
5-(3-bromothiophen-2-yl)-2-(5-chloro-2-hydroxyphenyl)-2,4-dihydro-[1,2,4]triazol-3-one;
2-(5-chloro-2-hydroxyphenyl)-5-(3-chlorothiophen-2-yl)-2,4-dihydro-[1,2,4]triazol-3-one;
2-(5-chloro-2-hydroxyphenyl)-5-(3-iodothiophen-2-yl)-2,4-dihydro-[1,2,4]triazol-3-one;
2-(5-chloro-2-hydroxyphenyl)-5-(4,5-dibromothiophen-2-yl)-2,4-dihydro-[1,2,4]triazol-3-one;
2-(5-chloro-2-hydroxyphenyl)-5-(4,5-dichlorothiophen-2-yl)-2,4-dihydro-[1,2,4]triazol-3-one;
5-(4-bromo-5-chlorothiophen-2-yl)-2-(5-chloro-2-hydroxyphenyl)-2,4-dihydro-[1,2,4]triazol-3-one;
2-(5-chloro-2-hydroxyphenyl)-5-(3,4-dibromothiophen-2-yl)-2,4-dihydro-[1,2,4]triazol-3-one;

2-(5-chloro-2-hydroxyphenyl)-5-(3,4-dichlorothiophen-2-yl)-2,4-dihydro-[1,2,4]triazol-3-one;

2-(5-chloro-2-hydroxyphenyl)-5-(3,5-dibromothiophen-2-yl)-2,4-dihydro-[1,2,4]triazol-3-one;

2-(5-chloro-2-hydroxyphenyl)-5-(3,4,5-tribromothiophen-2-yl)-2,4-dihydro-[1,2,4]triazol-3-one;

2-(5-chloro-2-hydroxyphenyl)-5-(3,4,5-trichlorothiophen-2-yl)-2,4-dihydro-[1,2,4]triazol-3-one;

5-(4-bromo-5-methylthiophen-2-yl)-2-(5-chloro-2-hydroxyphenyl)-2,4-dihydro-[1,2,4]triazol-3-one;

2-(5-chloro-2-hydroxyphenyl)-5-(2,5-dibromothiophen-3-yl)-2,4-dihydro-[1,2,4]triazol-3-one;

2-(5-chloro-2-hydroxyphenyl)-5-(2,5-dichlorothiophen-3-yl)-2,4-dihydro-[1,2,4]triazol-3-one;

2-(3-allyl-5-chloro-2-hydroxyphenyl)-5-(5-bromothiophen-2-yl)-2,4-dihydro-[1,2,4]triazol-3-one;

2-(3-bromo-5-chloro-2-hydroxyphenyl)-5-(5-bromothiophen-2-yl)-2,4-dihydro-[1,2,4]triazol-3-one;

5-(5-bromothiophen-2-yl)-2-(5-chloro-2-hydroxy-3-methylphenyl)-2,4-dihydro-[1,2,4]triazol-3-one;

5-(5-bromothiophen-2-yl)-2-(3,5-dichloro-2-hydroxyphenyl)-2,4-dihydro-[1,2,4]triazol-3-one;

5-(5-bromothiophen-2-yl)-2-(5-chloro-2-hydroxy-4-methylphenyl)-2,4-dihydro-[1,2,4]triazol-3-one;

2-(4-bromo-5-chloro-2-hydroxyphenyl)-5-(5-bromothiophen-2-yl)-2,4-dihydro-[1,2,4]triazol-3-one;

5-(5-bromothiophen-2-yl)-2-(2-hydroxy-5-trifluoromethylphenyl)-2,4-dihydro-[1,2,4]triazol-3-one;

2-(5-bromo-2-hydroxyphenyl)-5-(5-bromothiophen-2-yl)-2,4-dihydro-[1,2,4]triazol-3-one;

5-(5-bromothiophen-2-yl)-2-(5-fluoro-2-hydroxyphenyl)-2,4-dihydro-[1,2,4]triazol-3-one;

5-(5-bromothiophen-2-yl)-2-(5-chloro-2-hydroxy-3-(prop-1-en-1-yl)phenyl)-2,4-dihydro-[1,2,4]triazol-3-one;

2-(5-chloro-2-hydroxy-3-propylphenyl)-5-(thiophen-2-yl)-2,4-dihydro-[1,2,4]triazol-3-one;

2-(5-bromo-2-hydroxyphenyl)-5-(5-chlorothiophen-2-yl)-2,4-dihydro-[1,2,4]triazol-3-one; and 5-(5-chlorothiophen-2-yl)-2-(5-fluoro-2-hydroxyphenyl)-2,4-dihydro-[1,2,4]triazol-3-one;

or a nontoxic pharmaceutically acceptable salt or solvate thereof.

18. A pharmaceutical composition for the treatment of disorders responsive to relaxation of smooth muscle comprising a therapeutically effective amount of a compound of claim 1 in association with a pharmaceutically acceptable carrier, adjuvant or diluent.

19. A method for the treatment of disorders responsive to relaxation of smooth muscle in a mammal in need thereof, which comprises administering to said mammal a therapeutically effective amount of a compound of claim 1.

20. The method of claim 19 wherein said disorder is urinary incontinence, asthma, irritable bowel syndrome or male erectile dysfunction.

21. The method of claim 20 wherein the disorder is incontinence.

* * * * *